(12) United States Patent
Linder et al.

(10) Patent No.: US 10,660,642 B2
(45) Date of Patent: May 26, 2020

(54) SOFT TISSUE REPAIR DEVICES, SYSTEMS, AND METHODS

(71) Applicant: CONEXTIONS, INC., Sandy, UT (US)

(72) Inventors: Richard J. Linder, Sandy, UT (US); Erik N. Kubiak, Las Vegas, NV (US); Scott D. Miles, Sandy, UT (US); Tyler J. Cole, Sandy, UT (US); Roy M. Taylor, Salt Lake City, UT (US); Kent F. Beck, Layton, UT (US); Shawn P. Reese, Salt Lake City, UT (US)

(73) Assignee: CoNextions, Inc., Salt Lake City, UT (US)

( * ) Notice: Subject to any disclaimer, the term of this patent is extended or adjusted under 35 U.S.C. 154(b) by 278 days.

(21) Appl. No.: 15/464,192

(22) Filed: Mar. 20, 2017

(65) Prior Publication Data
US 2017/0189031 A1    Jul. 6, 2017

Related U.S. Application Data

(60) Division of application No. 14/645,924, filed on Mar. 12, 2015, now Pat. No. 9,629,632, which is a
(Continued)

(51) Int. Cl.
*A61F 2/08* (2006.01)
*A61B 17/11* (2006.01)
(Continued)

(52) U.S. Cl.
CPC ........ *A61B 17/1146* (2013.01); *A61B 17/064* (2013.01); *A61B 17/068* (2013.01);
(Continued)

(58) Field of Classification Search
CPC .................. A61B 17/1146; A61F 2002/0864
See application file for complete search history.

(56) References Cited

U.S. PATENT DOCUMENTS 3,166,072 A    1/1965  Sullivan et al.
4,388,926 A    6/1983  Shalaby et al.
(Continued)

OTHER PUBLICATIONS

McKenzie, "An Experimental Multiple Barbed Suture for The Long Flexor Tendons of The Palm and Fingers," Journal of Bone and Joint Surgery, Aug. 1967, pp. 440-447, vol. 49 B, No. 3.
(Continued)

*Primary Examiner* — Megan Y Wolf
(74) *Attorney, Agent, or Firm* — David L. Stott

(57) ABSTRACT

Devices, systems and/or methods for repairing a lacerated tendon or ligament adjacent a repair site. In one embodiment, a repair device includes an elongated flexible structure and multiple anchors, the multiple anchors pre-positioned with the elongated flexible structure. The repair device may be coupled to the tendon or ligament at the repair site with a delivery device. The repair device may be pre-positioned in a cartridge such that the cartridge is loaded into the delivery device. The lacerated tendon or ligament is positioned within a cradle portion of the delivery device such that the tendon is positioned between the cradle portion and the cartridge that holds the repair device. The delivery device may then be triggered to actuate and drive the repair device from the cartridge to couple to the lacerated tendon or ligament. In this manner, the repair device may be anchored to the lacerated tendon.

20 Claims, 22 Drawing Sheets

Related U.S. Application Data continuation-in-part of application No. 13/953,709, filed on Jul. 29, 2013, now Pat. No. 9,427,309.

(60) Provisional application No. 61/804,570, filed on Mar. 22, 2013, provisional application No. 61/677,239, filed on Jul. 30, 2012, provisional application No. 62/053,056, filed on Sep. 19, 2014, provisional application No. 62/040,451, filed on Aug. 22, 2014, provisional application No. 62/007,783, filed on Jun. 4, 2014, provisional application No. 61/952,114, filed on Mar. 12, 2014.

(51) Int. Cl.
*A61B 17/06* (2006.01)
*A61B 17/064* (2006.01)
*A61B 17/068* (2006.01)
*A61B 17/072* (2006.01)
*A61B 17/08* (2006.01)
*A61B 17/04* (2006.01)
*A61B 17/00* (2006.01)
*A61B 17/3211* (2006.01)

(52) U.S. Cl.
CPC .... *A61B 17/0644* (2013.01); *A61B 17/06166* (2013.01); *A61B 17/072* (2013.01); *A61B 17/07292* (2013.01); *A61B 17/08* (2013.01); *A61F 2/0811* (2013.01); *A61B 17/0487* (2013.01); *A61B 17/3211* (2013.01); *A61B 2017/00867* (2013.01); *A61B 2017/0496* (2013.01); *A61B 2017/0641* (2013.01); *A61B 2017/1103* (2013.01); *A61B 2017/1132* (2013.01)

(56) References Cited

U.S. PATENT DOCUMENTS

| | | |
|---|---|---|
| 4,414,967 A | 11/1983 | Shapiro |
| 4,461,298 A | 7/1984 | Shalaby et al. |
| 4,469,101 A | 9/1984 | Coleman et al. |
| 4,489,875 A | 12/1984 | Crawford et al. |
| 4,532,926 A | 8/1985 | O'Holla |
| 4,534,350 A | 8/1985 | Golden et al. |
| 4,548,202 A | 10/1985 | Duncan |
| 4,610,250 A | 9/1986 | Green |
| 4,655,980 A | 4/1987 | Chu |
| 4,741,330 A | 5/1988 | Hayhurst |
| 4,776,890 A | 10/1988 | Chu |
| 4,796,612 A | 1/1989 | Reese |
| 4,810,549 A | 3/1989 | Abrams et al. |
| 4,873,976 A | 10/1989 | Schreiber |
| 4,942,875 A | 7/1990 | Hlavacek et al. |
| 4,946,467 A | 8/1990 | Ohi et al. |
| 4,960,420 A | 10/1990 | Goble et al. |
| 4,983,184 A | 1/1991 | Steinemann |
| 5,047,103 A | 9/1991 | Abrams et al. |
| 5,061,283 A | 10/1991 | Silvestrini |
| 5,163,956 A | 11/1992 | Liu et al. |
| 5,207,841 A | 5/1993 | Abrams |
| 5,250,049 A | 10/1993 | Michael |
| 5,290,552 A | 3/1994 | Sierra et al. |
| 5,292,334 A | 3/1994 | Howansky |
| 5,306,290 A | 4/1994 | Martins et al. |
| 5,306,500 A | 4/1994 | Rhee et al. |
| 5,312,023 A | 5/1994 | Green et al. |
| 5,326,013 A | 7/1994 | Green et al. |
| 5,329,943 A | 7/1994 | Johnson |
| 5,342,376 A | 8/1994 | Ruff |
| 5,346,746 A | 9/1994 | Abrams |
| 5,370,662 A | 12/1994 | Stone et al. |
| 5,389,098 A | 2/1995 | Tsuruta et al. |
| 5,413,791 A | 5/1995 | Rhee et al. |
| 5,446,091 A | 8/1995 | Rhee et al. |
| 5,447,265 A | 9/1995 | Vidal et al. |
| 5,458,636 A | 10/1995 | Brancato |
| 5,465,894 A | 11/1995 | Clark et al. |
| 5,480,644 A | 1/1996 | Freed |
| 5,510,418 A | 4/1996 | Rhee et al. |
| 5,523,348 A | 6/1996 | Rhee et al. |
| 5,527,341 A | 6/1996 | Gogolewski et al. |
| 5,542,594 A | 8/1996 | McKean et al. |
| 5,556,428 A | 9/1996 | Shah |
| 5,575,803 A | 11/1996 | Cooper et al. |
| 5,580,923 A | 12/1996 | Yeung et al. |
| 5,597,637 A | 1/1997 | Abrams et al. |
| 5,603,443 A | 2/1997 | Clark et al. |
| 5,607,094 A | 3/1997 | Clark et al. |
| 5,630,824 A | 5/1997 | Hart |
| 5,630,842 A | 5/1997 | Brodniewicz |
| 5,649,937 A | 7/1997 | Bito et al. |
| 5,665,112 A | 9/1997 | Thal |
| 5,667,839 A | 9/1997 | Berg |
| 5,711,472 A | 1/1998 | Bryan |
| 5,713,903 A | 2/1998 | Sander et al. |
| 5,716,981 A | 2/1998 | Hunter et al. |
| 5,723,008 A | 3/1998 | Gordon |
| 5,728,110 A | 3/1998 | Vidal et al. |
| 5,732,871 A | 3/1998 | Clark et al. |
| 5,756,678 A | 5/1998 | Shenoy et al. |
| 5,766,250 A | 6/1998 | Chervitz et al. |
| 5,800,544 A | 9/1998 | Demopulos et al. |
| 5,807,581 A | 9/1998 | Rosenblatt et al. |
| 5,858,156 A | 1/1999 | Abrams et al. |
| 5,860,229 A | 1/1999 | Morgenstern |
| 5,865,361 A | 2/1999 | Milliman et al. |
| 5,908,427 A | 6/1999 | McKean et al. |
| 5,916,224 A | 6/1999 | Esplin |
| 5,961,520 A | 10/1999 | Beck, Jr. et al. |
| 5,964,774 A | 10/1999 | McKean et al. |
| 5,980,524 A | 11/1999 | Justin et al. |
| 5,997,811 A | 12/1999 | Esposito |
| 6,010,764 A | 1/2000 | Abrams |
| 6,013,083 A | 1/2000 | Bennett |
| 6,027,523 A | 2/2000 | Schmieding |
| 6,030,410 A | 2/2000 | Zurbrugg |
| 6,045,560 A | 4/2000 | McKean et al. |
| 6,079,606 A | 6/2000 | Milliman et al. |
| 6,080,192 A | 6/2000 | Demopulos et al. |
| 6,083,242 A | 7/2000 | Cook |
| 6,083,332 A | 7/2000 | Abrams |
| 6,086,547 A | 7/2000 | Hanssen et al. |
| 6,099,538 A | 8/2000 | Moses et al. |
| 6,106,556 A | 8/2000 | Demopulos et al. |
| 6,110,560 A | 8/2000 | Abrams |
| 6,111,165 A | 8/2000 | Berg |
| 6,206,886 B1 | 3/2001 | Bennett |
| 6,241,139 B1 | 6/2001 | Milliman et al. |
| 6,241,747 B1 | 6/2001 | Ruff |
| 6,250,532 B1 | 6/2001 | Green et al. |
| 6,277,394 B1 | 8/2001 | Sierra |
| 6,330,965 B1 | 12/2001 | Milliman et al. |
| 6,333,347 B1 | 12/2001 | Hunter et al. |
| 6,358,557 B1 | 3/2002 | Wang et al. |
| 6,383,199 B2 | 5/2002 | Carter et al. |
| 6,413,742 B1 | 7/2002 | Olsen et al. |
| D462,766 S | 9/2002 | Jacobs et al. |
| 6,464,706 B1 | 10/2002 | Winters |
| 6,472,171 B1 | 10/2002 | Toman et al. |
| 6,485,503 B2 | 11/2002 | Jacobs et al. |
| 6,491,714 B1 | 12/2002 | Bennett |
| 6,495,127 B1 | 12/2002 | Wallace et al. |
| 6,515,016 B2 | 2/2003 | Hunter |
| 6,517,579 B1 | 2/2003 | Paulos et al. |
| 6,533,802 B2 | 3/2003 | Bojarski et al. |
| 6,544,273 B1 | 4/2003 | Harari et al. |
| 6,551,315 B2 | 4/2003 | Kortenbach et al. |
| 6,569,186 B1 | 5/2003 | Winters et al. |
| 6,575,976 B2 | 6/2003 | Grafton |
| 6,644,532 B2 | 11/2003 | Green et al. |
| 6,645,226 B1 | 11/2003 | Jacobs et al. |
| 6,648,893 B2 | 11/2003 | Dudasik |

(56) References Cited

U.S. PATENT DOCUMENTS

| | | |
|---|---|---|
| 6,652,563 B2 | 11/2003 | Dreyfuss |
| 6,656,183 B2 | 12/2003 | Colleran et al. |
| 6,666,873 B1 | 12/2003 | Cassell |
| 6,669,073 B2 | 12/2003 | Milliman et al. |
| 6,689,803 B2 | 2/2004 | Hunter |
| 6,712,830 B2 | 3/2004 | Esplin |
| 6,716,226 B2 | 4/2004 | Sixto, Jr. et al. |
| 6,740,100 B2 | 5/2004 | Demopulos et al. |
| 6,743,233 B1 | 6/2004 | Baldwin et al. |
| 6,743,240 B2 | 6/2004 | Smith et al. |
| 6,773,450 B2 | 8/2004 | Leung et al. |
| 6,824,548 B2 | 11/2004 | Smith et al. |
| 6,830,174 B2 | 12/2004 | Hillstead et al. |
| 6,843,794 B2 | 1/2005 | Sixto, Jr. et al. |
| 6,877,647 B2 | 4/2005 | Green et al. |
| 6,893,452 B2 | 5/2005 | Jacobs |
| 6,905,513 B1 | 6/2005 | Metzger |
| 6,945,979 B2 | 9/2005 | Kortenbach et al. |
| 6,953,138 B1 | 10/2005 | Dworak et al. |
| 6,953,139 B2 | 10/2005 | Milliman et al. |
| 6,962,594 B1 | 11/2005 | Thevenet |
| 6,991,643 B2 | 1/2006 | Saadat |
| 7,016,194 B1 | 3/2006 | Wong |
| 7,056,331 B2 | 6/2006 | Kaplan et al. |
| 7,070,602 B2 | 7/2006 | Smith et al. |
| 7,074,203 B1 | 7/2006 | Johanson et al. |
| 7,090,685 B2 | 8/2006 | Kortenbach et al. |
| 7,121,446 B2 | 10/2006 | Arad et al. |
| 7,129,209 B2 | 10/2006 | Rhee |
| 7,156,862 B2 | 1/2007 | Jacobs et al. |
| 7,172,615 B2 | 2/2007 | Morriss et al. |
| 7,176,256 B2 | 2/2007 | Rhee et al. |
| 7,189,238 B2 | 3/2007 | Lombardo et al. |
| 7,226,468 B2 | 6/2007 | Ruff |
| 7,229,413 B2 | 6/2007 | Violante et al. |
| 7,232,445 B2 | 6/2007 | Kortenbach et al. |
| 7,275,674 B2 * | 10/2007 | Racenet ............... A61B 17/072 227/175.1 |
| 7,296,724 B2 | 11/2007 | Green et al. |
| 7,303,107 B2 | 12/2007 | Milliman et al. |
| 7,309,346 B2 | 12/2007 | Martinek |
| 7,328,829 B2 | 2/2008 | Arad et al. |
| 7,343,920 B2 | 3/2008 | Toby et al. |
| 7,354,627 B2 | 4/2008 | Pedrozo et al. |
| 7,398,907 B2 | 7/2008 | Racenet et al. |
| 7,401,720 B1 | 7/2008 | Durrani |
| 7,438,209 B1 | 10/2008 | Hess et al. |
| 7,442,202 B2 | 10/2008 | Dreyfuss |
| 7,464,848 B2 | 12/2008 | Green et al. |
| 7,510,566 B2 | 3/2009 | Jacobs et al. |
| 7,530,484 B1 | 5/2009 | Durrani |
| 7,530,990 B2 | 5/2009 | Perriello et al. |
| 7,565,993 B2 | 7/2009 | Milliman et al. |
| 7,568,604 B2 | 8/2009 | Ehrenfels et al. |
| 7,600,663 B2 | 10/2009 | Green |
| 7,604,151 B2 | 10/2009 | Hess et al. |
| 7,611,038 B2 | 11/2009 | Racenet et al. |
| 7,611,521 B2 | 11/2009 | Lubbers et al. |
| 7,615,058 B2 | 11/2009 | Sixto, Jr. et al. |
| 7,624,487 B2 | 12/2009 | Trull et al. |
| 7,635,074 B2 | 12/2009 | Olson et al. |
| 7,640,617 B2 | 1/2010 | Kennedy et al. |
| 7,641,091 B2 | 1/2010 | Olson et al. |
| 7,665,646 B2 | 2/2010 | Prommersberger |
| 7,708,759 B2 | 5/2010 | Lubbers et al. |
| 7,727,246 B2 | 6/2010 | Sixto, Jr. et al. |
| 7,727,248 B2 | 6/2010 | Smith et al. |
| 7,731,718 B2 | 6/2010 | Schwammberger et al. |
| 7,771,468 B2 | 8/2010 | Whitbourne et al. |
| 7,794,484 B2 | 9/2010 | Stone et al. |
| 7,819,896 B2 | 10/2010 | Racenet |
| 7,824,426 B2 | 11/2010 | Racenet et al. |
| 7,828,189 B2 | 11/2010 | Holsten et al. |
| 7,842,097 B2 | 11/2010 | Yamamoto et al. |
| 7,845,533 B2 | 12/2010 | Marczyk et al. |
| 7,861,907 B2 | 1/2011 | Green et al. |
| 7,887,551 B2 | 2/2011 | Bojarski et al. |
| 7,891,531 B1 | 2/2011 | Ward |
| 7,909,224 B2 | 3/2011 | Prommersberger |
| 7,926,692 B2 | 4/2011 | Racenet et al. |
| 7,942,304 B2 | 5/2011 | Taylor et al. |
| 7,942,885 B2 | 5/2011 | Sixto, Jr. et al. |
| 7,950,561 B2 | 5/2011 | Aranyi |
| 8,006,700 B2 | 8/2011 | Demopulos et al. |
| 8,008,598 B2 | 8/2011 | Whitman et al. |
| 8,011,550 B2 | 9/2011 | Aranyi et al. |
| 8,016,177 B2 | 9/2011 | Bettuchi et al. |
| 8,016,178 B2 | 9/2011 | Olson et al. |
| 8,021,378 B2 | 9/2011 | Sixto, Jr. et al. |
| 8,029,563 B2 | 10/2011 | House et al. |
| 8,033,439 B2 | 10/2011 | Racenet et al. |
| 8,038,045 B2 | 10/2011 | Bettuchi et al. |
| 8,043,328 B2 | 10/2011 | Hahnen et al. |
| 8,062,314 B2 | 11/2011 | Sixto, Jr. et al. |
| 8,062,330 B2 | 11/2011 | Prommersberger et al. |
| 8,062,363 B2 | 11/2011 | Hirpara et al. |
| 8,066,721 B2 | 11/2011 | Kortenbach et al. |
| 8,070,033 B2 | 12/2011 | Milliman et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman |
| 8,113,409 B2 | 2/2012 | Cohen et al. |
| 8,114,129 B2 | 2/2012 | Lubbers et al. |
| 8,118,834 B1 | 2/2012 | Goraltchouk et al. |
| 8,123,101 B2 | 2/2012 | Racenet |
| 8,141,762 B2 | 3/2012 | Bedi et al. |
| 8,157,151 B2 | 4/2012 | Ingmanson et al. |
| 8,186,557 B2 | 5/2012 | Cohen et al. |
| 8,186,560 B2 | 5/2012 | Hess et al. |
| 8,205,620 B2 | 6/2012 | Taylor et al. |
| 8,210,414 B2 | 7/2012 | Bettuchi et al. |
| 8,210,416 B2 | 7/2012 | Milliman et al. |
| 8,256,654 B2 | 9/2012 | Bettuchi et al. |
| 8,256,656 B2 | 9/2012 | Milliman et al. |
| 8,292,152 B2 | 10/2012 | Milliman et al. |
| 8,298,286 B2 | 10/2012 | Trieu |
| 8,308,041 B2 | 11/2012 | Kostrzewski |
| 8,308,042 B2 | 11/2012 | Aranyi |
| 8,308,046 B2 | 11/2012 | Prommersberger |
| 8,322,455 B2 | 12/2012 | Shelton, IV et al. |
| 8,328,061 B2 | 12/2012 | Kasvikis |
| 8,342,377 B2 | 1/2013 | Milliman et al. |
| 8,343,186 B2 | 1/2013 | Dreyfuss et al. |
| 8,348,129 B2 | 1/2013 | Bedi et al. |
| 8,439,936 B2 | 5/2013 | McClellan |
| 8,453,905 B2 | 6/2013 | Holcomb et al. |
| 8,453,910 B2 | 6/2013 | Bettuchi et al. |
| 8,464,925 B2 | 6/2013 | Hull et al. |
| 8,469,252 B2 | 6/2013 | Holcomb et al. |
| 8,480,692 B2 | 7/2013 | McClellan |
| 8,485,412 B2 | 7/2013 | Shelton, IV et al. |
| 8,491,600 B2 | 7/2013 | McDevitt et al. |
| 8,500,776 B2 | 8/2013 | Ebner |
| 8,518,091 B2 | 8/2013 | McDevitt et al. |
| 8,540,131 B2 | 9/2013 | Swayze |
| 8,550,325 B2 | 10/2013 | Cohen et al. |
| 8,574,275 B2 | 11/2013 | Stone et al. |
| 8,585,721 B2 | 11/2013 | Kirsch |
| 8,602,286 B2 | 12/2013 | Crainich et al. |
| 8,608,765 B1 | 12/2013 | Jurbala |
| 8,613,384 B2 | 12/2013 | Pastorelli et al. |
| 8,616,430 B2 | 12/2013 | (Prommersberger) Stopek |
| 8,623,052 B2 | 1/2014 | Dreyfuss et al. |
| 8,636,766 B2 | 1/2014 | Milliman et al. |
| 8,668,130 B2 | 3/2014 | Hess et al. |
| 8,684,249 B2 | 4/2014 | Racenet et al. |
| 8,720,766 B2 | 5/2014 | Hess et al. |
| 8,740,034 B2 | 6/2014 | Morgan et al. |
| 8,801,732 B2 | 8/2014 | Harris et al. |
| 8,801,755 B2 | 8/2014 | Dreyfuss et al. |
| 8,814,904 B2 | 8/2014 | Bennett |
| 8,834,543 B2 | 9/2014 | McDevitt et al. |
| 8,840,003 B2 | 9/2014 | Morgan et al. |

(56) References Cited

U.S. PATENT DOCUMENTS

| | | |
|---|---|---|
| 8,845,686 B2 | 9/2014 | Bennett |
| 8,905,287 B2 | 12/2014 | Racenet et al. |
| 8,939,983 B2 | 1/2015 | Stone et al. |
| 9,204,960 B2 | 12/2015 | Albertorio et al. |
| 9,277,909 B2 | 3/2016 | Brunsvold |
| 9,307,979 B1 | 4/2016 | Bennett et al. |
| 9,427,309 B2 | 8/2016 | Kubiak et al. |
| 9,439,645 B2 | 9/2016 | Stone et al. |
| 9,451,961 B2 | 9/2016 | Kubiak |
| 9,486,207 B2 | 11/2016 | Dooney, Jr. et al. |
| 9,642,610 B2 | 5/2017 | Albertorio et al. |
| 9,655,625 B2 | 5/2017 | Kubiak et al. |
| 9,700,305 B2 | 7/2017 | Bennett et al. |
| 10,219,804 B2 | 3/2019 | Linder et al. |
| 2001/0044637 A1 | 11/2001 | Jacobs et al. |
| 2001/0051815 A1 | 12/2001 | Esplin |
| 2002/0013298 A1 | 1/2002 | Hunter |
| 2002/0022861 A1 | 2/2002 | Jacobs et al. |
| 2002/0055666 A1 | 5/2002 | Hunter et al. |
| 2002/0077661 A1 | 6/2002 | Saadat |
| 2002/0123750 A1 | 9/2002 | Eisermann et al. |
| 2002/0192280 A1 | 12/2002 | Hunter et al. |
| 2003/0069602 A1 | 4/2003 | Jacobs et al. |
| 2003/0105489 A1 | 6/2003 | Eichhorn et al. |
| 2003/0120309 A1 | 6/2003 | Colleran et al. |
| 2003/0130694 A1 | 7/2003 | Bojarski et al. |
| 2003/0153972 A1 | 8/2003 | Helmus |
| 2003/0157170 A1 | 8/2003 | Liggins et al. |
| 2003/0181371 A1 | 9/2003 | Hunter et al. |
| 2003/0203976 A1 | 10/2003 | Hunter et al. |
| 2004/0006352 A1 | 1/2004 | Nobles et al. |
| 2004/0010276 A1 | 1/2004 | Jacobs et al. |
| 2004/0039404 A1 | 2/2004 | Dreyfuss |
| 2004/0059336 A1 | 3/2004 | Lombardo et al. |
| 2004/0060410 A1 | 4/2004 | Leung et al. |
| 2004/0076672 A1 | 4/2004 | Hunter et al. |
| 2004/0088003 A1 | 5/2004 | Leung et al. |
| 2004/0153153 A1 | 8/2004 | Elson et al. |
| 2004/0193217 A1 | 9/2004 | Lubbers et al. |
| 2004/0199241 A1 | 10/2004 | Gravett et al. |
| 2004/0219214 A1 | 11/2004 | Gravett et al. |
| 2004/0220591 A1 | 11/2004 | Bonutti |
| 2004/0224023 A1 | 11/2004 | Hunter et al. |
| 2004/0254609 A1 | 12/2004 | Esplin |
| 2004/0267362 A1 | 12/2004 | Hwang et al. |
| 2005/0090827 A1 | 4/2005 | Gedebou |
| 2005/0152941 A1 | 7/2005 | Hunter et al. |
| 2005/0175665 A1 | 8/2005 | Hunter et al. |
| 2005/0186261 A1 | 8/2005 | Avelar et al. |
| 2005/0192428 A1 | 9/2005 | Berg et al. |
| 2005/0197699 A1 | 9/2005 | Jacobs et al. |
| 2006/0127445 A1 | 6/2006 | Hunter et al. |
| 2006/0135994 A1 | 6/2006 | Ruff et al. |
| 2006/0147332 A1 | 7/2006 | Jones |
| 2006/0149349 A1 | 7/2006 | Garbe |
| 2006/0240064 A9 | 10/2006 | Hunter et al. |
| 2006/0240113 A1 | 10/2006 | Hunter et al. |
| 2006/0247641 A1 | 11/2006 | Re et al. |
| 2007/0021779 A1 | 1/2007 | Garvin et al. |
| 2007/0026043 A1 | 2/2007 | Guan et al. |
| 2007/0027527 A1 | 2/2007 | Williams et al. |
| 2007/0065663 A1 | 3/2007 | Trull et al. |
| 2007/0123984 A1 | 5/2007 | Hodorek |
| 2007/0156158 A1 | 7/2007 | Herzberg et al. |
| 2007/0196421 A1 | 8/2007 | Hunter et al. |
| 2007/0208355 A1 | 9/2007 | Ruff |
| 2007/0208377 A1 | 9/2007 | Kaplan et al. |
| 2008/0003394 A1 | 1/2008 | Eke |
| 2008/0027443 A1 | 1/2008 | Lambert |
| 2008/0027445 A1 | 1/2008 | Brown, Jr. et al. |
| 2008/0027446 A1 | 1/2008 | Stone et al. |
| 2008/0027486 A1 | 1/2008 | Jones et al. |
| 2008/0051888 A1 | 2/2008 | Ratcliffe et al. |
| 2008/0058579 A1 | 3/2008 | Hunter et al. |
| 2008/0124400 A1 | 5/2008 | Liggins et al. |
| 2008/0195204 A1 | 8/2008 | Zhukauskas et al. |
| 2008/0234731 A1 | 9/2008 | Leung et al. |
| 2008/0247987 A1 | 10/2008 | Liggins et al. |
| 2008/0281325 A1 | 11/2008 | Stone et al. |
| 2008/0312315 A1 | 12/2008 | Daniloff et al. |
| 2009/0012560 A1 | 1/2009 | Hunter et al. |
| 2009/0018577 A1 | 1/2009 | Leung et al. |
| 2009/0048537 A1 | 2/2009 | Lydon et al. |
| 2009/0048616 A1 | 2/2009 | Gonzalez-Hernandez |
| 2009/0060973 A1 | 3/2009 | Hunter et al. |
| 2009/0107965 A1 | 4/2009 | D'Agostino |
| 2009/0112259 A1 | 4/2009 | D'Agostino |
| 2009/0117070 A1 | 5/2009 | Daniloff et al. |
| 2009/0125094 A1 | 5/2009 | Rust |
| 2009/0143819 A1 | 6/2009 | D'Agostino |
| 2009/0156980 A1 | 6/2009 | Eaton et al. |
| 2009/0216326 A1 | 8/2009 | Hirpara et al. |
| 2009/0222039 A1 | 9/2009 | Dreyfuss et al. |
| 2009/0226500 A1 | 9/2009 | Avelar et al. |
| 2009/0228021 A1 | 9/2009 | Leung |
| 2009/0234386 A1 | 9/2009 | Jean et al. |
| 2009/0280153 A1 | 11/2009 | Hunter et al. |
| 2009/0324720 A1 | 12/2009 | He et al. |
| 2010/0016872 A1 | 1/2010 | Bayton et al. |
| 2010/0160718 A1 | 6/2010 | Villafana et al. |
| 2010/0193568 A1 | 8/2010 | Scheib et al. |
| 2010/0217314 A1 | 8/2010 | Holsten et al. |
| 2010/0249802 A1 | 9/2010 | May et al. |
| 2010/0324676 A1 | 12/2010 | Albertorio et al. |
| 2011/0106253 A1 | 5/2011 | Barwood et al. |
| 2011/0124956 A1 | 5/2011 | Mujwid |
| 2011/0125287 A1 | 5/2011 | Hotter et al. |
| 2011/0155787 A1 | 6/2011 | Baxter, III et al. |
| 2011/0288565 A1 | 11/2011 | Kubiak et al. |
| 2011/0288566 A1 | 11/2011 | Kubiak |
| 2011/0301706 A1 | 12/2011 | Brooks et al. |
| 2012/0080336 A1 | 4/2012 | Shelton, IV et al. |
| 2012/0130374 A1 | 5/2012 | Bouduban et al. |
| 2012/0203253 A1 | 8/2012 | Kubiak |
| 2012/0245629 A1* | 9/2012 | Gross ............... A61B 17/06166 606/228 |
| 2013/0131781 A1 | 5/2013 | Greenhalgh et al. |
| 2013/0144310 A1 | 6/2013 | Gordon et al. |
| 2013/0197580 A1 | 8/2013 | Perriello et al. |
| 2014/0039551 A1 | 2/2014 | Donahue |
| 2015/0245841 A1 | 9/2015 | Linder et al. |
| 2015/0272567 A1 | 10/2015 | Feezor et al. |
| 2015/0289866 A1 | 10/2015 | Bowen et al. |
| 2016/0066900 A1 | 3/2016 | Brunsvold et al. |
| 2016/0100835 A1 | 4/2016 | Linder et al. |
| 2016/0100933 A1 | 4/2016 | Linder et al. |
| 2016/0174965 A1 | 6/2016 | Brunsvold |
| 2017/0027578 A1 | 2/2017 | Friedman et al. |
| 2017/0056158 A1 | 3/2017 | Saing |
| 2017/0333026 A1 | 11/2017 | Dreyfuss et al. |
| 2018/0078253 A1 | 3/2018 | Kubiak et al. |
| 2018/0200042 A1 | 7/2018 | Kubiak et al. |

OTHER PUBLICATIONS

Momose et al., "Suture Techniques With High Breaking Strength and Low Gliding Resistance: Experiments in The Dog Flexor Digitorum Pofundus Tendon," Acta Orthop Scand, 2001, 72(6):635-641.

Leung et al., "Barbed, Bi-Directional Medical Sutures: Biomechanical Properties and Wound Closure Efficacy Study," Society for Biomaterials 28ths Annual Meeting Transactions, 2002, p. 724.

Chunfeng et al., "Enhancing the Strength of the Tendon-Suture Interface Using 1-Ethyl-3-(3-dimethylaminoproply) Carbodimide Hydrochloride and Cyanoacrylate," Journal of Hand Surger, 2007, 32(5): 606-11.

Burkhead et al., "Use of Graft Jacket as an Augmentation for Massive Rotator Cuff Tears," Semin Arthro, 2007, 18(1): 11-18.

Hirpara et al., "A Barbed Device for Digital Flexor Tendon Repair," http://proceedings.jbjs.org.uk/cgi/content/abstract/92-B/SUPP_II/291-d, Mar. 2010.

(56) References Cited

OTHER PUBLICATIONS

Office Action with English Translation issued in CN 201580066314.4 dated Jun. 22, 2018.
Supplementary European Search Report issued in EP 15850646.9 dated Jun. 25, 2018.
International Search Report dated Feb. 26, 2016 for International Application No. PCT/US2015/56059 (14 pages).
International Search Report dated Jul. 20, 2015 for International Application No. PCT/US2015/020231 (10 pages).
International Search Report dated Oct. 10, 2013 for International Application No. PCT/US2013/052735 (7 pages).
International Search Report dated May 8, 2019 for International Application No. PCT/US2019/018628 (14 pages).
Office Action issued in EP 15850646.9 dated Sep. 19, 2019.

\* cited by examiner

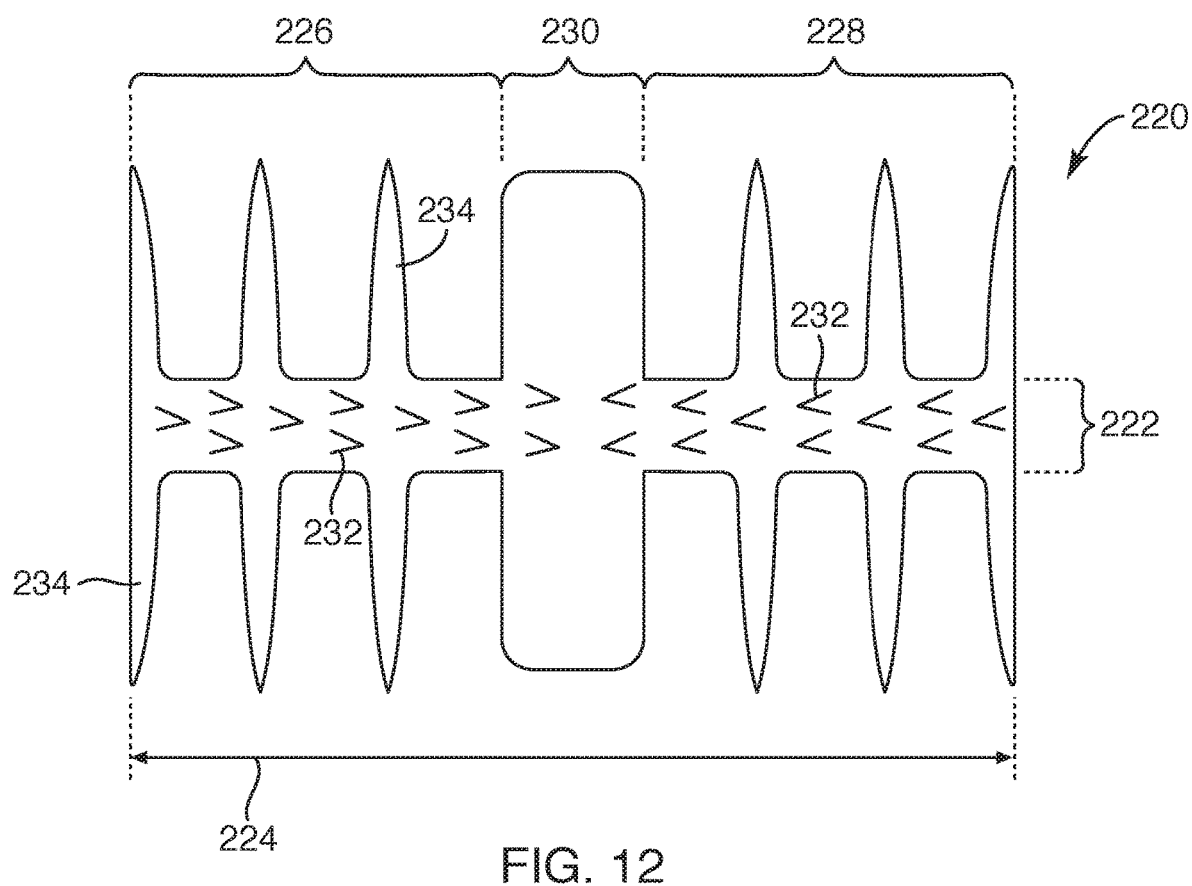
FIG. 12
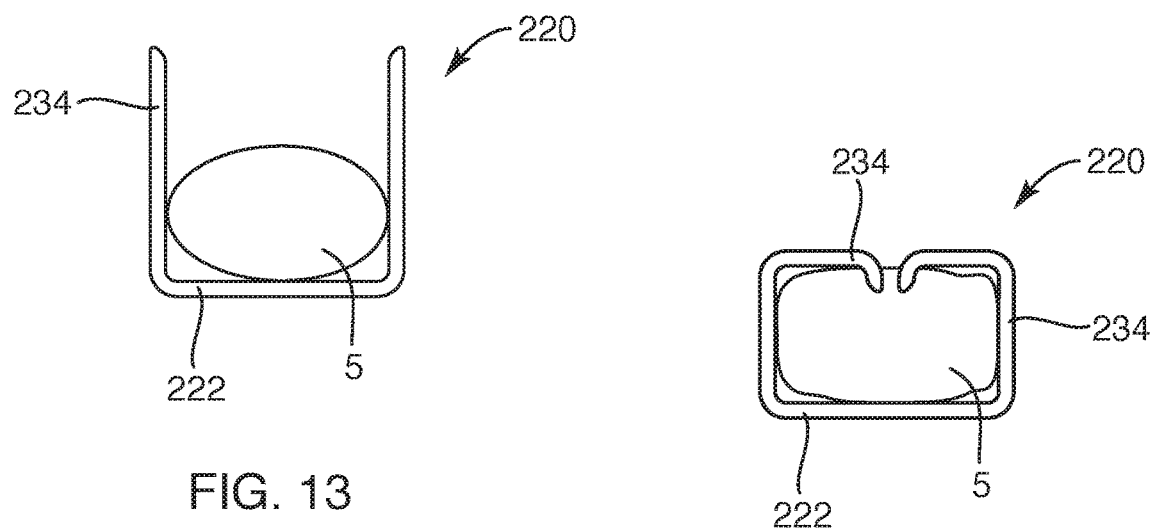
FIG. 13
FIG. 14

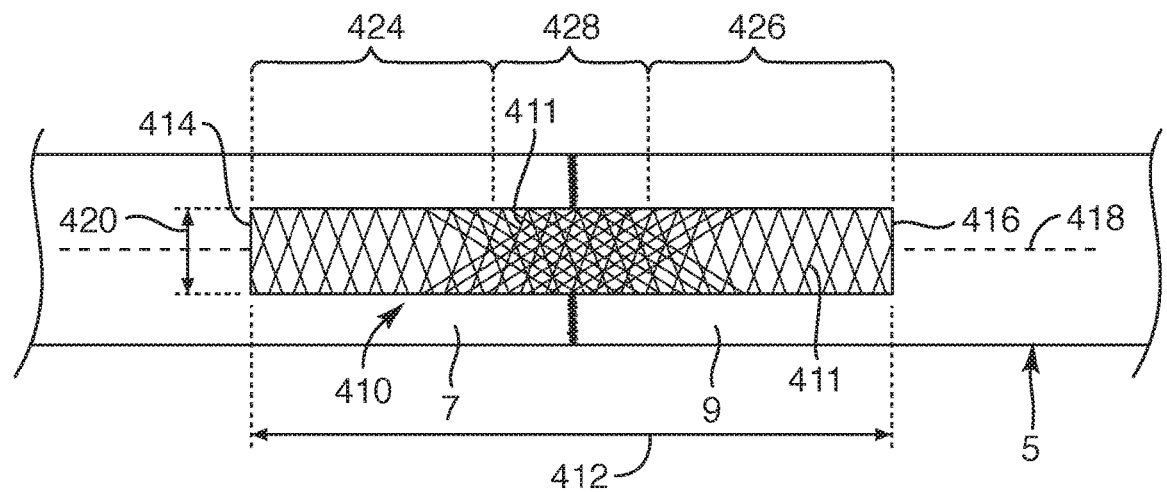
FIG. 32
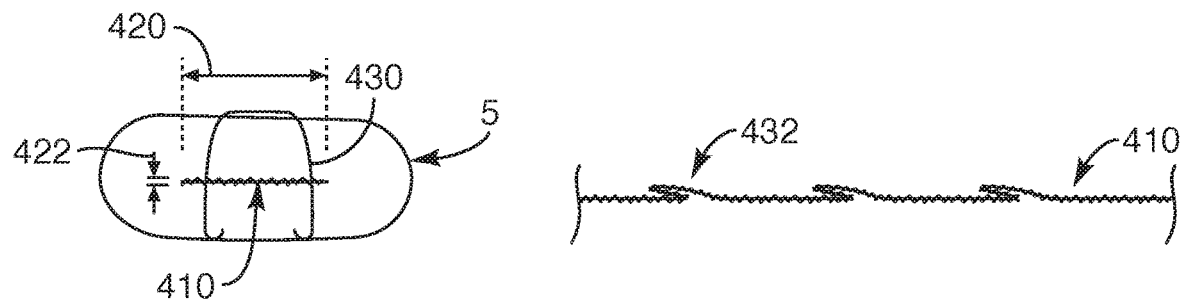
FIG. 33
FIG. 34
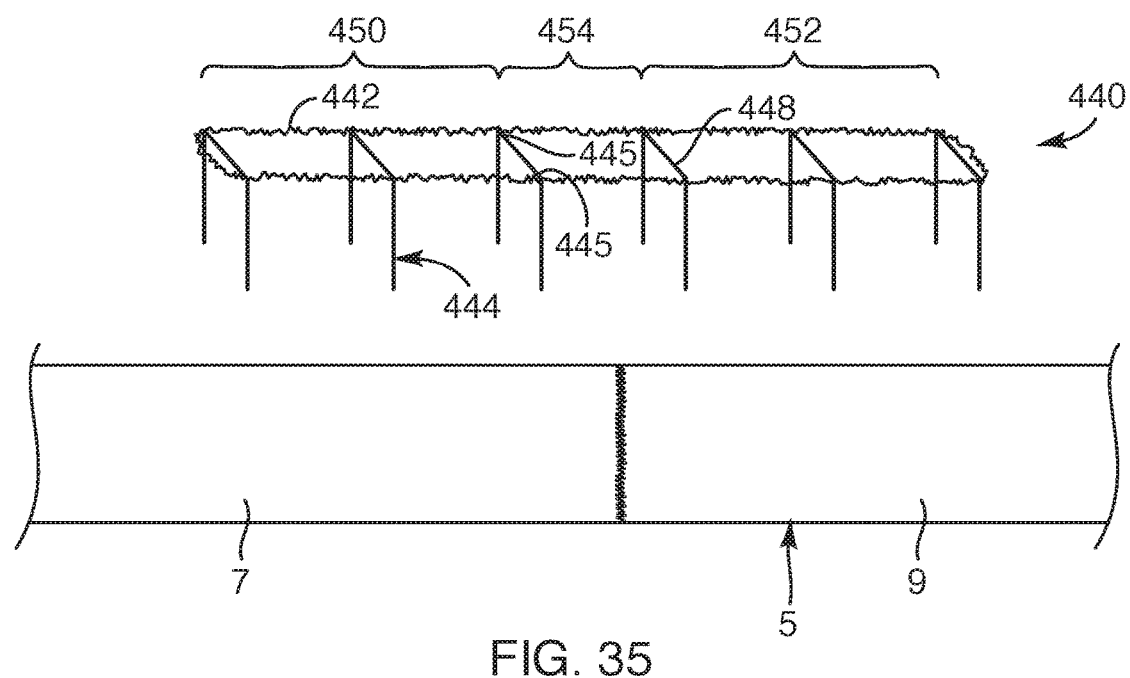
FIG. 35

SOFT TISSUE REPAIR DEVICES, SYSTEMS, AND METHODS

CROSS-REFERENCE TO RELATED APPLICATIONS

The present application is a divisional of U.S. patent application Ser. No. 14/645,924, filed Mar. 12, 2015, now U.S. Pat. No. 9,629,632, which is a continuation-in-part of U.S. patent application Ser. No. 13/953,709, filed Jul. 29, 2013, now U.S. Pat. No. 9,427,309, which claims the benefit of U.S. Provisional Patent Application No. 61/804,570, filed Mar. 22, 2013, and U.S. Provisional Patent Application No. 61/677,239, filed Jul. 30, 2012, the disclosures of each are hereby incorporated by reference herein in their entirety. Further, U.S. patent application Ser. No. 14/645,924 also claims the benefit of U.S. Provisional Patent Application No. 62/053,056, filed Sep. 19, 2014, U.S. Provisional Patent Application No. 62/040,451, filed Aug. 22, 2014, U.S. Provisional Patent Application No. 62/007,783, filed Jun. 4, 2014, and U.S. Provisional Patent Application No. 61/952,114, filed Mar. 12, 2014, the disclosures of each are hereby incorporated by reference herein in their entirety.

TECHNICAL FIELD

The present invention relates generally to repairing a lacerated tendon or ligament. More particularly, the present invention relates to devices, systems, and methods for repairing tendon and/or ligaments at a repair site.

BACKGROUND

Lacerated flexor tendon repair, as an example, is a procedure performed tens-of-thousands of times a year in the United States alone. For all types of tendons in the human anatomy, early post-operative mobilization is beneficial to restoring maximal tendon function following injury and repair. Adhesion formation is a common complication following tendon repair, but can be reduced through motion rehabilitation programs as soon as possible following a surgery. By preventing adhesion formation and gliding resistance, tendon healing may be enhanced. However, the failure rate of tendon repairs is close to 30 percent, primarily because of overloading at the repair site. Although an objective of tendon repair is to provide adequate strength for passive and active motion during rehabilitation, it is important to maintain a delicate balance between rehabilitative motion protocols and fatiguing the repair site.

Typical procedures for lacerated tendon repair use one or more sutures to mend the two ends of a tendon together using complex suture patterns. While this can provide a good initial repair, the strength and quality of the repair may quickly degrade with subsequent loading and mobilization. Although postoperative therapy may be utilized to reduce adhesion, the resulting tension can induce gap formation or tendon rupture at the repair site, seriously impairing the outcome of the repair. Gapping at the repair site has many negative effects, such as reduced repair strength, tendon rupture, and an increased probability for adhesion.

BRIEF SUMMARY OF THE INVENTION

Embodiments of the present invention are directed to various devices, systems and methods for repairing a tendon or ligament in a body. For example, in one embodiment, a medical device system configured to fuse a first tendon end to a second tendon end of a lacerated tendon is provided. The medical device system including a delivery device and a repair device. The delivery device including a body, a handle extending from the body, a trigger associated with the handle, an elongated guide, a cartridge, and a slider member. The elongated guide is operatively coupled to the body, the elongated guide defining a longitudinal guide axis, and the elongated guide including a drive shaft and a pusher block extending along the longitudinal guide axis. The cartridge is removably coupled to an end of the elongated guide. The slider member is slidably coupled to a distal portion of the elongated guide. The slider member includes a cradle portion such that the cradle portion is fixed to the slider member and positioned distal of the slider member. The cradle portion includes an elongated bed surface defining a longitudinal cradle axis, the longitudinal cradle axis being substantially perpendicular to the longitudinal guide axis, the bed surface of the cradle portion configured to receive a first tendon portion and a second tendon portion of the lacerated tendon. The repair device is configured to be positioned within the cartridge. The repair device includes an elongated flexible member and anchors configured to extend through the elongated flexible member. Each of the anchors including a base with legs extending from the base from a proximal end to a distal free end such that the legs from the proximal end to the distal free end extend substantially parallel with the longitudinal guide axis and the elongated flexible member extends substantially perpendicular relative to the longitudinal guide axis.

In one embodiment, upon the lacerated tendon being positioned in the cradle portion, the trigger is actuated to compress the anchors through the lacerated tendon to couple the elongated flexible member to the lacerated tendon. In another embodiment, upon actuation of the trigger, the drive shaft moves distally to push the anchors through the cartridge so that the legs extend through the first and second tendon portions, to then compress against the bed surface so that the legs curl back into a distal side of the first and second tendon portions with the base of each of the anchors coupling the elongated flexible member to a proximal side of the first and second tendon portions. In another embodiment, the bed surface of the cradle portion comprises anvil channels defined therein, the anvil channels sized and configured to receive end portions of the legs of the multiple anchors to curl the end portions and bundle portions of the lacerated tendon.

In another embodiment, the elongated guide includes a spring positioned within the elongated guide and coupled to the slider member, the spring configured to bias the cradle portion toward the cartridge. In a further embodiment, the elongated guide includes a locking mechanism associated with the slider member, the locking mechanism configured to prevent the slider member from movement along the elongated guide.

In still another embodiment, the multiple anchors include a u-shaped configuration. In another embodiment, the elongated flexible member includes a lattice structure. In yet another embodiment, the elongated flexible member includes one or more polymeric filaments. In a further embodiment, the one or more polymeric filaments extend with at least one of a weaved, braided, and knitted configuration. In another embodiment, the multiple anchors are separate and discrete from each other such that the multiple anchors are positioned along a length of the elongated flexible member in at least one of a staggered arrangement and an aligned arrangement.

In another embodiment, the multiple anchors extend from the elongated flexible member along a first portion and a second portion of the elongated flexible member, the elongated flexible member including an intermediate portion extending between the first portion and the second portion of the elongated flexible member. In a further embodiment, upon the lacerated tendon being coupled to the elongated flexible member, the first and second portions of the elongated flexible member are configured to elongate as a force is placed upon the tendon and the intermediate portion of the elongated flexible member is configured to substantially resist elongation of the tendon.

In another embodiment, the delivery device further includes a flexible cable configured to be operatively coupled between the handle and the elongated guide, the flexible cable configured to facilitate remote triggering of the handle relative to the elongated guide. In a further embodiment, the flexible cable is configured to operatively provide a force to the pusher block, the pusher block configured to push the anchors from the cartridge. In another embodiment, the flexible cable is removably coupled to at least one of the elongated guide and the handle. In another embodiment, the delivery device further includes a driving mechanism for driving the anchors from the cartridge, the driving mechanism including at least one of the drive shaft, a cable, a hydraulic mechanism, a pneumatic mechanism, and an electro-mechanical mechanism.

In accordance with another embodiment of the present invention, a repair device configured to fuse first and second ends of a tendon or ligament together is provided. The repair device includes an elongated flat flexible member and multiple anchors. The elongated flat flexible member includes a first portion and a second portion with an intermediate portion between the first and second portions, the first and second portions configured to elongate and the intermediate portion configured to substantially resist elongation, the first and second ends of the tendon or ligament configured to be abutted against each other and positioned adjacent the intermediate portion and first and second end portions of the tendon or ligament are configured to be positioned adjacent and along the respective first and second portions of the elongated flat flexible member. The multiple anchors each having a base with legs extending from the base, the legs of each of the anchors extending from or alongside the elongated flat flexible member. The multiple anchors are configured to couple the first end portion and the second end portion of the tendon or ligament to the respective first and second portions of the elongated flat flexible member such that the first and second ends of the tendon or ligament are fixedly abutted to each other along the intermediate portion of the elongated flat flexible member. With this arrangement, upon the tendon or ligament being coupled to the elongated flat flexible member, the elongated flat flexible member is configured to elongate along a length of the respective first portion and the second portion of the elongated flat flexible member as the first and second end portions of the tendon or ligament elongate, and wherein the intermediate portion substantially resists elongation so as to maintain a substantially fixed position so that the first and second tendon ends fuse together.

In one embodiment, the elongated flat flexible member includes a lattice structure. In a further embodiment, the lattice structure at the intermediate portion extends at a first angle relative to a longitudinal axis of the elongated flat flexible member and the lattice structure at the first and second portions extends at a second angle relative to the longitudinal axis of the elongated flat flexible member, the first angle being smaller than the second angle. In another further embodiment, the lattice structure includes at least one of one or more polymeric filaments and metallic struts.

In another embodiment, the elongated flat flexible member includes one or more polymeric filaments. In a further embodiment, the one or more polymeric filaments extend with at least one of a weaved, braided, and knitted configuration.

In another embodiment, the multiple anchors are separate and discrete from each other, the multiple anchors positioned along a length of the elongated flat flexible member in at least one of a staggered arrangement and an aligned arrangement. In still another embodiment, each of the multiple anchors include a u-shaped configuration. In another embodiment, the at least one of the multiple anchors and the elongated flat flexible member include a bioresorbable material. In yet another embodiment, the elongated flat flexible member includes a monolithic super elastic material.

In another embodiment, the elongated flat flexible member includes multiple pad portions with one or more flexible members extending between each of the multiple pad portions, at least the multiple pad portions of the first and second portions of the elongated flat flexible member are configured to align and couple to at least one of the multiple anchors.

In accordance with another embodiment of the present invention, a method for repairing a lacerated tendon or ligament having a first end and a second end is provided. The method includes: providing a delivery device having a drive shaft defining a drive shaft axis and a removable cartridge positioned distal the drive shaft, the cartridge holding an elongated flat flexible member with multiple anchors coupled to the elongated flat flexible member; positioning a first end portion and a second end portion of the tendon or ligament within an elongated bed surface of a cradle of the delivery device with the first and second ends of the tendon or ligament abutted against each other, the elongated bed surface defining a cradle axis such that the cradle axis is perpendicular to the drive shaft axis; and coupling the elongated flat flexible member with the multiple anchors to the first end portion and the second end portion within the cradle by actuating a trigger of the delivery device so as to actuate the drive shaft distally to effect movement of the anchors and the elongated flat flexible member from the cartridge, through the first and second end portions of the tendon or ligament, and to then compress the anchors against the bed surface of the cradle so that the anchors curl back into the tendon or ligament.

In one embodiment, the method step of positioning includes positioning the first end portion and the second end portion of the tendon or ligament within the cradle so that free ends of legs of the multiple anchors are positioned adjacent the first and second end portions of the tendon or ligament, the legs extending within the cartridge substantially parallel with the drive shaft axis and extending substantially perpendicular with the cradle axis. In another embodiment, the method step of coupling includes compressing the multiple anchors through the first tendon portion and the second tendon portion such that end portions of legs of each of the multiple anchors curl and bundle portions of the tendon or ligament. In another embodiment, the method step of providing includes providing the elongated flat flexible member having a lattice structure such that the multiple anchors are coupled to the lattice structure.

In another embodiment, the method step of providing includes providing the elongated flat flexible member with an elongated length defining a first portion and a second portion with an intermediate portion therebetween, the first and second portions being configured to elongate along the elongated length and the intermediate portion being configured to substantially resist elongation. In a further embodiment, the method step of coupling includes coupling the elongated flat flexible member to the first and second end portions of the tendon or ligament so that the first and second portions of the elongated flat flexible member elongate along the elongated length thereof as the tendon or ligament elongates with the intermediate portion substantially resisting elongation so that the first and second ends of the tendon or ligament fuse together.

In a further embodiment, the method step of providing includes providing the elongated flat flexible member with a lattice structure defining a longitudinal axis defined along the elongated length of the elongated flat flexible member, the lattice structure at the intermediate portion extends at a first angle relative to a longitudinal axis of the elongated flat flexible member and the lattice structure at the first and second portions extends at a second angle relative to the longitudinal axis of the elongated flat flexible member, the first angle being smaller than the second angle. In another embodiment, the method step of providing includes providing the elongated flexible member having at least one of one or more polymeric filaments and a metallic structure.

BRIEF DESCRIPTION OF THE SEVERAL VIEWS OF THE DRAWINGS

The foregoing and other advantages of the invention will become apparent upon reading the following detailed description and upon reference to the drawings in which:

FIG. 12 is a top view of a repair device, depicting the repair device as cut from a flat sheet, according to another embodiment of the present invention;

FIG. 13 is an end view of the repair device of FIG. 12, depicting the repair device in a constrained state with a tendon positioned therein, according to another embodiment of the present invention;

FIG. 14 is an end view of the repair device of FIG. 12, depicting the repair device in a non-constrained state with a tendon positioned therein, according to another embodiment of the present invention;

FIG. 32 is a top view of a flat member positioned within a severed tendon, according to another embodiment of the present invention;

FIG. 33 is a cross-sectional view of the flat member of FIG. 32, depicting a staple or anchor securing the flat member to a tendon, according to the present invention;

FIG. 34 is an enlarged front view of a portion of a flat member, depicting the flat member having crimps and/or folds, according to another embodiment of the present invention;

FIG. 35 is a perspective view of a repair device, according to another embodiment of the present invention;

DETAILED DESCRIPTION OF THE INVENTION

Various embodiments are disclosed herein of a soft tissue repair device. Such repair device may be sized and configured to approximate and fuse, for example, a lacerated tendon. The various embodiments may provide structure that maintains two ends of a lacerated tendon in an abutting relationship, without gapping, while allowing the tendon adjacent the tendon ends and along the length of the repair device to provide controlled elongation of the tendon. In this manner, the repair device of the present invention may provide the proper healing required for fusing the tendon ends while still providing movement of the tendon to minimize atrophy and potential adhesions.

Figure 1:
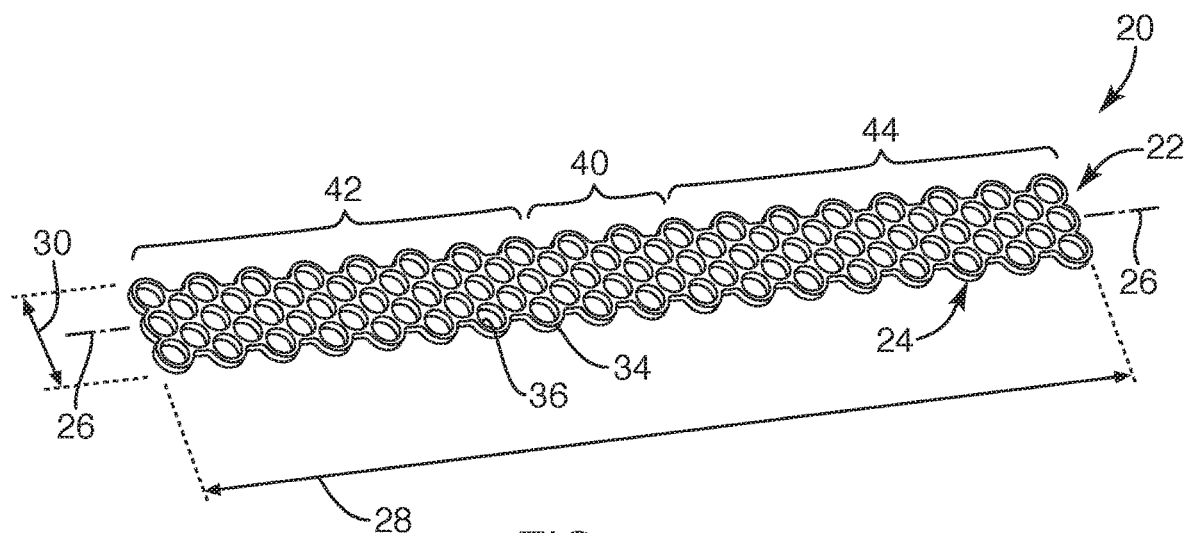
FIG. 1 is a perspective view of an elongated flat member having a lattice structure, according to an embodiment of the present invention.
Figure 2:
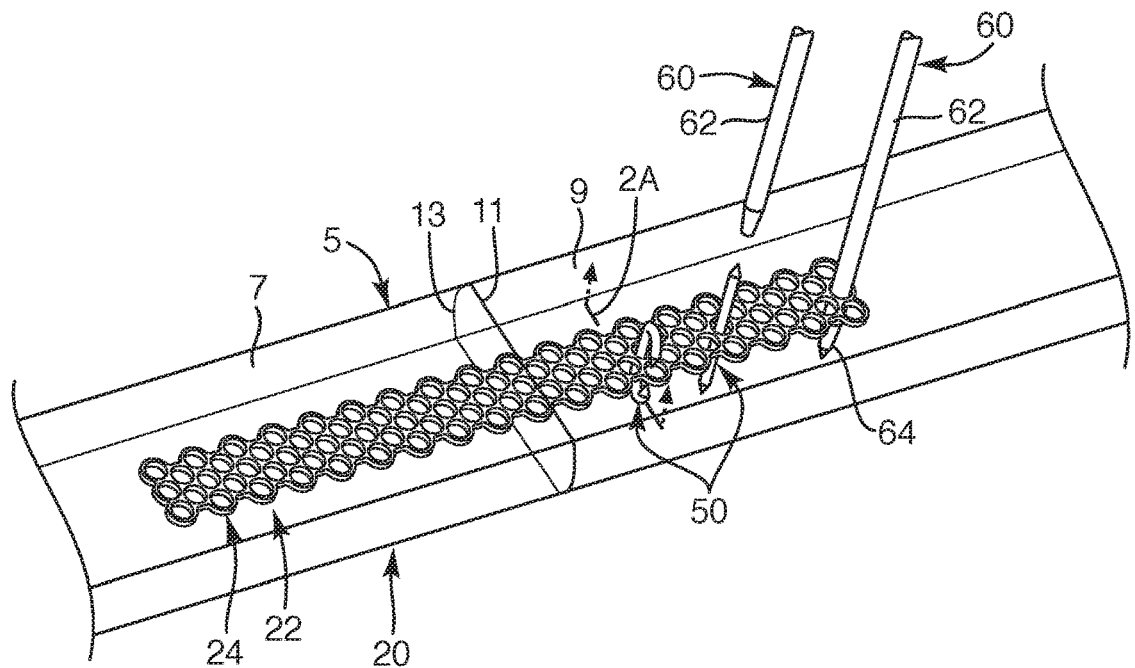
FIG. 2 is a perspective view of the elongated flat member, depicting the flat member positioned within a lacerated tendon with a tool for inserting staples, according to one embodiment of the present invention.
Figure 2A:
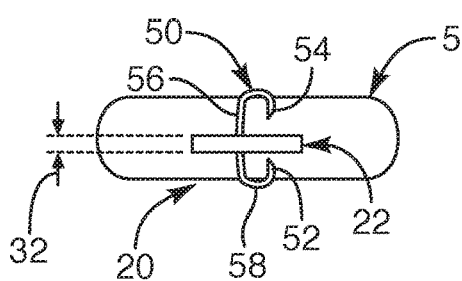
FIG. 2A is a cross-sectional view taken along section 2A of FIG. 2, depicting a staple positioned in the tendon with the flat member, according to another embodiment of the present invention.

Referring to FIGS. 1, 2, and 2A, one embodiment of a repair device 20 for tendon or ligament repair is depicted. With respect to FIG. 1, the repair device 20 may include an elongated flat member 22 that exhibits a lattice structure 24. The elongated flat member may define a longitudinal axis 26 and extend with a longitudinal length 28 and a width 30, which dimensions may provide a generally rectangular shape. Further, such elongated flat member 22 may include a planar or flat configuration that defines a depth 32 (see FIG. 2A).

The lattice structure 24 of the elongated flat member 22 may be a monolithic structure. In one embodiment, the flat member 22 may be a shape memory alloy or a polymeric material. In another embodiment, the elongated flat member 22 may exhibit flexible structural characteristics. In another embodiment, the flat member 22 may be a bioresorbable or bioabsorbable material. In another embodiment, the flat member 22 may be laser cut, for example, from a flat sheet of Nitinol or any other suitable material, such as stainless steel, titanium, combinations thereof, or any other suitable biocompatible material, such as a polymeric material.

The lattice structure 24 may include interconnected struts 34 that define a multi-cellular structure. Such multi-cellular structure or struts define cells 36 or openings extending through the depth 32 of the flat member 22. The struts 34 may be sized and configured uniformly over the length 28 of the flat member 22. In this manner, the cells 36 and struts 34 may be sized similarly over the length 28 of the flat member 22. In another embodiment, the struts 34 may include variations along the length of the flat member 22. Such variations may include tapering along the struts 34. The struts 34 that may be tapered provide strut portions that are more flexible at, for example, the taper than other portions along the strut. In another embodiment, the struts 34 may include angled or arcuate variations along particular struts 34 in the flat member 22 relative to other struts in the flat member. In other words, the struts 34 defining a given cell 36 may extend at angles (or with an arcuate radius) different from the struts 34 defining another cell of the lattice structure 24 to manipulate the behavior of the flat member 22 over various portions of the flat member 22 upon a load being placed thereon. In this manner, the variations within the struts 34 may be sized and configured to facilitate the elongated flat member 22 to stretch or elongate upon an axial load being placed upon the flat member 22 via the tendon becoming loaded. Further, such variations in the struts may facilitate elongation along the length 28 over particular regions. For example, the struts 34 in a middle portion 40 of the flat member 22 may be sized and configured to minimize or substantially resist elongation of the flat member 22 over the middle portion 40. Further, the struts 34 along a first portion 42 and a second portion 44 may be configured to facilitate elongation of the flat member 22 in the axial direction along the first portion 42 and the second portion 44 of the flat member 22. In this manner, the struts 34 and cells 36 over the middle portion 40 may be sized differently than the struts 34 and cells 36 in the first and second portions 42, 44 along the length 28 of the flat member 22.

As depicted in FIGS. 2 and 2A, the elongated flat member 22 may be positioned within a first tendon portion 7 and a second tendon portion 9 of a lacerated tendon 5 such that first and second tendon ends 11, 13 are abutted against each other. The flat member 22 may be positioned by simply inserting about half of the flat member 22 into the first tendon portion 7 and then inserting the other half within the second tendon portion 9. The flat member 22 may be centered and axially aligned with the lacerated tendon 5. Once the flat member 22 is positioned, the flat member 22 may be secured to the lacerated tendon 5 with multiple staples 50 extending through the tendon 5 and the flat member 22.

The staples 50 may be introduced, for example, with a needle instrument 60. The needle instrument 60 may include a tubular introducer 62 with a pointed tip 64. The staples 50 may be consecutively aligned within a lumen of the tubular introducer 62 and may be deployed therefrom with a pusher member (not shown). The staples 50 may be formed of a shape memory alloy or polymeric material and may be moveable from a first position to a second position. The first position may be a constrained state and may exhibit a straight, elongated configuration, similar to a straight wire. The staple 50 may extend between a first end 52 and a second end 54, each end having a sharpened point or barb or the like. The second position may be a non-constrained state or relaxed state and may be in the form of a c-shape or the like. The staple may be self-expandable from the first position to the second position.

FIG. 2 depicts various stages for introducing the staples 50 through the flat member 22. For example, the needle introducer 60 with its pointed tip 64 may be positioned over, for example, the second tendon portion 9 and pushed into the tendon and through a cell 36 of the flat member 22 to the opposite side of the second tendon portion 9. At this stage, as depicted to the left of the inserted needle instrument 60, the tubular introducer 62 may be withdrawn while maintaining the position of the pusher member such that the staple 50 may be deployed and left extending through the flat member 22. The staple 50 is depicted in the first position or constrained position (straight position) as the staple would be positioned within the needle instrument 60. However, as the staple 50 is deployed, the staple may automatically self-expand from the first position to the second position, as depicted in its c-shaped configuration, depicted to the left of the staple 50 in its straight position and also shown in FIG. 2A. In this manner, multiple staples 50 may be positioned through the cells of the flat member 22 along the length 28 of the flat member 22. Such staples 50 may be positioned along the length 28 in a staggered arrangement, a linear arrangement, or through particular portions along the length, such as at the middle portion 40 and the first and second portions 42, 44 of the flat member 22.

With reference again to FIGS. 2 and 2A, the staple 50 is depicted in the non-constrained position or c-shaped position. In this position, the staple 50 may be engaged with the tendon 5 and engaged with the flat member 22. The staple 50 may include a mid-section 56 and oppositely extending curved portions 58 to provide, for example, the c-shaped configuration. The mid-section 56 may be configured to extend through a cell 36 and the depth 32 of the flat member 22 while the curved portions 58 may be exposed at opposite sides of the tendon 5. Further, the curved portions 58 may extend back into the tendon 5 with the barb or point extending inward and engaged with the tendon 5.

As set forth, the staples 50 of this embodiment may be made from a shape memory material configured to self-expand from the first constrained position to the second non-constrained position. As such, the staples 50 may be formed of a super elastic material, such as a shape memory metal or a polymer. The metal or alloy may be Nitinol or any other alloy that includes shape memory characteristics. The staples 50 may be heat-set into the c-shaped configuration employing heat setting techniques as known to one of ordinary skill in the art. In the case of a polymer material, it is contemplated to use a bioresorbable material or bioabsorbable material or any other general bio-compatible polymer for both the flat member 22 and the staples 50, or even a shape-memory polymer.

Figure 3:
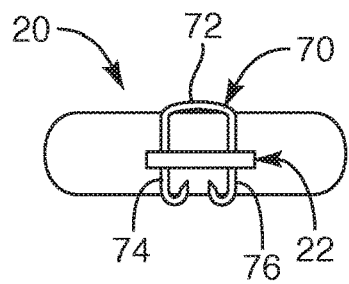
FIG. 3 is a cross-sectional view of the tendon and flat member of FIG. 2, depicting another embodiment of a staple, according to another embodiment of the present invention.

Referring to FIG. 3, another embodiment of one or more staples 70 that may be employed with the flat member 22 is provided. In this embodiment, the staple 70 may be u-shaped. The staple may include a mid-section 72 or base and a first extension 74 and a second extension 76. The mid-section 72, upon inserting the staple 70 through the tendon 5 and the flat member 22, may be exposed on one side of the tendon 5. The first and second extensions 74, 76 may extend through two different openings or cells 36 defined in the flat member 22 or lattice structure and extend to an opposite side of the tendon 5. At the opposite side of the tendon 5, the first and second extensions 74, 76 may be bent toward each other and be exposed on the opposite side of the tendon 5. Such extensions of the staples 70 may bend toward each other utilizing a staple tool (not shown) sized and configured for employing the staples 70 of this embodiment to secure the tendon 5 to the flat member 22. In this embodiment, the staple 70 may be formed of a metallic material or a polymeric material. The metallic material may be stainless steel, titanium, or any other suitable biocompatible metallic material, such as bioresorbable materials, which may include a magnesium material or the like. The polymeric material may be any suitable polymeric material, such as a bioresorbable or bioabsorbable polymeric materials or any other suitable polymeric material, as known in the art.

Figure 4:
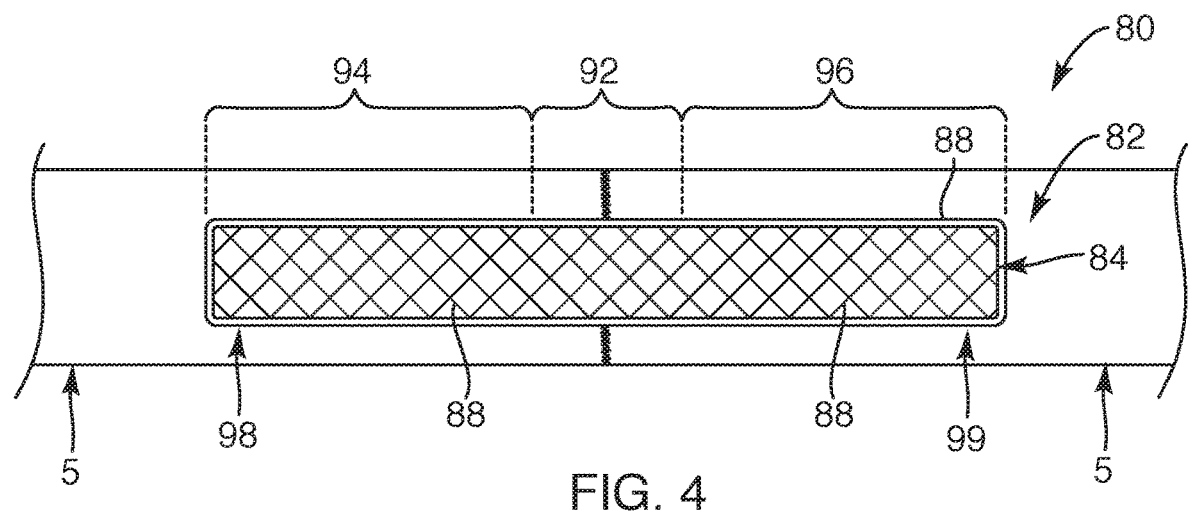
FIG. 4 is a top view of another embodiment of an elongated flat member, according to the present invention.
Figure 5:
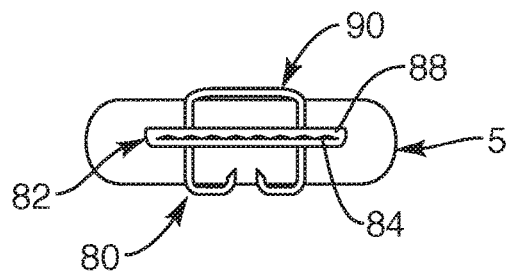
FIG. 5 is a cross-sectional view of the flat member of FIG. 4 positioned in a tendon and secured with staples, according to another embodiment of the present invention.

Now with reference to FIGS. 4 and 5, another embodiment of a repair device 80 including a flat member 82 that may include flexible structural characteristics and that may be secured to, for example, a tendon 5 or ligament with staples 90 or anchors is provided. In this embodiment, the flat member 82 may include similar structural features as the previous embodiment. The flat member 80 may include a lattice structure 84 or the like. The lattice structure 84 may include one or more filaments 86, the one or more filaments intertwined together in at least one of a weaved, knitted, and a braided arrangement or configuration. The one or more filaments 86 may be a fibrous polymeric material or a cotton fibrous material or combinations thereof. The filaments may also be formed from various metallic materials, such as a super elastic material, such as Nitinol. In one embodiment, the lattice structure 84 formed of filaments 86 may include a covering 88 such that the lattice structure 84 may be encapsulated with a polymeric material or, in another embodiment, the lattice structure 84 may be sandwiched or reinforced between two thin films or sheets of polymeric material, such as silicon and, for example, heat pressed together.

The flat member 82 may be inserted within the tendon 5 or ligament in a similar manner as the previous embodiment. Upon inserting the flat member 82 within a lacerated tendon 5, the staples 90 may be placed through a mid-portion 92 of the flat member 82 and through first and second portions 94, 96 of the flat member 82. For example, one or more staples 90 may be placed in the mid-portion 92 to stabilize the tendon ends relative to the mid-portion 92 of the flat member 82. Further, one or more staples 90 may be placed, for example, through a first end portion 98 and a second end portion 99 of the respective first and second portions 94, 96 of the flat member 82. With this arrangement, the flat member 82 may elongate between the staples 90 positioned through the first end portion 98 and the mid-portion 92 of the flat member 82 as a load is placed upon the tendon 5. Likewise, the flat member 82 may elongate between the staples 90 positioned through the second end portion 99 and the mid-portion 92 of the flat member 82 as the load is placed on the tendon 5. As shown in FIG. 5, the staples 90 may include a u-shaped configuration and include similar structural characteristics as that set forth relative to FIG. 3. In another embodiment, the staples 90 employed with the flat member 82 of FIG. 4 may be self-expandable staples similar to that depicted in FIG. 2A.

Figure 6:
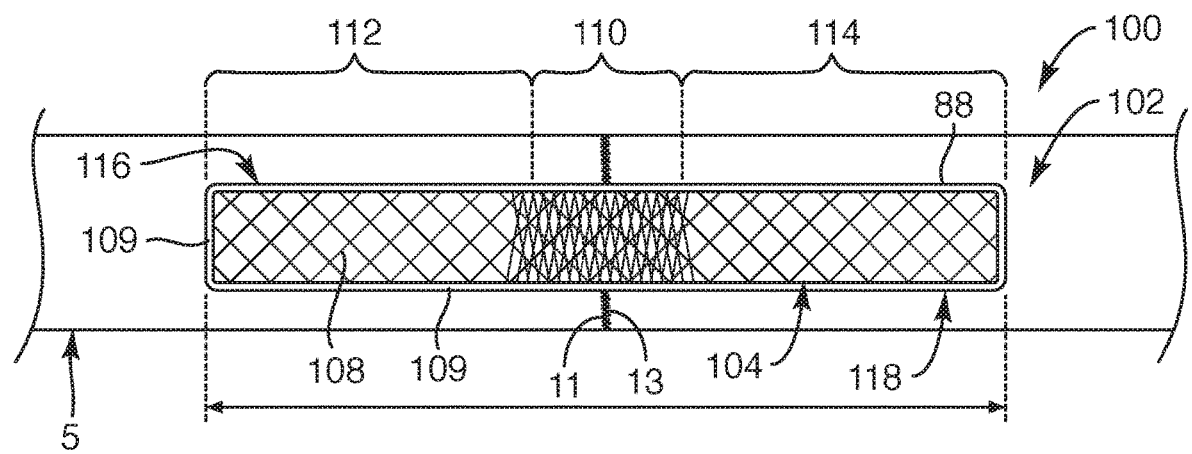
FIG. 6 is a top view of another embodiment of an elongated flat member, depicting a mid-portion of the flat member having a different structure than other portions thereof, according to the present invention.

With reference to FIG. 6, another embodiment of a repair device 100 including a flat member 102 that may be elongated and that may include flexible structural characteristics is provided. This embodiment may be similar to the previous embodiment, except the lattice structure 104 itself may include variations along a length 106 of the flat member 102. As in the previous embodiment, the flat member 102 may include one or more filaments 108 that may also include a covering 109 of reinforced silicon or the like, the filaments 108 intertwined together in a weaved, knitted, and/or a braided arrangement. In this embodiment, the weave, knit, and/or braided arrangement may be tighter, denser, thicker, or include additional strands over, for example, a mid-portion 110 of the flat member 102 relative to the first portion 112 and the second portion 114 of the flat member 102. Otherwise said, the first and second portions 112, 114 of the flat member 102 may include looser, less dense, or less strands along the length of the flat member in comparison to that provided in the mid-portion 110 of the flat member 102. In another embodiment, the durometer of the strands may be harder or stiffer over the mid-portion 110 of the flat member 102 as compared to the durometer of the strands or filaments 108 extending over the first and second portions 112, 114 of the flat member 102. In another embodiment, the diameter or thickness of the strands or filaments 108 may be larger over the mid-portion 110 as compared to the diameter of the strands or filaments 108 extending over the first and second portions 112, 114 of the flat member 102.

Similar to the previous embodiment, one or more staples 90 (similar to that shown in FIG. 5) may be inserted through the flat member 102 at the mid-portion 110 as well as over the first and second portions 112, 114 of the flat member 102. Further, similar to the previous embodiment, such one or more staples 90 may be positioned at the first end portion 116 and the second end portion 118 so that the flat member 102 may elongate along its length between the inserted staples 90 at their relative first and second portions 112, 114 of the flat member 102 as a load in placed upon the tendon while maintaining the lacerated first and second tendon ends 11, 13 fixed and abutted together.

Figures 7, 7A, 8, 9:
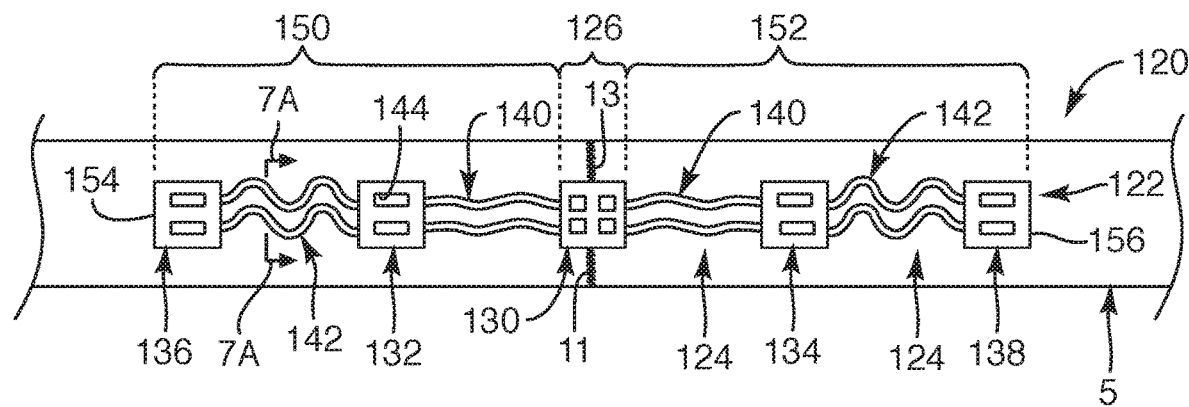
FIG. 7 is a top view of another embodiment of an elongated flat member, depicting the flat member having multiple pads with flexible members therebetween, according to the present invention.
FIG. 7A is a cross-sectional view taken along section 7A of FIG. 7, depicting the flexible members having a flat structure, according to another embodiment of the present invention.
FIG. 8 is a cross-sectional view of the flat member of FIG. 7 positioned within a tendon and secured with staples at one of the pads, according to another embodiment of the present invention.
FIG. 9 is a top view of another embodiment of the an elongated flat member, depicting the flat member having multiple pads with a lattice structure and flexible members therebetween, according to the present invention.

Now with refer to FIGS. 7, 7A, and 8, another embodiment of a repair device 120 including a flat member 122 sized and configured to be inserted within lacerated ends of a tendon 5 and stapled thereto is provided. In this embodiment, the flat member 122 may include flexible structural characteristics. The flat member 122 of this embodiment may be sized and configured to elongate via flexible members 124 therealong so that the flat member 122 may elongate with defined distances over particular portions of the flat member 122 with a mid-portion 126 configured to be rigid, without elongation or with minimized elongation.

In one embodiment, the flat member 122 may include multiple pads 125 sized and configured to receive one or more staples 148 or anchors. The multiple pads 125 may be aligned to form an elongate flat member 122 and may include one or more flexible members 124 therebetween. Each of the pads 125 and flexible members 124 may exhibit a monolithic flat structure having a substantially common thickness or depth 128. Further, the flat member 122 may include a mid-pad 130, a first pad 132, a second pad 134, a third pad 136, and a fourth pad 138, each with the one or more flexible members 124 extending between respective pads 125. For example, the mid-pad 130 may be positioned between the first pad 132 and the second pad 134. The first pad 132 may be positioned between the third pad 136 and the mid-pad 130. Similarly, the second pad 134 may be positioned between the mid-pad 130 and the fourth pad 138.

The mid-pad 130 may include one or more flexible members 124 extending from opposite sides thereof to the respective first pad 132 and the second pad 134. Such one or more flexible members 124 extending from the mid-pad 130 may include a first flexible configuration 140. The first pad 132 may also include one or more flexible members 124 extending therefrom to the third pad 136, which may include a second flexible configuration 142. Likewise, the second pad 134 may include one or more flexible members 124 extending therefrom to the fourth pad 138, which one or more flexible members 124 may include the second flexible configuration 142. With this arrangement, the second flexible configuration 142 may flex and elongate to a greater degree than the first flexible configuration 140.

Each of the pads 125 may be sized and configured to receive one or more staples 148 or anchors. For example, the mid-pad 130 may receive two staples 148 while the other pads may receive a single staple 148, but also may be configured to receive additional staples. In another embodiment, the mid-pad 130 may not receive any staples 148. Each of the pads 125 may be a rigid flat portion with openings 144 defined therein that may be sized and configured to receive the staples 148, except the mid-pad 130 may not receive the staples 148. The rigid flat portions may include a square or rectangular shape, the corners of which may be rounded.

In one embodiment, the flat member 122, similar to the previous embodiments, may be inserted or positioned within lacerated ends of a tendon 5 or ligament with the first and second tendon ends 11, 13 positioned over the mid-pad 130 and abutted against each other. One or more staples 148 may be inserted through the tendon 5 and the mid-pad 130 adjacent the first and second tendon ends 11, 13 while also ensuring that the tendon ends 11, 13 maintain an abutted relationship. One or more staples 148 may then be inserted through, for example, the tendon 5 and through the first pad 132. Likewise, one or more staples 148 may be inserted in a similar manner through each of the second pad 134, the third pad 136 and the fourth pad 138. Upon a load being placed on the tendon 5, subsequent to the surgery, the flexible members 124 may elongate and flex between the pads 125 while the mid-pad 130 is substantially rigid to maintain the abutted tendon ends 11, 13 against each other to facilitate proper fusion of the lacerated tendon 5. Further, the flexible members 124 having the first flexible configuration 140, adjacent the mid-pad 130, provide minimal elongation to ensure the tendon ends 11, 13 have minimal load placed thereon. The flexible members 124 having the second flexible configuration 142 may be configured to elongate further then the first flexible configuration 140, thereby, allowing for the tendon 5 to elongate there along as a load is placed on the tendon 5. Such elongation of the flat member 122 over particular portions thereof facilitates greater healing efficiency in the lacerated tendon 5 as the tendon may still be used and receive loads placed thereon while maintaining the tendon ends 11, 13 abutted against each other.

Similar to the previous embodiments, the flat member 122 of this embodiment includes a first portion 150 and a second portion 152 with the mid-portion 126 therebetween. The first portion 150 and the second portion 152 may elongate while the mid-portion 126 is substantially rigid to substantially resist elongation. However, as set forth above, the first and second portions 150, 152 of this embodiment includes flexible members 124 having the first and second flexible configurations 140, 142 with different elongation structural characteristics. Thus, the elongation characteristics of the flat member 122 become greater from the mid-portion 126 toward opposite first and second ends 154, 156 of the flat member 122.

In another embodiment, the flat member 122 may be minimized in the number of pads 125 employed. For example, the flat member 122 may include the mid-pad 130 positioned between the first pad 132 and the second pad 134 such that the first and second pads 132, 134 may be the opposite ends of the flat member 122. The flexible members 124 extending from the mid-pad 130 to the respective first and second pads 132, 134 may include a similar or common flexible configuration such that such flexible configuration for each of the flexible members 124 may elongate a similar distance. In this manner, the lacerated tendon ends 11, 13 may be fixed to the mid-pad 130 for proper fusion while the remaining portions of the flat member 122 may facilitate controlled elongation of the tendon 5 to minimize the load placed on the tendon ends 11, 13 while still allowing the tendon 5 to become stressed and exercised to effect proper healing of the tendon.

With reference now to FIG. 9, another embodiment of a repair device 160 including a flat member 162, similar to the embodiment of FIG. 7, is provided. In this embodiment, the pads 164 may each include a lattice structure 166 defining openings 168 therethrough. Such lattice structure 166 may be sized and configured to provide structural rigidity in the pads 164 while also providing openings 168 therethrough to readily be able to insert staples (not shown) for attaching to the tendon 5. In other words, having the lattice structure 166 may limit error upon securing the flat member 162 to the tendon 5 as anyone of the openings 168 defined in a particular pad 164 may receive a staple.

As in the previous embodiment, the flat member 162 may include one or more flexible members 170 with a first flexible configuration 172 and a second flexible configuration 174, the second flexible configuration 174 configured to elongate (with more flexibility) than the first flexible configuration 172. As such, the first flexible configuration 172 of the one or more flexible members 170 may extend from opposite sides of the mid-pad 176 to the respective first pad 178 and second pad 180. Similarly, the second flexible configuration 174 of the one or more flexible members 170 may extend from the first pad 178 and the second pad 180 to the third pad 182 and the fourth pad 184, respectively. In another embodiment, the mid-pad 176 may include a solid, rigid structure (but for openings to receive the staples) similar to the mid-pad shown in FIG. 7, with the remaining first pad 178, second pad 180, third pad 182, and fourth pad 184 exhibiting the lattice structure 166.

The embodiments of the flat member 122, 162 depicted in FIGS. 7 through 9 may be formed from any suitable biocompatible material, such as a metallic or polymeric material. For example, the flat member may be laser cut from a flat sheet of shape memory material or super-elastic material, such as Nitinol or the like, with the staples made from shape memory material or stainless steel or any other biocompatible metallic material, similar to other described anchors/staples described herein. In another embodiment, the flat member 122, 162 and staples may also be formed from a polymeric material, such as a bioresorbable material, or any other suitable polymeric material.

Figure 10:
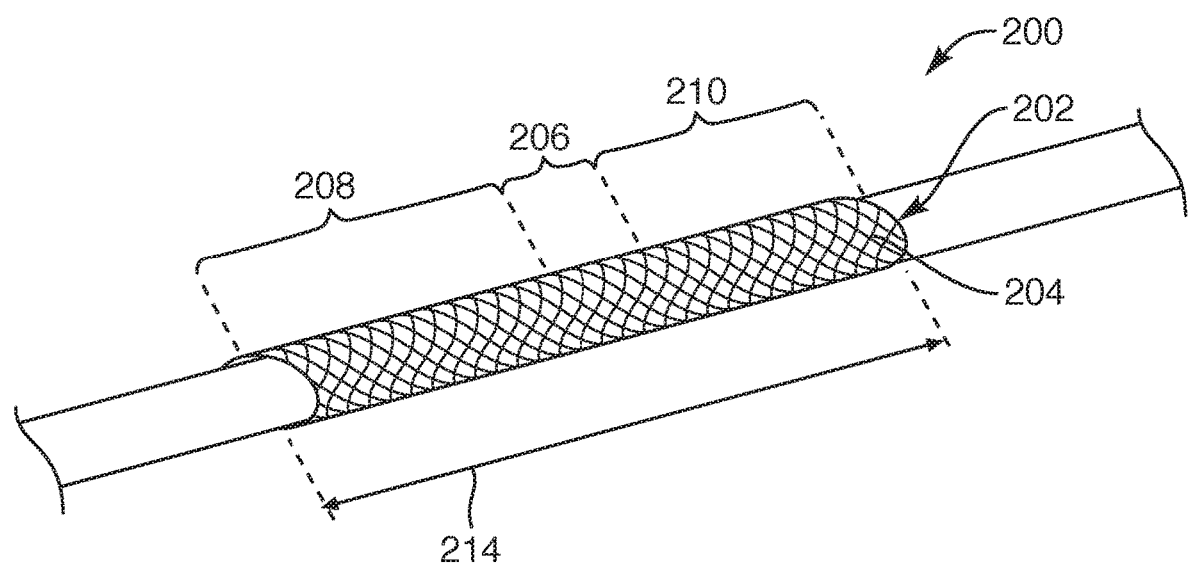
FIG. 10 is a perspective view of an elongated member, depicting the elongated member over a lacerated tendon, according to another embodiment of the present invention.
Figure 11:
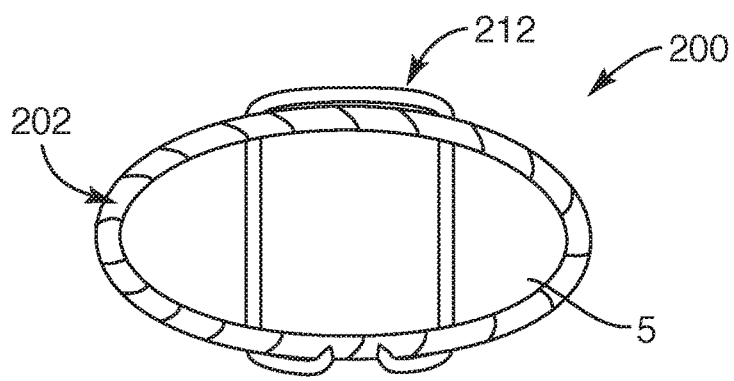
FIG. 11 is a cross-sectional view of the tubular member of FIG. 10, depicting the elongated member surrounding the tendon, according to another embodiment of the present invention.
Figure 15:
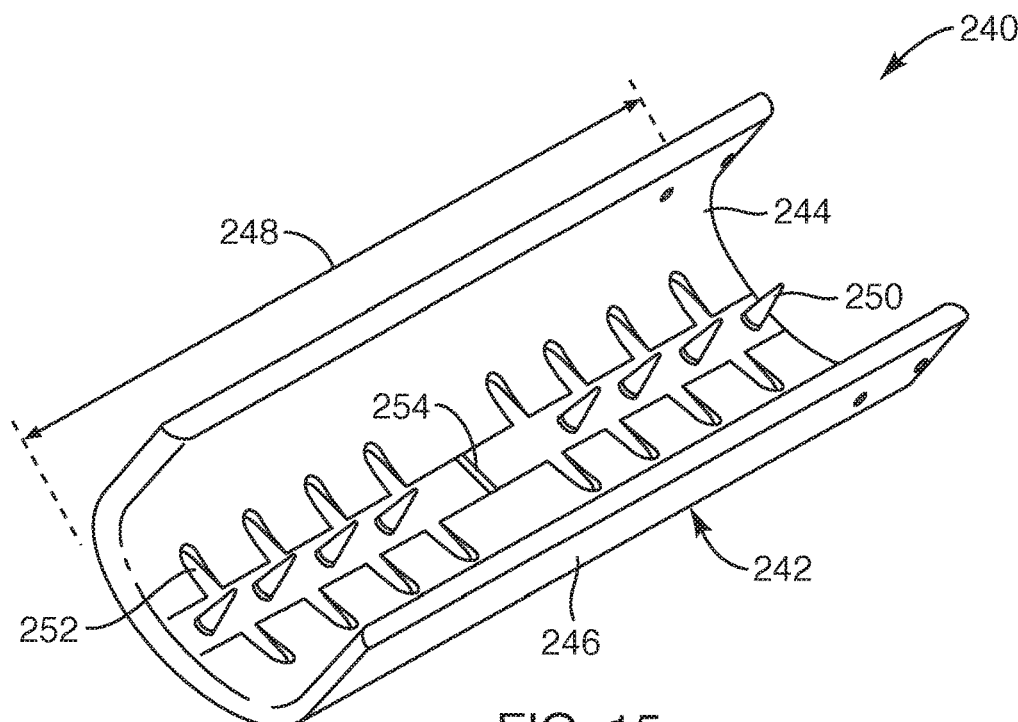
FIG. 15 is a perspective view of a cradle as a portion of a tool, according to one embodiment of the present invention.

With reference to FIGS. 10 and 11, another embodiment of a repair device 200 is provided. In this embodiment, the repair device 200 may be a tubular member 202 and sized and configured to be positioned around the outside of a lacerated tendon 5. The tubular member 202 may be formed with multiple filaments 204 weaved and/or braided together in a tubular configuration. Similar to previous embodiments, the tubular member 202 may include a mid-portion 206 and first and second portions 208, 210. The mid-portion 206 of the tubular member 202 may be stiffer, may include additional filaments 204, or the filaments may include a greater diameter than the first and second portions 208, 210 of the tubular member 202. As in previous embodiments, the mid portion 206 of the repair device 200 may be configured to be positioned over and adjacent to the first and second tendon ends. Once the repair device 200 is properly positioned over the lacerated tendon 5, staples 212 may be inserted through the tubular member 202 and through the tendon 5 at the mid portion 206 of the tubular member 202. Additional staples 212 may be inserted along the first and second portions 208, 210 of the repair device 200, such as adjacent first and second ends of the tubular member 200. With this arrangement, the mid-portion 206 of the tubular member 202 maintains the first and second tendon ends abutted against each other while the first and second portions 208, 210 of the repair device 200 may elongate along a longitudinal length 214 thereof as a load is placed upon the tendon 5. The repair device 200 of this embodiment may be formed of a metallic material, such as a shape memory alloy. In another embodiment, the repair device 200 may be formed from a polymeric material, such as a bioresorbable material, or any suitable polymeric material. As in previous embodiments, the staples may be formed of a metallic or polymeric material. In one embodiment, the staples may be metallic or polymeric bioresorbable materials.

With reference to FIGS. 12-14, another embodiment of a repair device 220 is provided. In this embodiment, the repair device 220 may wrap around a lacerated tendon 5. FIG. 12 depicts the repair device 220 as cut from a flat sheet, such as a flat sheet of Nitinol. FIG. 13 depicts an end view of the repair device 220 in a constrained position, being constrained by an applicator (not shown). FIG. 14 depicts an end view of the repair device 220 in a non-constrained position with the applicator removed such that the repair device 220 automatically wraps around the tendon 5.

With respect to FIGS. 12-14, the repair device 220 of this embodiment may include a base portion 222 that extends along a longitudinal length 224 of the device. The base portion 222 may include a first portion 226 and a second portion 228 with a mid-portion 230 therebetween. Further, the base portion 226 may include tines 232 extending from a surface of the base portion 222 along the longitudinal length 224 thereof such that the tines 232 extend inward toward the mid-portion 230 from both the first and second portions 226, 228 of the base portion 222. The first and second portions 226, 228 may also include multiple laterally extending extensions 234, each extending from opposite lateral sides of the base portion 222. The repair device 220 may be heat-set in the configuration depicted in FIG. 14 so that the repair device 220 can be moved to the first constrained position (shown in FIG. 13) with an applicator (not shown) and, upon the applicator being removed, the repair device 220 may automatically move to the heat-set configuration or wrapped configuration.

The repair device 220 may be implanted by first holding the device in the first constrained position, as depicted in FIG. 13. In this position, the lacerated tendon 5 may be placed within an upper open end of the repair device 220 with first and second tendon ends positioned over the mid-portion 230 of the device in an abutted arrangement. Once the lacerated tendon 5 is properly positioned over the base portion 222 of the device, the applicator (not shown) may be removed to allow the mid-portion 230 and extensions 234 to wrap over the lacerated tendon 5 and close-off its upper open end. The tendon 5 may maintain its position relative to the device via the tines 232 and the extensions 234 over the tendon. The extensions 234 may also include tines extending therefrom to maintain the tendon 5 in its proper position.

Now referring to FIGS. 15 through 20, a tool 240 for inserting and securing any one of the flat members, set forth in FIGS. 1, 4, 6, 7, and 8, to a lacerated tendon 5 is provided. With respect to FIG. 15, the tool 240 may include a cradle 242. The cradle may include an interior surface 244 and an exterior surface 246. The cradle 242 may be elongated with a length 248 to define a cradle axis and may extend along the length with a u-shaped lateral cross-section. The cradle 242 may include tines 250 extending upward along the length 248 from the interior surface 244. Such tines 250 may be linearly aligned along the length 248 and may be centrally aligned along the length 248. Further, the tines 250 may extend substantially perpendicular relative to a bottom of the interior surface 244. In another embodiment, the tines 250 may be angled toward a mid-point 254 of the interior surface. Furthermore, the interior surface 244 may define multiple grooves 252 (or otherwise referred to as recesses or channels) defined therein. Such grooves 252 may be sized and configured to receive and engage with staples (not shown) so as to act as an anvil bucket, discussed in more detail hereafter.

Figure 16:
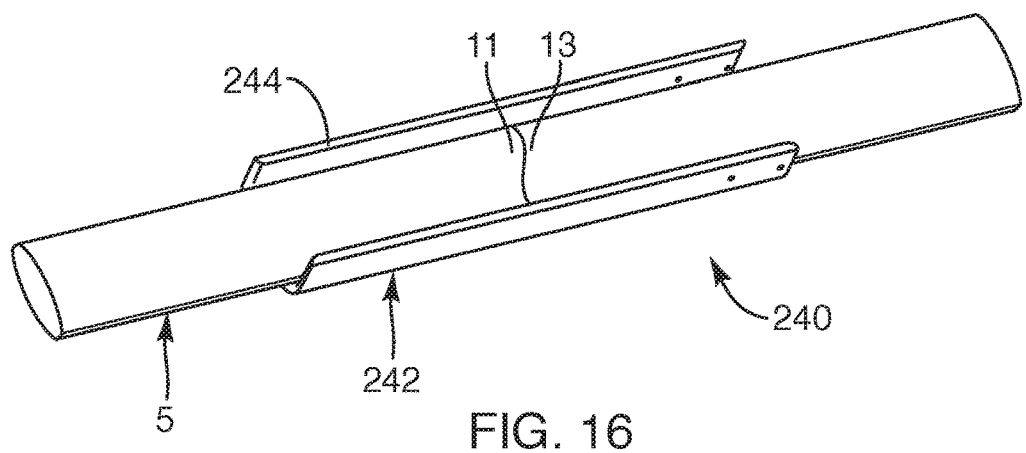
FIG. 16 is a perspective view of the cradle, depicting a lacerated tendon positioned therein, according to another embodiment of the present invention.
Figure 17:
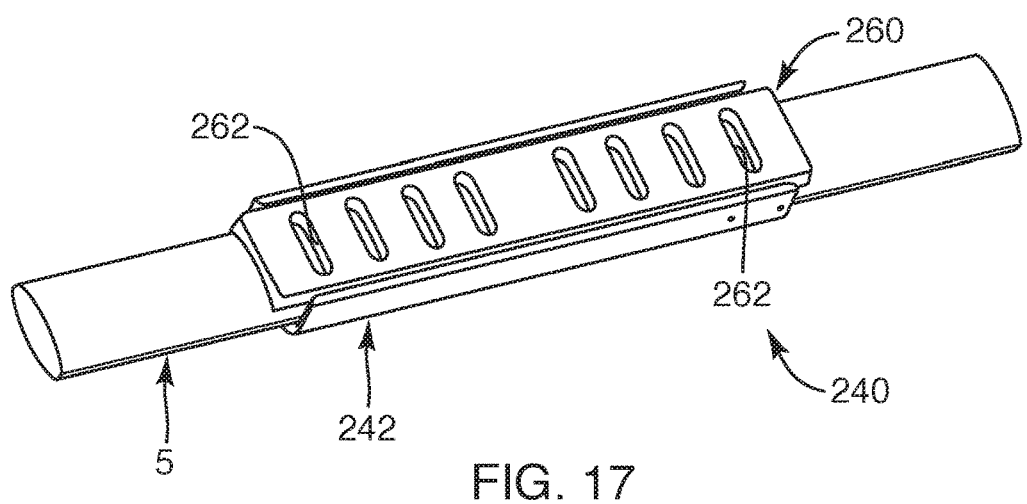
FIG. 17 is a perspective view of the tool with the cradle and an anchor guide, depicting the tool with a lacerated tendon therein, according to another embodiment of the present invention.

As shown in FIG. 16, the cradle 242 may be sized and configured to receive a lacerated tendon 5 or ligament. The first and second tendon ends 11, 13 of the lacerated tendon 5 may be positioned over the mid-point 254 of the cradle 242 such that the interior surface 244 of the cradle 242 substantially surrounds a portion of the lacerated tendon 5. Further, the tendon 5 may be positioned in the cradle 242 such that the tines 250 (FIG. 15) may maintain the tendon 5 in its position within the cradle 242. With respect to FIG. 17, upon the tendon 5 being positioned within the cradle 242, a staple guide 260 or cover may then be positioned over the cradle 242 to enclose and engage an upper side of the cradle 242.

The staple guide 260 may be elongated and include a flat configuration with a similar length of the cradle 242 and may be sized to fit snug over the tendon 5 in a fixed manner, via notches, protrusions, and/or grooves along the cradle 242 and sides of the staple guide 260. The staple guide 260 may be employed to assist in managing the position of the tendon 5 in the cradle 242. Such staple guide 260 may include slots 262 defined therein that extend laterally relative to the length 248 of the cradle 242. Such slots 262 may be sized and configured to receive staples (not shown) therethrough. The slots 262 may be spaced from each other and may correspond with the grooves 252 (FIG. 15) defined in the cradle 242. The staple guide 260 may also include tines 264 (see FIG. 19) configured to extend downward into the tendon 5 so as to stabilize and position the tendon 5 relative to the cradle 242.

Figure 18:
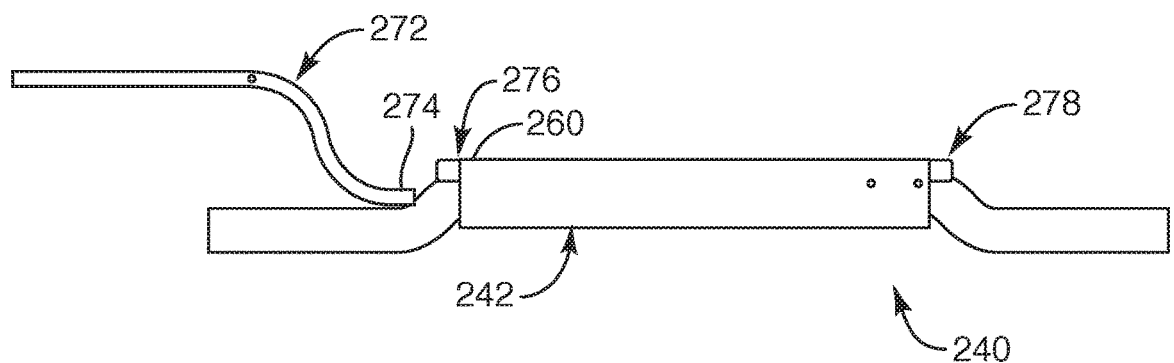
FIG. 18 is a side view of the tool with a tendon therein, depicting an insert guide positioned against the tendon and adjacent one side of the tool, according to another embodiment of the present invention.
Figure 19:
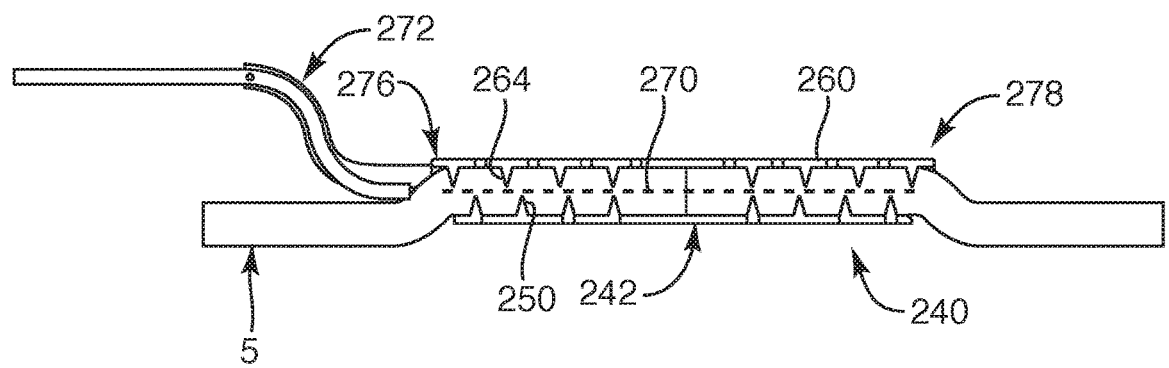
FIG. 19 is a side view of the tool with a tendon therein, depicting a flat member being deployed from the insert guide and within the tendon, according to another embodiment of the present invention.

With respect to FIGS. 18-19, upon the lacerated tendon 5 or ligament being placed within the cradle 242 and the staple guide 260 being positioned thereover, the lacerated tendon 5 may then be ready to receive a flat member 270 (depicted with dashed line). Such may be employed with an insert guide 272. The insert guide 272 may be a flat tubular member sized and configured to receive the flat member 270 (such as any one of the flat members discussed in the previous embodiments) within a lumen defined longitudinally through the insert guide 272. The insert guide 272 may also act in cooperation with a pusher member (not shown) disposed within the lumen of the insert guide 272 and that may be sized and configured to effectively push the flat member 270 from the insert guide 272. The insert guide 272 may include a leading end 274 or distal end that may be sharp to initiate an incision in the tendon 5 so that the tendon may receive the insert guide 272 and/or the flat member 270 between the cradle 242 and the staple guide 260. As depicted, the insert guide 272 may be inserted into the tendon 5 between the cradle and the staple guide.

In one embodiment, the insert guide 272 may be inserted into the tendon 5 just slightly between the cradle 242 and the staple guide 260 and adjacent a first end 276 of the tool 240. At this position, the pusher member (not shown), disposed within the insert guide 272 and behind (proximal) the flat member 270, may push the flat member 270 forward or distally from the insert guide 272 and within the tendon 5 and tool 240. The tines 250, 264 extending from the staple guide 260 and the cradle 242 may act as a guide in funneling or assisting the flat member 270 to be properly positioned and aligned within the tendon 5. Upon the flat member 270 being positioned within the tendon 5, the insert guide 272 may be removed from adjacent the first end 276 of the tool 240.

In another embodiment, the insert guide 272 may be inserted into the tendon 5 and funneled through the tendon 5 and tool 240 between the tines 250, 264 so that the sharp leading end 274 may be positioned adjacent a second end 278 of the tool 240. The flat member 270 may also be positioned within the insert guide 272 and adjacent the leading end 274 with the pusher member (not shown) positioned proximal the flat member 270. The insert guide 272 may then be moved proximally or withdrawn with the pusher member holding the position of the flat member 270 within the tendon 5. In this manner, the flat member 270 may be deployed from the insert guide 272 and positioned within the tendon 5 and the tool 240.

Figure 20:
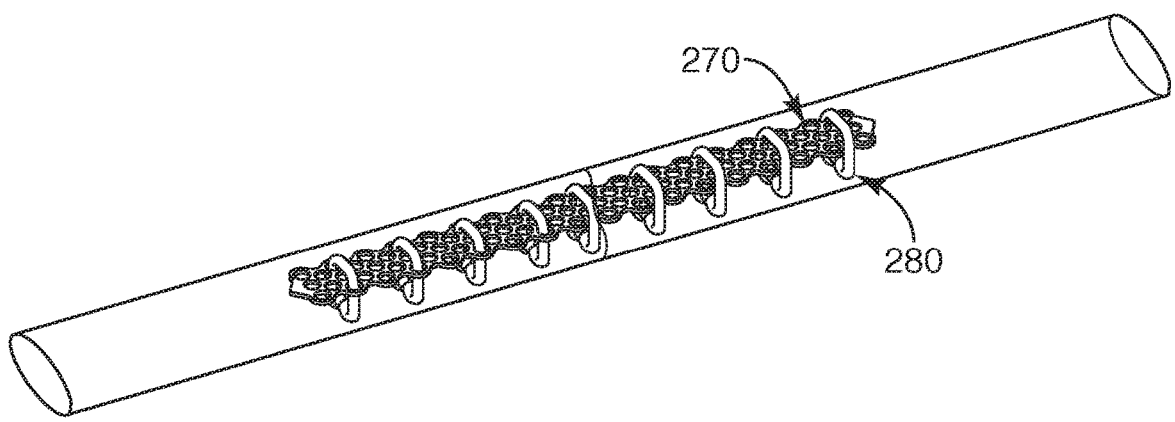
FIG. 20 is a perspective view of a repair device, depicting the flat member within the tendon and secured to the tendon and flat member, according to another embodiment of the present invention.

With reference to FIGS. 19 and 20, once the flat member 270 is positioned within the tendon 5 and within the tool 240 with the insert guide 272 removed, staples 280 may then be pushed through the slots 262 defined in the staple guide 260 via a staple tool (not shown), similar to the staple tool described relative to FIGS. 38-42 (not shown). Such staples 280 may be configured to extend through the tendon 5 and the flat member 270, similar to that described in previous embodiments. Once the staples 280 are positioned, the staple guide 260 and the cradle 242 may be removed from the tendon 5, leaving the lacerated tendon 5 with the flat member 270 within the tendon 5 and secured with the staples 280. As depicted, the flat member 270 may be similar to the flat member 22 described relative to FIG. 1. However, as set forth, the flat member 270 employed with the tool 240 may be any one of the flat members discussed herein.

In another embodiment, the tool 240 discussed above may be employed with the tubular member 202, as depicted in FIG. 10. As can be appreciated, such tubular member 202 may be positioned over a lacerated tendon 5 and then placed in the cradle 242 with the staple guide 260 positioned thereover, similar to that depicted in FIG. 17. Staples may then be inserted through the staple guide 260 and through the tubular member 202 and tendon 5.

The various components of the tool 240 may be formed from metallic materials or polymeric materials, or combinations thereof, and may be made using typical machining, laser cutting, or various molding techniques, or any other known manufacturing techniques as known to one of ordinary skill in the art.

Figure 21:
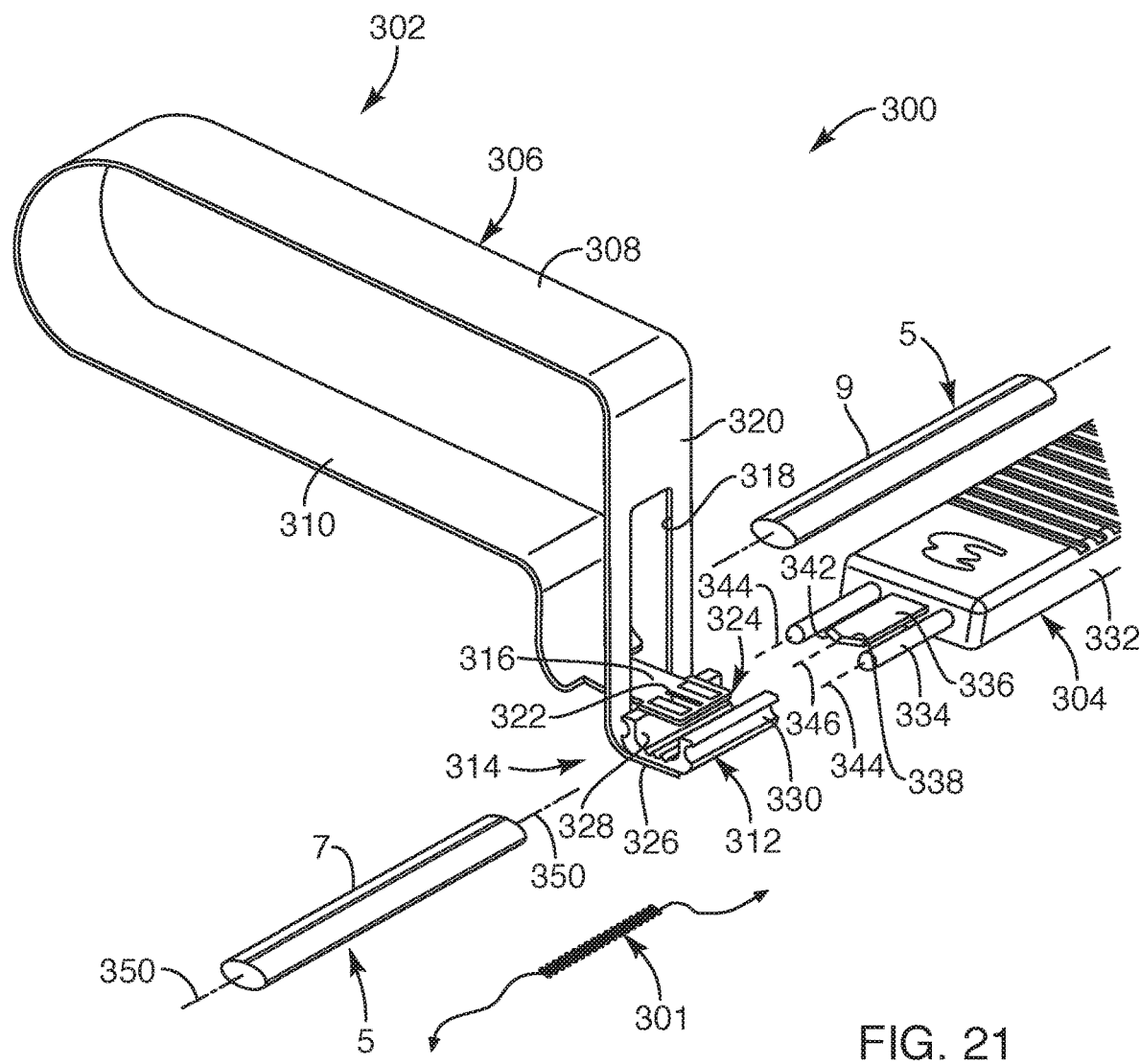
FIG. 21 is a perspective view of a tool system for accurate positioning of a repair device within a lacerated tendon, according to another embodiment of the present invention.

Referring to FIG. 21, another embodiment of a tool system 300 for inserting and securing a flat member 301 (which may be any one of the flat members set forth in the embodiments herein) to a lacerated tendon 5 is provided. The tool system 300 may include a spring clamp 302 and a guided scalpel 304. Such spring clamp 302 and guided scalpel 304 may be employed as tools for accurately affixing the lacerated tendon 5 together.

The spring clamp 302 may include a clamp handle 306 with an upper handle portion 308 and a lower handle portion 310. The spring clamp 302 may also include a cradle portion 312 and a clamp portion 314 each of which may be in the form of extensions of the upper and lower handle portions 308, 310, respectively. For example, the clamp portion 314 may include a tongue 316 extending from the lower handle portion 310 such that the tongue 316 extends through an opening 318 defined in a downward extension 320 extending from the upper handle portion 308 and over the cradle portion 312. The tongue 316 may include multiple windows 322 or slits defined in an end portion 324 of the tongue 316, the windows 322 positioned over the cradle portion 312 and sized and configured to receive anchors or staples (not shown) therethrough.

Figure 22:
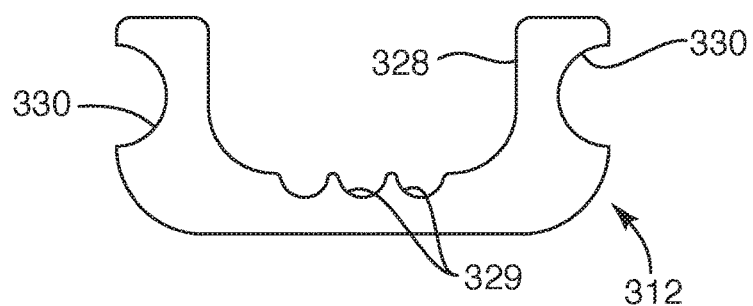
FIG. 22 is an end view of a cradle portion of the tool system, according to another embodiment of the present invention.

With respect to FIGS. 21 and 22, the cradle portion 312 may be positioned to define a portion of the opening 318 defined in the downward extension 320. The cradle portion 312 may be positioned and secured to a platform portion 326 extending horizontally from the downward extension 320. The cradle portion 312 may include a tendon channel 328 defined therein sized and configured to receive and position the severed tendons 5 there along. The cradle portion 312 may also include guide channels 330 defined in or along opposite outer sides of the cradle portion 312, the guide channels 330 extending parallel with the tendon channel 328. The tendon channel 328 may include a surface along its bottom surface that may include two or three secondary grooves 329 defined in the bottom surface. The secondary grooves 329 extending co-axial and along at least a portion of a length of the tendon channel 328 and sized and configured to act as an anvil to engage the anchors or staples (not shown).

The spring clamp 302 includes a spring element such that the upper and lower handle portions 308, 310 may be biased outward to facilitate the tongue 316 to be biased against an upper side of the cradle portion 312. In other words, the tongue 316 and cradle portion 312 are biased together such that an underside surface of the tongue 316 may be biased against and may be in direct contact with an upper side of the cradle portion 312. With this arrangement, a physician may grasp the spring clamp 302 at the clamp handle 306 and squeeze the upper and lower handle portions 308, 310 toward each other to separate the tongue 316 from the cradle portion 312. Likewise, the physician may loosen the grip of the spring clamp 302, which in turn automatically moves the tongue 316 against the cradle portion 316 via the spring element.

Figure 23:
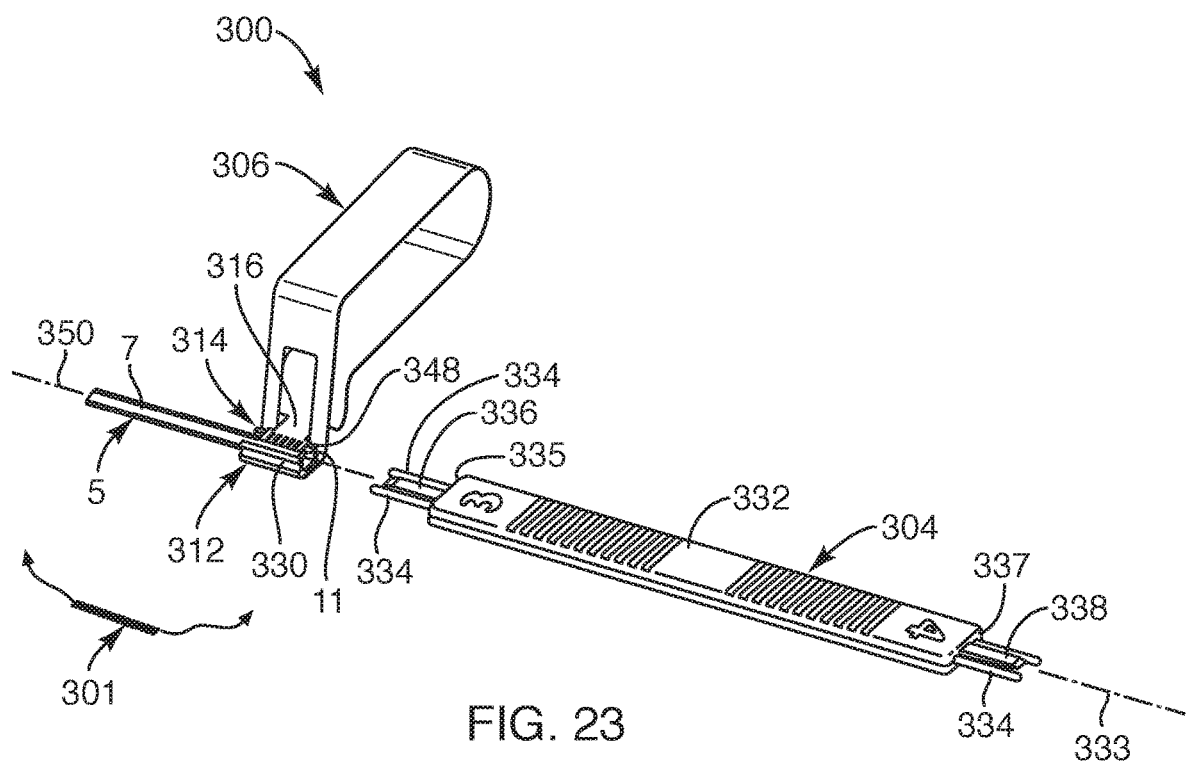
FIGS. 23-28 are perspective views of the tool system of FIG. 21, depicting method steps for employing the tool system, according to another embodiment of the present invention.

With respect to FIGS. 21 and 23, as set forth, the tool system 300 may include the guided scalpel 304. The guided scalpel 304 may include an elongated handle 332, one or more blades, and guide rods 334. The elongated handle 332 may define a handle axis 333 along its longitudinal length extending between opposite first and second ends 335, 337. In one embodiment, the handle 332 may include a first blade 336 and a second blade 338 fixedly extending from opposite ends of the elongated handle 332. The first and second blades 336, 338 may include a generally flat structure and elongated with an end portion having a beveled edge 340 extending to a cutting edge 342. The guide rods 334 may extend along each side of the first and second blades 336, 338, extending in a parallel arrangement such that each of the first and second blades 336, 338 extends between a pair of guide rods 334. The guide rods 334 may be cylindrically shaped and sized and configured to correspond with the guide channels 330 defined in the cradle portion 312. Also, the guide rods 334 may extend from the handle 332 relative to the first and second blades 336, 338 along the same plane or extend in generally parallel planes. For example, the plane of a given pair of guide rods 334 may be defined between and by longitudinal axes 344 of the given pair of guide rods 334. The plane of the first or second blades 336, 338 may be defined along a central blade axis 346 such that the plane extends generally centrally and symmetrically relative its elongated flat structure and extend parallel or co-planar with the plane defined by the corresponding guide rods 334. In one embodiment, the blade axis 346 may be substantially co-axial with the handle axis 333. In another embodiment, the blade axis 346 may be parallel with the handle axis 333. The purpose and function of the first and second blades 336, 338 extending in separate or parallel planes relative to the plane of their associated guide rods 334 will be described in detail hereafter.

Referring now to FIGS. 21, and 23 through 29, a method for employing the tool system 300 with a flat member 301 upon a severed tendon 5 will now be described. With respect to FIGS. 21 and 23, a first tendon portion 7 may be placed within the tendon channel 328 of the cradle portion 312 by squeezing the clamp handle 306 to open the clamp portion 314. The first tendon portion 7 may be positioned within the cradle portion 312 so that a first tendon end 11 aligns with a first edge 348 of the tongue 316 and, once positioned, the clamp portion 314 may be released so that the tongue 316 biases tight against the first tendon portion 7 within the cradle portion 312.

At this juncture, a thickness or diameter of the first tendon portion 7 may be determined. Once the thickness is determined, the guided scalpel 304 may be employed at one of four orientations. For example, if the first tendon portion is approximately three millimeters thick from bottom to top as it sits in the cradle portion 312, then the physician may orient the guided scalpel 304 with, for example, the numeral three indicia on the handle 332 to be positioned and aligned adjacent the first tendon portion 7, as depicted in FIG. 23. With this particular orientation, a distance between the plane of the first blade 336 and the plane of the associated guide rods 334 may be separated by, for example, 1.5 mm so that the first blade 336 will correspond with a center axis 350 of the first tendon portion 7. Similarly, if the first tendon portion 7 is, for example, 4 mm thick, than a physician may orient the guided scalpel 304 with the numeral four indicia on the handle 332 to be positioned and aligned adjacent the first tendon portion 7. This particular orientation may provide a distance between the plane of the second blade 338 and the plane of its associated guide rods 334 of 2 mm so that the blade may accurately correspond with the center axis 350 of the first tendon portion 7. Likewise, turning the handle 332 over may display the numeral one and two indicia on the handle to provide other predetermined distances between the plane of the first and second blades 336, 338 and the plane of their associated guide rods 334.

Once the guided scalpel 304 is properly oriented to correspond with a given thickness of the first tendon portion 7, the guide rods 334 may be inserted within the guide channels 330 of the cradle portion 312. For example, with respect to FIG. 24, the guided scalpel 304 may be moved with the guide rods 334 inserted through and into the guide channels 330 to a hard stop, which may be defined by the first end 335 of the handle 332. In this manner, the first blade 336 may provide an accurate incision through the center axis 350 of the first tendon portion 7. The guided scalpel 304 may then be withdrawn from the first tendon portion 7.

Figure 24:
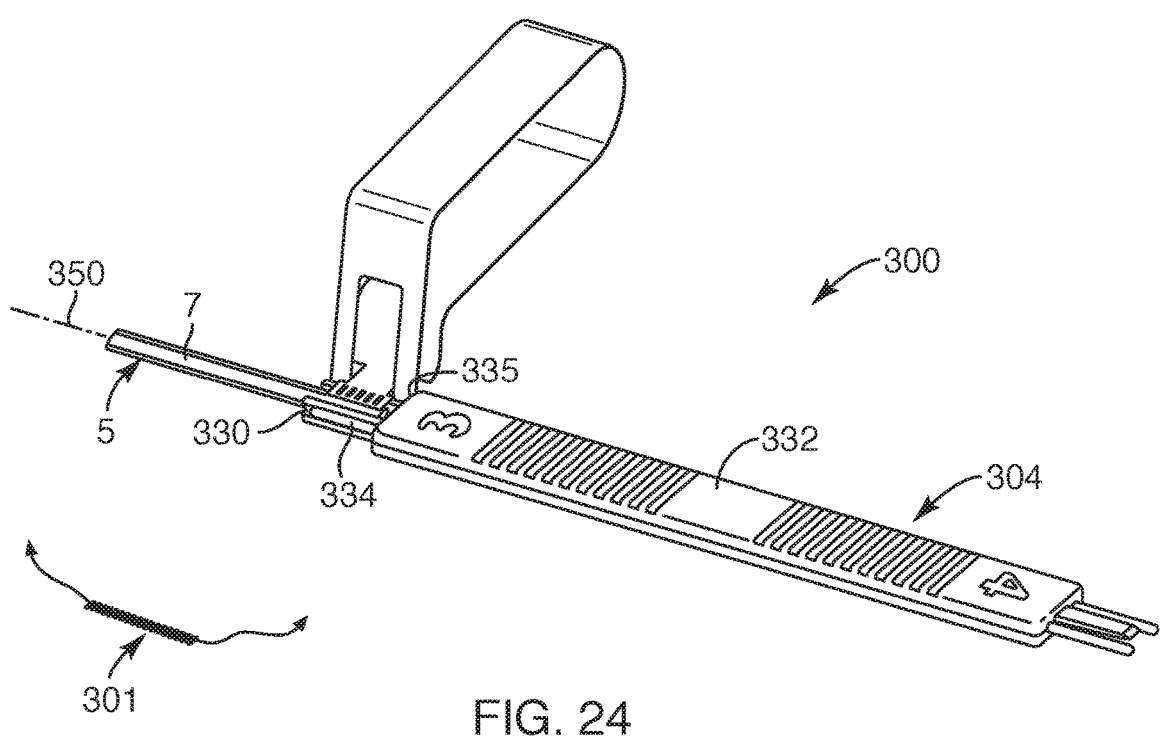
Figure 25:
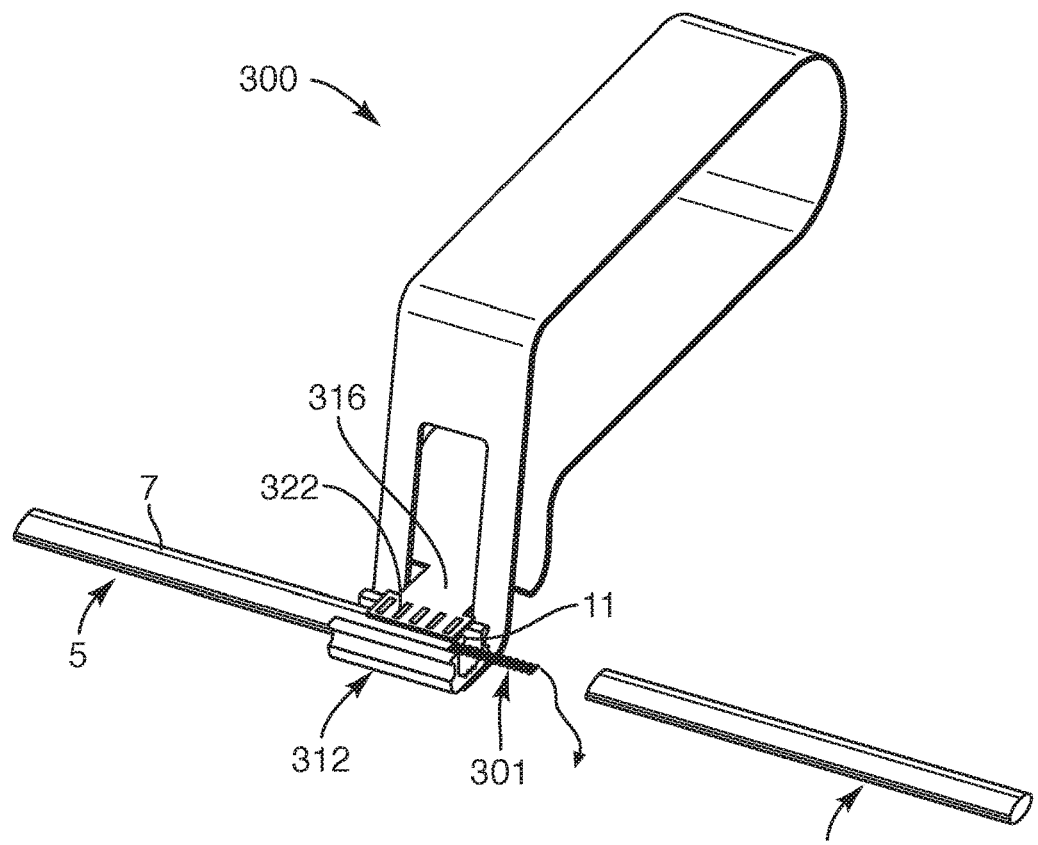

With respect to FIGS. 24 and 25, the flat member 301 may be inserted into the incision made by the first blade 336 in the first tendon portion 7. In one embodiment, the flat member 301 may include a suture and needle arrangement at each end of the flat member 301. The needle may be threaded through the incision of the first tendon portion 7 and then laterally through a side of the first tendon portion 7 to then pull the flat member 301 into the incision so that about half of the flat member 301 is positioned in the first tendon portion 7 and about half of the flat member 301 is exposed at the first tendon end 11, as depicted in FIG. 25. Once the flat member 301 is appropriately positioned within the first tendon portion 7, the portion of the flat member 301 within the tendon may be anchored to the tendon. Such anchoring may be employed with an anchor instrument (not shown) such that anchors may be inserted through the windows 322 defined in the tongue 316 to pass through the flat member 301 and the first tendon portion 7. As in previous embodiments, the anchors may pass through bottom and top sides of the first tendon portion 7 as well as through cells or openings defined in the flat member 301, similar to that depicted with internally positioned flat members and anchors in previous embodiments to thereby anchor the flat member 301 to the first tendon portion 7.

In another embodiment, prior to inserting and anchoring the flat member 301, the first tendon portion 7 may be removed from the cradle portion 312 so that the physician may thread the flat member 301 via the suture and needle within the incision in the first tendon portion 7 without the aid of the tendon being clamped in the cradle portion 312. Once the flat member 301 is properly positioned in the first tendon portion 7, the first tendon portion 7 may be repositioned and aligned in the cradle portion 312 so that the flat member 301 may be anchored to the tendon with, for example, anchors or staples.

Figure 26:
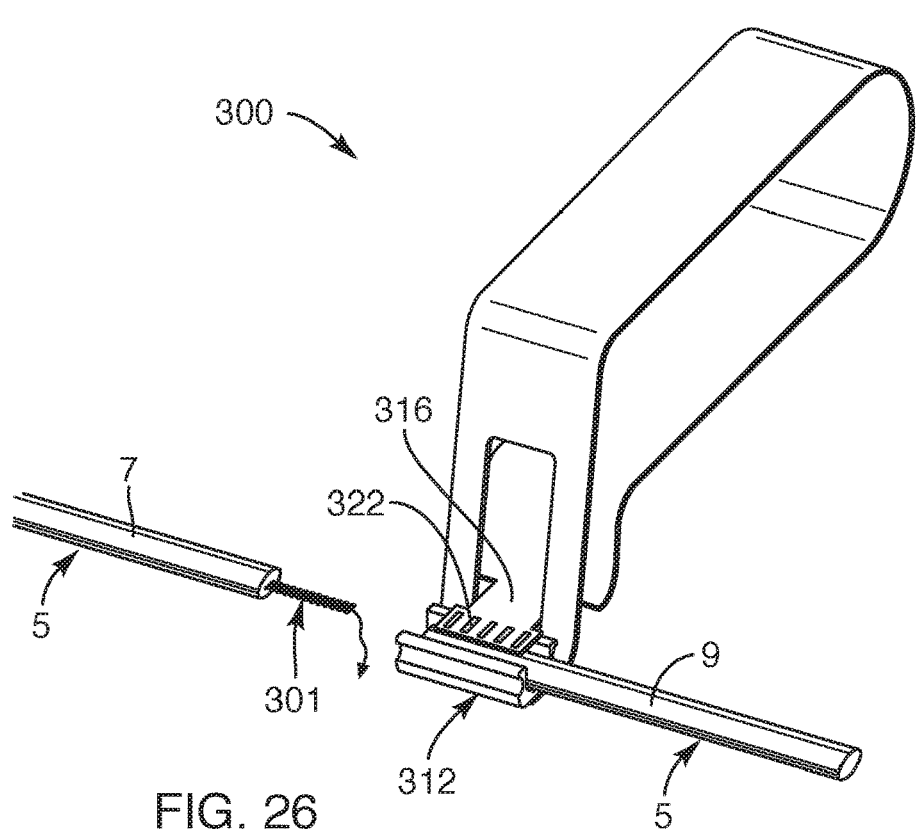
Figure 27:
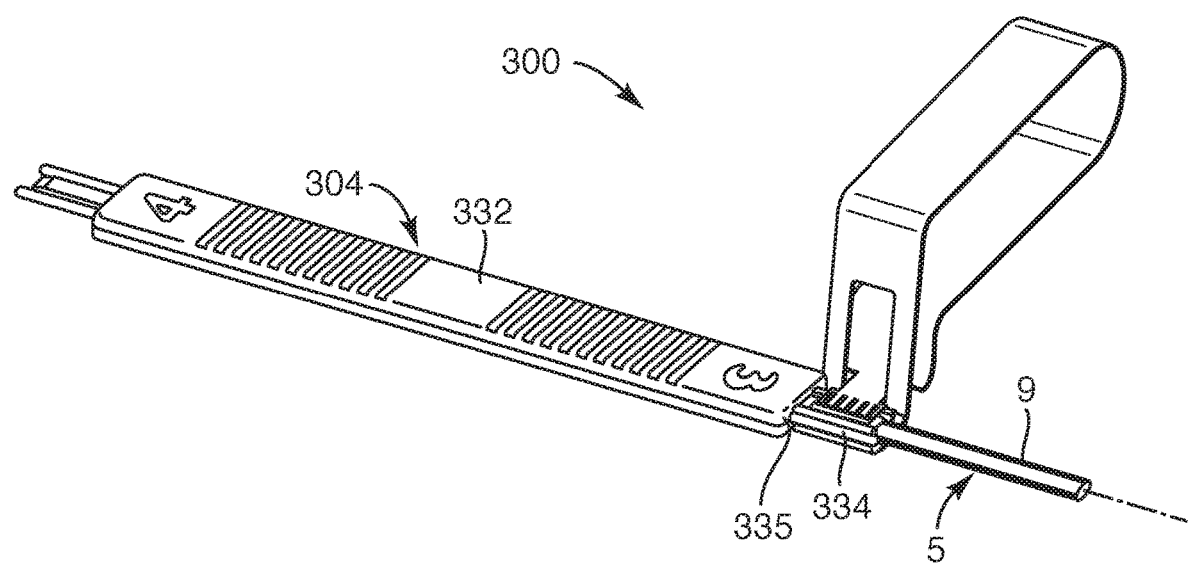
Figure 28:
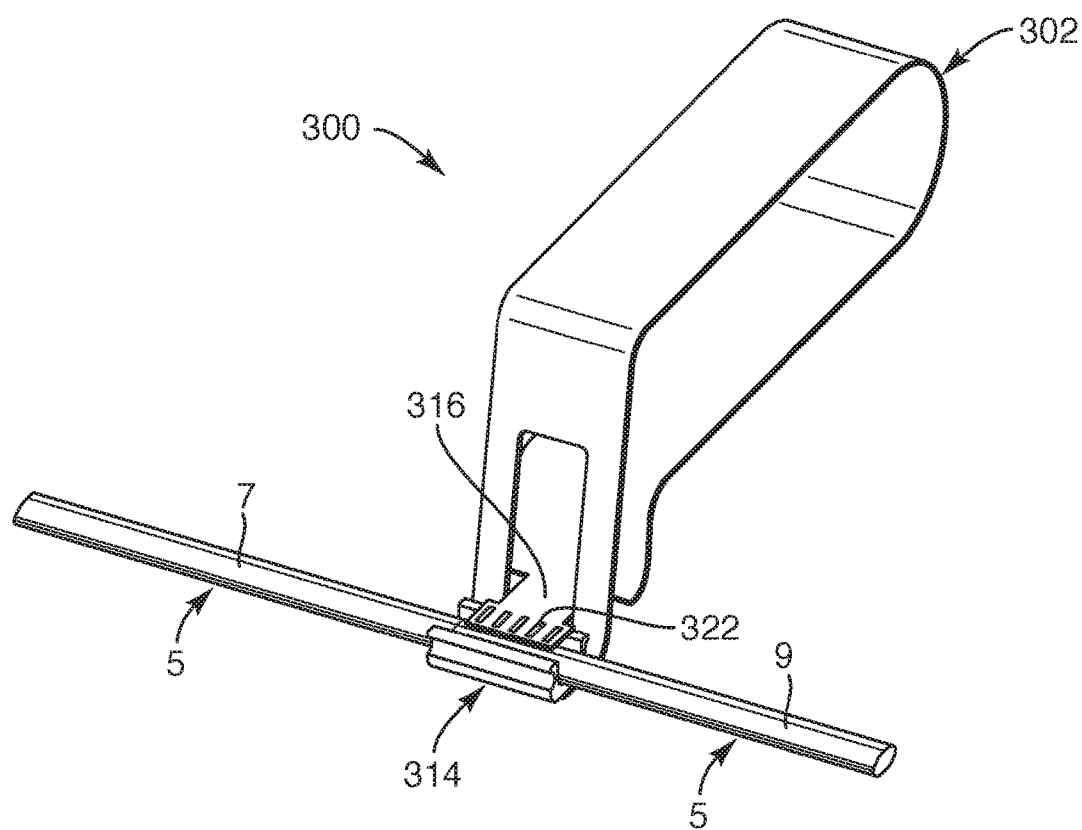
Figure 29:
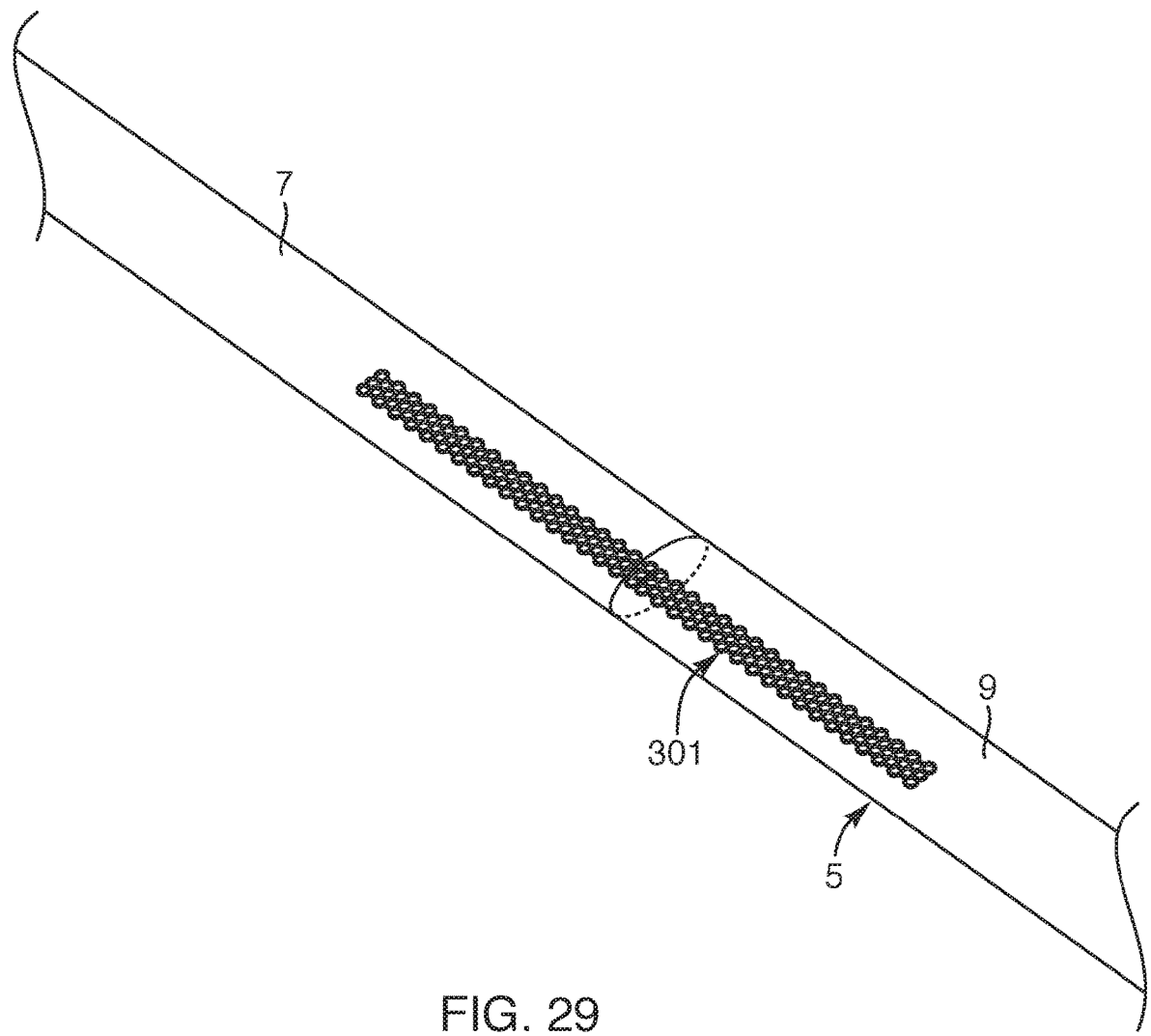
FIG. 29 is a perspective view of a repaired lacerated tendon with a repair device positioned within the tendon, according to another embodiment of the present invention.

As depicted in FIG. 26, once the first tendon portion 7 has been anchored to the flat member 301, the first tendon portion 7 may be removed from the cradle portion 312. The second tendon portion 9 may then be positioned in the cradle portion 312 so that a second tendon end 13 is aligned with a second edge 352 of the tongue 316 and then clamped therein with the tongue 316 biased over the second tendon portion 9. Similar to that set forth previously, the guided scalpel 304 may then be positioned to provide an incision along the center axis 350 of the second tendon portion 9 by sliding the guide rods 334 through the guide channels 330 until reaching the hard stop at the first end 335 of the handle 332, as depicted in FIG. 27. Once the incision is made within the second tendon portion 9, the guided scalpel 304 may be removed. The second tendon portion 9 may then be threaded with the suture and needle at the end of the exposed portion of the flat member 301 at the first tendon portion 7 into the incision to pull the exposed portion of the flat member 301 into the incision and into the second tendon portion 9, thereby, abutting the first tendon end 11 against the second tendon end 13, as depicted in FIG. 28. At this juncture, the second tendon portion 9 may be anchored to the flat member 301 positioned within the second tendon portion 9 by inserting anchors (not shown) through the windows 322 of the tongue 316, similar to that previously set forth. Once the flat member 301 is anchored to the first and second tendon portions 7, 9, the lacerated tendon 5 may be removed from the cradle portion 314 of the spring clamp 302, as depicted in FIG. 29. The suture and needles may then be snipped and removed from the repaired tendon 5 with the flat member 301 positioned therein.

Figure 30:
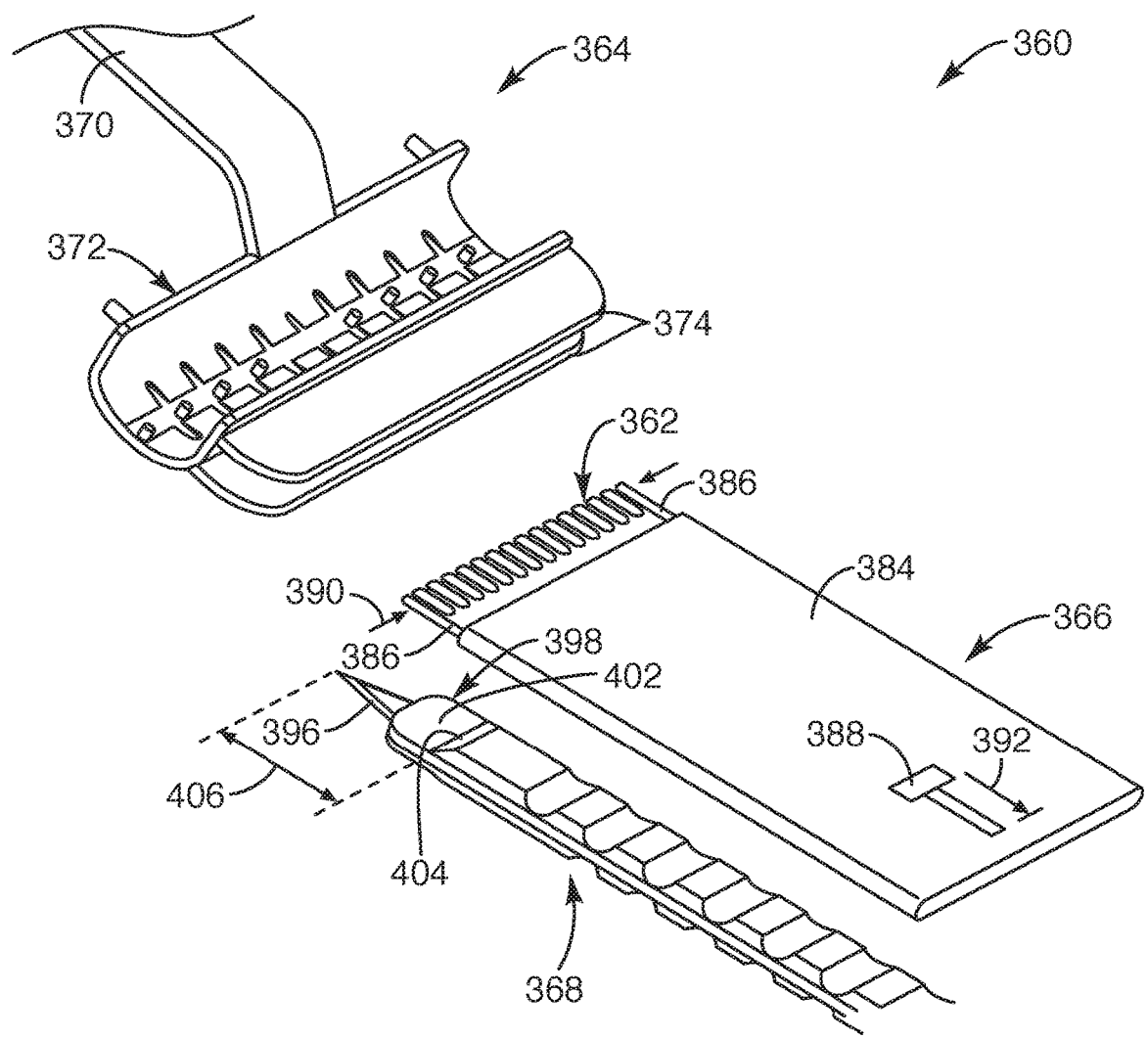
FIG. 30 is a perspective view of another embodiment of a tool system for accurate positioning of a repair device within a lacerated tendon, according to the present invention.

With respect to FIG. 30, another embodiment of a tool system 360 with similar features of the tool system 300 previously described relative to FIGS. 21-29, except this tool system 360 may be employed by slicing horizontally through first and second portions 7, 9 of a severed tendon 5 for accurately positioning a flat member 362 within the severed tendon 5. It should be noted that the flat member 362 employed with the tool system 360 may be any one of the flat member embodiments or the like set forth herein. In one embodiment, the tool system 360 may include a tendon holder 364, an inserter member 366, and a scalpel 368.

Figure 31:
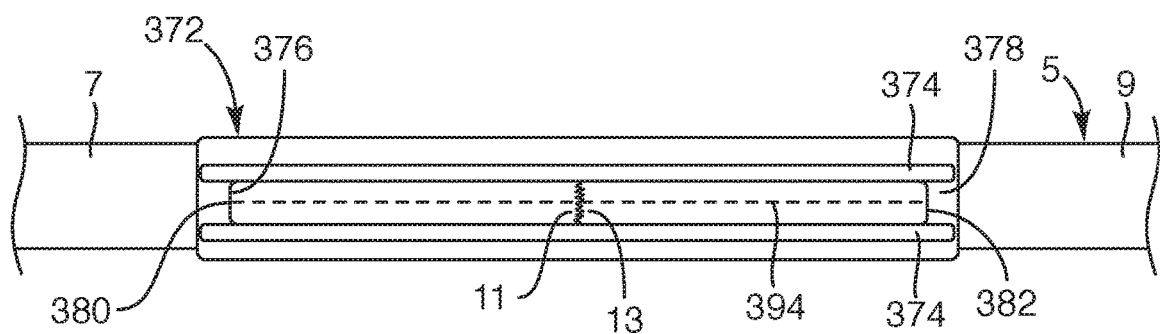
FIG. 31 is a front view of a cradle portion, depicting a window defined in the cradle portion through which the tendon is exposed for horizontal incision of the tendon, according to another embodiment of the present invention.

For example, with respect to FIGS. 30 and 31, the tendon holder 364 may include a handle 370 coupled to a cradle portion 372. The cradle portion 372 may be sized and configured to receive end portions of a severed tendon 5 therein with a anchor guide (not shown) positioned over the severed tendon 5 with a sandwiching arrangement. The cradle portion 372 and anchor guide of this embodiment may include similar structural features for receiving and containing the severed tendon and then receiving anchors or staples, similar to that described relative to the cradle 242 and staple guide 260 in FIGS. 15-17.

The cradle portion 372 of the embodiment depicted in FIGS. 30 and 31 may also include guide rails 374 with a window 376 defined in a side wall 378 of the cradle portion. Such window 376 may be elongated, extending between a first end 380 and a second end 382, and defined between the guide rails 374, the guide rails 374 extending laterally from the side wall 378 of the cradle portion 372 and extending longitudinally along the side wall 378 of the cradle portion 372.

The inserter member 366 may include an elongated handle portion 384 with a pair of arms 386 extending from one end of the elongated handle portion 384. The arms 386 may be sized and configured to grasp a repair device, such as the flat member 362. In one embodiment, the arms 386 may include an actuating element 388 that may move the arms 386 between an outward open position and an inward closed position. In the inward closed position, the arms 386 may be biased toward an inward position, as shown by arrows 390, to be biased toward each other such that each arm 386 may hold the flat member 362 at opposite ends thereof. In the outward open position, the arms 386 may be moved outwardly by the actuating element 388 being moved, as shown by arrow 392, to release the flat member 362 from the arms 386.

The tool system 360 of this embodiment may be employed with a severed tendon 5 by first positioning first and second tendon portions 7, 9 of the severed tendon 5 in the cradle portion 372. With the severed tendon 5 positioned within the cradle portion 372, the anchor guide may then be positioned over the cradle portion 372, similar to that depicted in FIG. 17, as previously set forth. The tendon 5 may then receive a horizontal slice 394 extending through both the first and second tendon portions with the scalpel.

The scalpel 368 may include a blade 396 extending from a scalpel handle 397. The scalpel handle 397 may include an end portion 398 with opposing sides sized and configured to fit between the guide rails 374. The opposing sides may each include a surface 402 that extends to an abutting edge 404, the surface 402 and blade 396 defining a length 406 that corresponds to a predetermined depth through the window 376 defined in the cradle portion 372 for making an incision within the tendon 5. As such, the scalpel 368 may be inserted through the window 376 adjacent the first end 380 of the window 376 until each abutting edge 404 abuts the guide rail 374 with the opposing sides positioned between the guide rails 374. In this manner, the scalpel 368 may be inserted into a side of the tendon 5 at an accurate predetermined distance. The scalpel 368 may then be moved from the first end 380 of the window 376 to the second end 382 of the window 376 defined in the cradle portion 372, thereby, providing a slice 394 extending horizontally along a length of the first and second portions 7, 9 of the severed tendon 5. The scalpel 368 may then be removed.

At this stage, the inserter member 366, holding the flat member 362 therewith, may then be oriented and aligned with the previously made slice 394 through the window 376. The inserter member 366 may then be moved forward so that the flat member 362 is inserted through the window 376 and into the sliced incision in the tendon 5. The inserter member 366 may then be moved to the outward open position via the actuating element 388 to release the flat member 362 within the incision in the tendon 5, after which, the inserter member 366 may be withdrawn. With the flat member 362 positioned within the tendon 5, anchors may then be inserted through the slots defined in the anchor or staple guide (see FIG. 17), to thereby fix the flat member 362 to the tendon 5 and thus, affix the first and second tendon ends 11, 13 together.

As set forth, although the flat members 301, 362 depicted with the tool systems 300, 360 herein are similar to the flat member embodiment described in FIG. 1, such flat members 301, 362 may be similar to the embodiments described in FIGS. 4, 6, 7, and 9, or variations thereof. Such variations of a flat member may include a weaved, knitted, or braided polymer fiber or wire, similar to that shown in FIGS. 4 and 6, but without being disposed with the covering 88 between thin polymer sheets or embedded within a thin polymer material. In this manner, other embodiments of a flat member may include all the structural characteristics of the weaved, knitted, and/or braided polymer fiber or wire described relative to the lattice structures of FIGS. 4 and 6, but for the polymeric encasing.

In addition, relative to FIGS. 32 and 33, an embodiment of a flat member 410, without the polymeric encasing, may include a lattice or mesh structure having flexible structural characteristics. In one embodiment, the lattice or mesh structure may include a weaved, knitted, and/or braided configuration. Further, in one embodiment, the lattice may be made from polymeric filaments 411 or fibers that are weaved, knitted, and/or braided to form a ribbon or the flat member 410. The flat member 410 may include a length 412 extending between first and second ends 414, 416 and define an axis 418 extending longitudinally and centrally through the flat member 410. The flat member 410 may also include a width 420 and a depth 422.

The flat member 410 of this embodiment may include first and second portions 424, 426 with an intermediate portion 428 therebetween, similar to previous embodiments. The first and second portions 424, 426 of the flat member 410 may provide structural characteristics that elongate or facilitate strain elongation along the length 412 or axis 418 of the flat member 410 and, specifically, along the first and second portions 424. As in previous embodiments, the intermediate portion 428 may provide structural characteristics that substantially prevent or resist elongation along the length 412 of the intermediate portion 428. In one embodiment, the term substantially prevents or resists elongation may mean minimal elongation (between, for example, adjacent anchors 430 closest to the ends of the tendon 5 at the laceration or at the intermediate portion) in the order of up to about 0.2 mm, including zero or no elongation. In another embodiment, minimal elongation may mean up to about 0.5 mm along the intermediate portion. In this manner, minimal elongation may occur as a load is placed upon the tendon and may come back or un-elongate back to zero or no elongation or remain up to about 0.2 mm. Such definition of minimal elongation for an intermediate portion of an elongated flat flexible member may be consistent with any one of the embodiments described herein setting forth an intermediate portion that substantially resists elongation along a length of the intermediate portion.

At the intermediate portion 428, the angle of the filaments 411 may extend with a smaller pitch or smaller angle relative to the axis 418 than the filaments 411 along the first and second portions 424, 426 of the flat member 410. Otherwise said, the pitch or angle of the filaments 411 along the first and second portions 424, 426 may be larger than the pitch or angle of the filaments 411 along the intermediate portion 428. Such angle or pitch may facilitate the structural characteristics of elongation of the first and second portions 424, 426 and substantially prevent elongation along the intermediate portion 428. With this arrangement, the flat member 410 may be inserted internally within a severed tendon 5 and anchored to the tendon 5, utilizing anchors 430 or the like or any other anchors for fixing the flat member 410 to the tendon 5. In one embodiment, such anchors 430 may be discrete and separate relative to the frame member. Further, the flat member 410 of this embodiment may be inserted into the tendon 5 employing any one of the tool systems described herein.

Upon affixing the flat member 410 within the tendon 5, as the tendon 5 elongates with a load, the first and second portions 424, 426 may also elongate with the tendon 5. Further, as the tendon elongates, the intermediate portion 428 being positioned adjacent the severed ends of the tendon may also substantially prevent elongation to, thereby, facilitate the severed ends to properly heal and allow the other portions of the tendon adjacent or over the first and second portions 424, 426 to be stressed or exercised and become stronger.

In another embodiment, depicted in FIG. 34, a side view along a portion of the length of the flat member 410 of FIG. 32 is shown. With respect to FIGS. 32 and 34, in one embodiment, the flat member 410 may include crimps 432 or folds that extend laterally along the width 420 or across the length 412 of the flat member 410. Such folds or crimps 432 may be placed along the length 412 at predetermined positions at, for example, positions along the first and second portions 421, 426 of the flat member 410. The crimps 432 may be made by heating the polymeric filaments 411 to the crimped or folded position or any other technique known in the art. In another embodiment, the filaments 411 may include one or more loops along their length so that upon a force being placed along the length of the flat member, the length may elongate at least along the first and second portions 424, 426. In another embodiment, the filaments 411 may extend with a zig-zag along the length of the filaments. In this manner, upon the flat member 410 being secured to a severed tendon 5, the first and second portions 424, 426 may further elongate along their respective lengths as the tendon 5 is tensioned and elongates while maintaining the severed portions substantially affixed adjacent each other along the intermediate portion 428 of the flat member 410.

With respect to FIG. 35, another embodiment of a repair device 440 for repairing a severed tendon is provided. In this embodiment, the repair device 440 may include one or more lines 442 and multiple anchors 444 or staples. The one or more lines 442 may be formed of multiple filaments and/or fibers that may be braided, weaved, and/or knitted, or the like. The one or more lines 442 may be coupled to the anchors 444. Such coupling may be employed with posts and/or eyelets (not shown) via wrapping the line 442 around or through the respective posts and/or eyelets. In another embodiment, the anchors 444 may include bends or recesses (not shown) that may receive the lines 442 for wrapping and coupling to the anchors 444. The one or more lines 442 may be coupled to opposite ends 445 of a top end 446 of each of the anchors 444. In another embodiment, the one or more lines 442 may be coupled to a mid-portion 448 or base at, or adjacent to, the top end 46 of each of the anchors 444. Further, in another embodiment, the one or more lines 442 may be coupled to the opposite ends 445 and the mid-portion 448 of the top end 446 of the anchors 444. Such one or more lines 442 may include multiple folds, crimps, loops, and/or zig-zags along first and second portions 450, 452 of the repair device 440 without such folds, crimps, loops, and/or zig-zags along an intermediate portion 454 of the repair device 440. The repair device 440 may be secured to a severed tendon 5 such that the anchors 444 may extend through first and second end portions 7, 9 of the severed tendon 5 and the one or more lines 442 remain on the outer surface of the severed tendon 5. In another embodiment, another repair device, substantially identical to the repair device, may be positioned and secured to an opposite side of the severed tendon. In this manner, the two repair devices 440 may be secured to a severed tendon, each repair device 440 on opposite sides of the tendon 5.

In another embodiment, the one or more lines may extend between adjacent staples at an angle, extending with a braided, weaved, and/or knitted configuration. In another embodiment, the one or more lines may be in the form of a ribbon or flat member, similar to that shown in FIG. 32, that may or may not include pre-attached anchors.

The anchors or staples, as set forth herein, may be a metallic material or a polymeric material. Such metallic materials may be stainless steel, Nitinol, titanium, or magnesium, or combinations thereof or any other suitable biocompatible metallic material or bioresorbable materials, or the like. The polymeric materials may be any suitable polymeric material, such as a bioresorbable or bioabsorbable polymeric materials or any other suitable biocompatible polymeric material. The repair device, as set forth herein, may be any suitable biocompatible material, such as a metallic or polymeric material. The repair device may also include a bioresorbable material or components of the repair device that are bioresorbable.

In one embodiment, the repair device may include collagen attached thereto. The collagen may be coated, layered, inserted, and/or impregnated into the repair device. In one embodiment, the collagen may be formed on the filaments or fibers of the repair device in a manner to enhance and accelerate the healing of the tendon at the repair site. Such collagen may be added to any one of the repair devices disclosed herein.

The components of the tool systems 300, 360 may be made of metallic and/or polymeric materials and manufactured using machining, laser cutting, crimping, and/or various molding techniques, as known to one of ordinary skill in the art. For example, the spring clamp may be a metallic material with portions of the handle made of a polymeric material. The cradle portion may also be made of a polymeric material by molding or machining the cradle portion and then fixing the cradle portion to the downward extension using typical fastening techniques. The handle portion of the guided scalpel may be formed of a suitable polymeric material with the blades made of a metallic material. The guide rods may be a metallic or a polymeric material.

Figure 36:
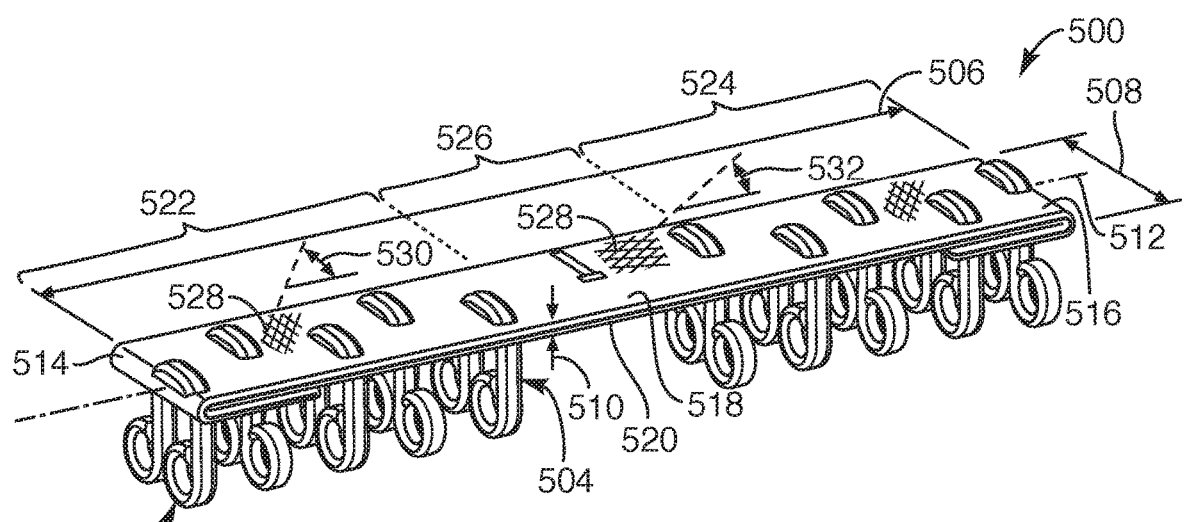
FIG. 36 is a perspective view of another embodiment of a repair device having an elongated flat member with multiple anchors, according to the present invention.

Now with reference to FIG. 36, another embodiment of a repair device 500 for repairing a lacerated tendon or the like is provided. This embodiment may include similar features to the embodiment depicted and described in FIG. 35. In this embodiment, the repair device may exhibit an elongated flexible member 502 with multiple anchors 504 extending through the elongated flexible member 502. The elongated flexible member 502 may include a length 506, a width 508 and a depth 510, the length 506 defining a longitudinal axis 512. The elongated flexible member 502 may include and extend between a first end 514 and a second end 516, the first end 514 being opposite the second end 516. Further, the flexible member 502 may include an upper surface 518 and an under-side surface 520 and define a rectangular shaped periphery. Further, the elongated flexible member 502 may include a first portion 522 and a second portion 524 with an intermediate portion 526 therebetween. The first portion 522 may include a first series of the multiple anchors 504 and the second portion 524 may include a second series of the multiple anchors 504.

The flexible member 502 may include a ribbon like structure. Such ribbon like structure may be flexible such that it may be readily foldable or bendable and may readily move over or around a small radius. In one embodiment, the flexible member 502 may be somewhat rigid when placed in tension. In another embodiment, the flexible member 502 may exhibit a flat structure. In still another embodiment, the flexible member 502 may be formed with multiple filaments 528. The multiple filaments 528 may be interconnected such that the filaments may be braided, knitted, and/or woven together to form a flat structure. In one embodiment, the multiple filaments 528 may be polymeric filaments that are biocompatible. In another embodiment, such polymeric filaments may be bioresorbable or bioabsorbable.

The first and second ends 514, 516 of the flexible member 502 may include folded portions such that ends of flexible member 502 may be folded over to the under-side surface 520 to define the first and second ends 514, 516. Such folded portions may reinforce the ends of the flexible member 502. In another embodiment, the ends may be reinforced with stitching or an adhesive or other polymeric layer or any other component to reinforce the first and second ends so that unraveling of the multiple filaments 528 is prevented.

As in previous embodiments, upon a load being placed along the axis 512 of the flexible member 502, the structural characteristics of the flexible member 502 may be such that the first portion 522 and the second portion 524 of the flexible member 502 may be configured to elongate while the intermediate portion 526 may be configured to limit or substantially resist elongation. In one embodiment, the multiple filaments 528 may be interconnected in a manner (i.e., weaved, braided, and/or knitted) so as to facilitate elongation and to limit elongation over predetermined portions of the length 506 of the flexible member 502. In one embodiment, the multiple filaments 528 along the first and second portions 522, 524 may extend with a first pitch 530 or angle relative to the axis 512 of the flexible member 502 and the multiple filaments 528 along the intermediate portion 526 may extend with a second pitch 532 or angle relative to the axis 512 of the flexible member 502 such that the first pitch 530 is greater than the second pitch 532. In another embodiment, the multiple filaments 528 may include a similar pitch along the length of the flexible member, but include different patterns of weaving, braiding, and/or knitting along the length 506 to facilitate elongation and minimize elongation of the flexible member 502. In still another embodiment, the multiple filaments 528 of the flexible member 502 may exhibit a substantially continuous or constant pitch and/or a continuous or constant weave, braided, or knitted pattern between the interconnected filaments 528 along the length 506 of the flexible member 502 such that elongation of the flexible member 502 is limited or such that the elongation of flexible member 502 may be substantially constant along the length 506 of the flexible member 502.

As set forth, the elongated flexible member 502 may include multiple anchors 504. Such multiple anchors 504 may be pre-attached or pre-inserted through the flexible member 502 prior to anchoring the repair device 500 to a lacerated tendon. In one embodiment, the multiple anchors 504 may be positioned and pre-inserted through the first and second portions 522, 524 of the flexible member 502 in a staggered arrangement, as depicted. In another embodiment, the multiple anchors 504 may be positioned and pre-inserted through the flexible member 502 such that the multiple anchors 504 are aligned along the length 506 of the first and second portions 522, 524 of the flexible member 502.

The multiple anchors 504 may be formed of a metallic or polymeric material or combinations thereof. Further, the multiple anchors 504 may be formed of a biocompatible material or a bioresorbable or bioabsorbable material. For example, the multiple anchors 504 may be formed of stainless steel, titanium, Nitinol, or magnesium, or combinations thereof, or any other suitable material, known in the art.

Figure 37A:
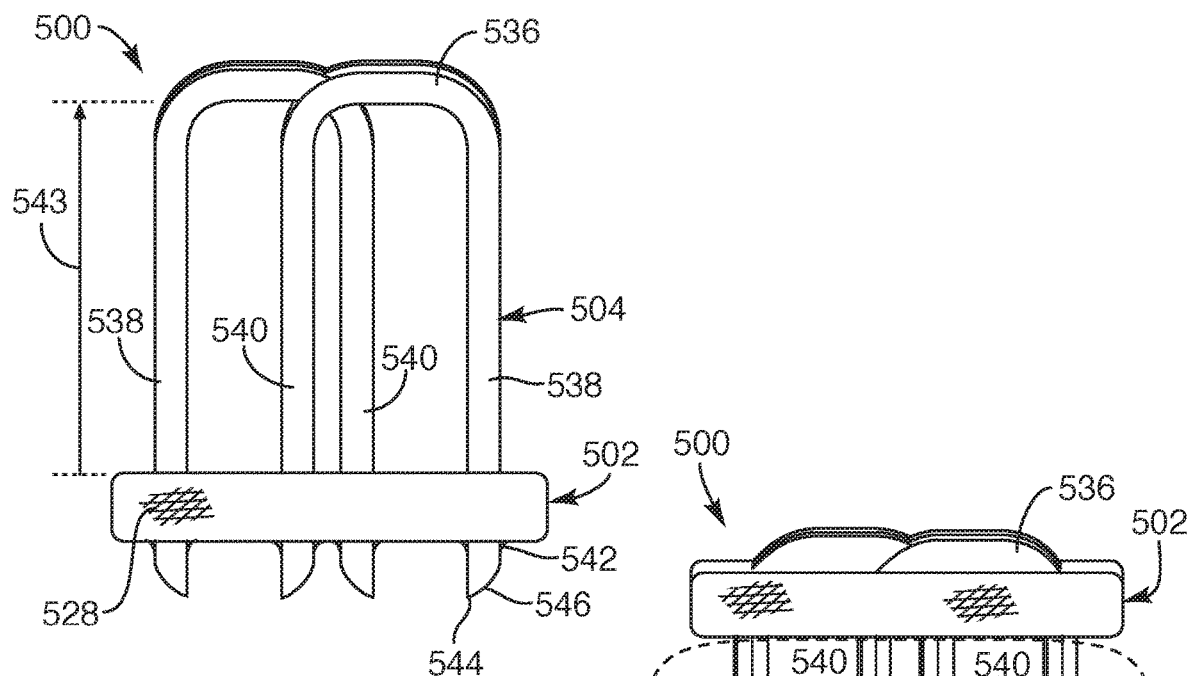
FIG. 37A is an end view of the repair device, depicting the multiple anchors in a first position, according to another embodiment of the present invention.
Figure 37B:
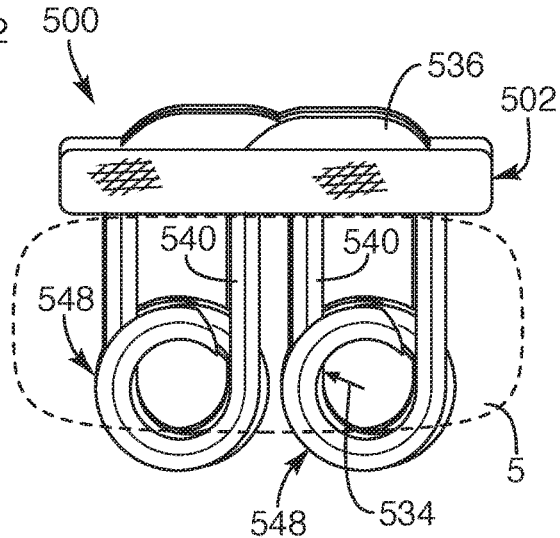
FIG. 37B is an end view of the repair device, depicting the multiple anchors in a second position, according to another embodiment of the present invention.

With respect to FIGS. 37A and 37B, end views of the multiple anchors 504 positioned in the flexible member 502 are provided. The multiple anchors 504 may be moved from a first anchor position or linear position (FIG. 37A) to a second anchor position or curved position (FIG. 37B). As depicted in FIG. 37A, in the first anchor position, each anchor 504 may include a u-shaped configuration. The first anchor position may be a pre-use position or the position prior to the anchors 504 being anchored to a tendon. Such u-shaped configuration may include an intermediate portion 536 or base and first and second legs 538, 540, the first and second legs extending substantially perpendicular from and relative to the intermediate portion 536. Each of the anchors 504 may be positioned and inserted through apertures defined by the multiple filaments 528 of the flexible member 502. Further, as set forth, such anchors 504 may be pre-inserted or pre-attached to the flexible member 502 prior to employing the repair device 500 with a lacerated tendon. For example, upon being inserted through the flexible member 502, the intermediate portion 536 may extend substantially parallel with the upper surface 518 or outer surface of the flexible member 502. Further, each of the first and second legs 538, 540 may include barbs 542 that may be canted toward the intermediate portion 536. With this arrangement, the barbs 542 may be configured to facilitate ready insertion of the anchors 504 through the flexible member 502 and deter migration of the anchors 504 from the flexible member 502 in the opposite direction.

Further, such barbs 542 may be positioned adjacent a distal end of the first and second legs 538, 540 such that the flexible member 502 may be positioned above or slightly proximal of the barbs 542, as depicted in FIG. 37A. Such flexible member 502 may be moveable along the first and second legs 538, 540 of the anchors 504, as indicated by arrow 543. For example, upon the anchors 504 being in the first anchor position, the flexible member 502 may be in a first flexible member position, as depicted in FIG. 37A, the flexible member 502 being adjacent to and slightly proximal the canted tines or barbs 542. Upon the anchors 504 being moved to the second anchor position, the flexible member 502 may simultaneously move along the first and second legs 538, 540, as shown by arrow 543 in FIG. 37A, to a second flexible member position. In the second flexible member position, the flexible member 502 may be positioned to abut the intermediate portion or upper portion 536 of the anchors 504, as depicted in FIG. 37B. Such flexible member 502 in the first flexible member position may assist in holding the anchors 504 in an aligned and straightened arrangement relative to each other upon the repair device 500 being positioned within a cartridge (not shown), discussed in further detail herein.

Further, in another embodiment, each of the first and second legs 538, 540 can include an end with a point 544. The point 544 may extend and define an angled edge 546 or bevel such that the end portion of each of the legs are cut at an angle. For example, the angled edge 546 at the end of the first leg 538 may be cut in a common direction and orientation relative to the angled edge 546 of the second leg 540. The angled edge 546 or bevel of the legs may be sized and configured to manipulate the direction by which the legs bend to the second anchor position. Further, as depicted in FIG. 37B, with the angled edge 546 being in a common orientation or direction, the first and second legs 538, 540 may bend in a common direction upon being driven into an anvil or within channels defined in a cradle portion (not shown). Further, the point 544 is configured to limit damage to the tendon 5 so as to be readily inserted through the tendon 5.

With respect to FIGS. 36 and 37B, the anchors 504 may be positioned within the flexible member 502 in a staggered arrangement. Further, the anchors 504 may be positioned in the staggered arrangement such that each leg of a given anchor 504 curls or bends in a first direction and an adjacently spaced anchor 504 with its legs bend in a second direction, the first direction being opposite the second direction. In other words, the anchors 504 are staggered relative to each other and each anchor 504 is oriented such that its associated legs bend in opposite directions relative to adjacent anchors 504 along the length 506 of the flexible member 502. As such, the first and second legs 538, 540 of a given anchor bend in a common direction or to a common lateral side with adjacently positioned anchors 504 oriented and bending oppositely.

As set forth, the first and second legs 538, 540 of the multiple anchors 504, upon moving to the second anchor position, move from a linear position to a curled or bent position. In one embodiment, the legs are moved to exhibit a curled portion 548. Such curled portion 548 may be sized and configured to latch or grab a portion of the tendon 5 in a bundled manner. Further, the curled portion of the legs include a radial component 534 or radius sized to extend outside the tendon 5 at a lower portion of the curled portion 548 and then extend back within the tendon 5. The staggered arrangement of the multiple anchors 504 facilitates the curled portions 548 of each anchor 504 to grab and bundle the tendon 5 in a staggered manner relative to adjacent anchors 504.

Figure 38:
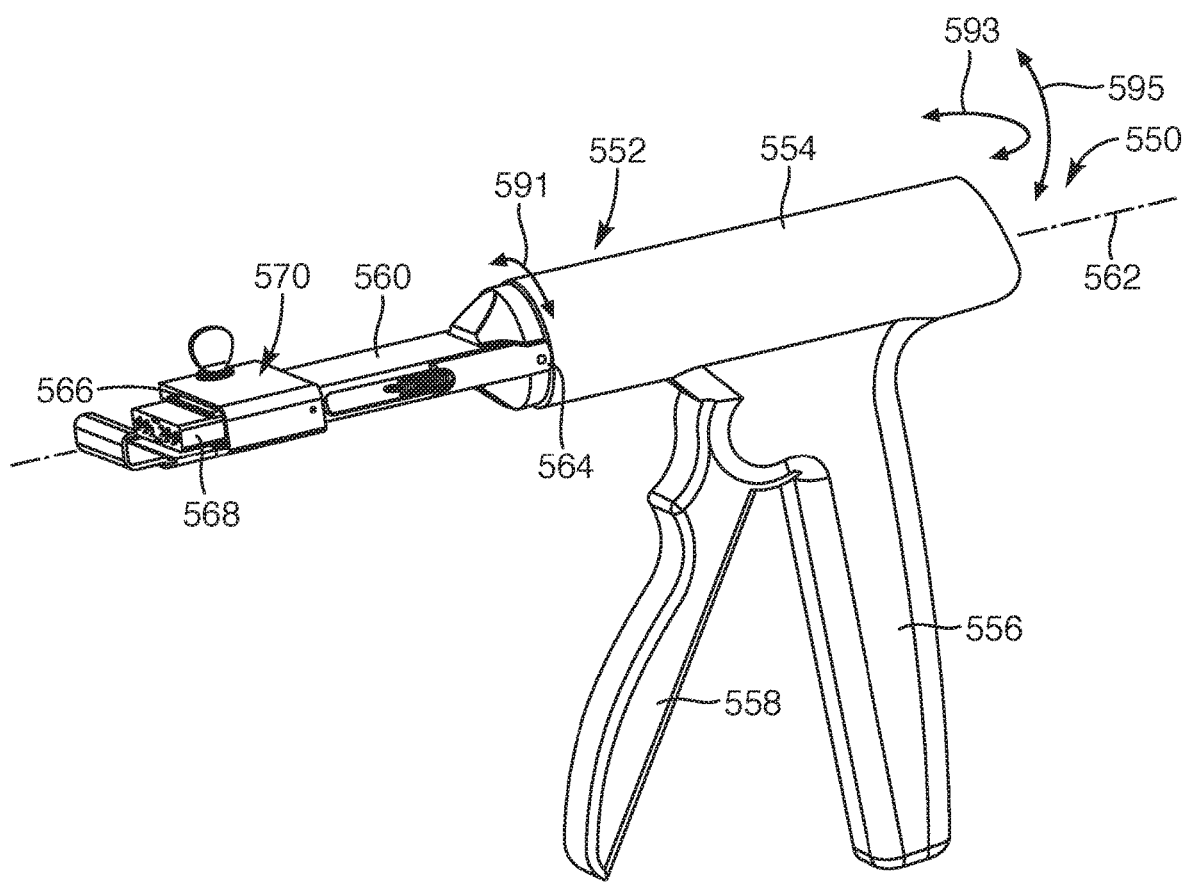
FIG. 38 is a perspective view of a delivery device, depicting the delivery device with a cartridge holding a repair device, according to another embodiment of the present invention.
Figure 39:
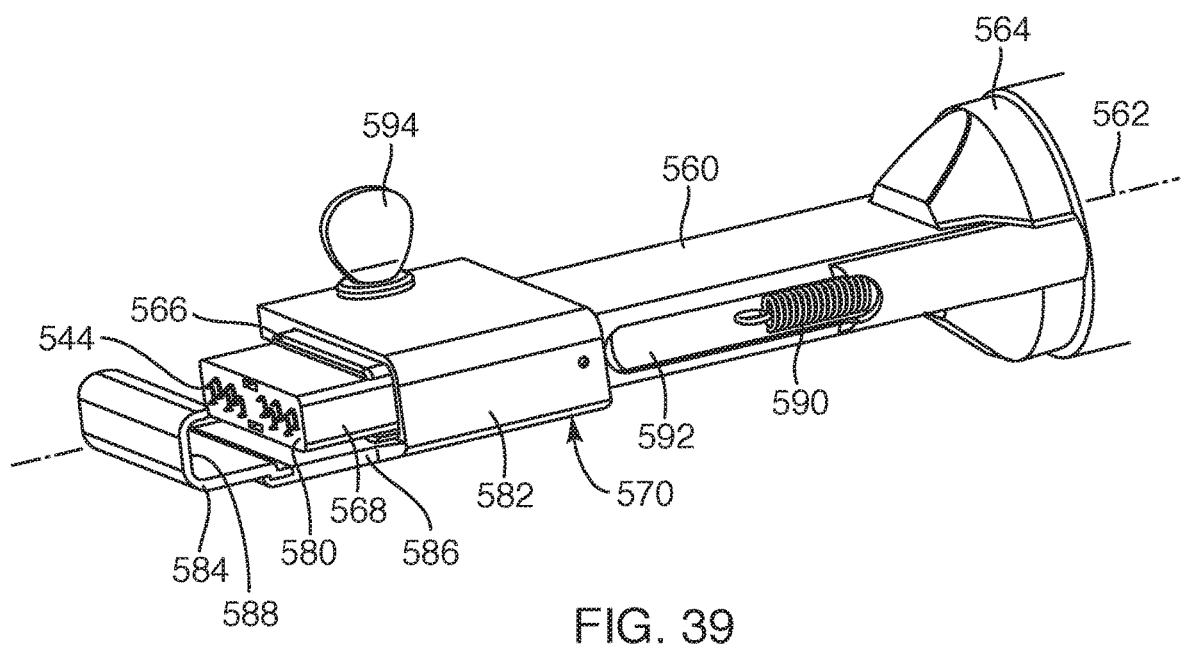
FIG. 39 is an enlarged perspective view of an elongated guide and slider member of the delivery device, according to another embodiment of the present invention.

Now with reference to FIGS. 38 and 39, a medical device system 550 configured to fuse first and second tendon ends of a lacerated tendon is provided. The medical device system 550 includes a delivery device 552 or delivery gun and a repair device, such as the repair device 500 set forth in the previous embodiment.

In one embodiment, the delivery device 552 may include a body 554, a handle 556, a trigger 558, and an elongated guide 560. The handle 556 may extend downward from the body 554 with the trigger 558 associated with the handle 556. The trigger 558 may be a lever like structure or extension positioned adjacent the handle 556 so as allow a physician to grip the handle 556 and the trigger 558 to generate a force to the elongated guide 560. In this manner, the physician may manually actuate the trigger 558, discussed further herein. One example of the body and handle 556 with the trigger 558 that may be coupled to the elongated guide 560 is described in U.S. Pat. No. 5,344,061, the disclosure of which is hereby incorporated herein by reference in its entirety.

The elongated guide 560 may extend distally from the body 554 in a barrel like fashion. The elongated guide 560 may include a square or rectangular lateral cross-section. The elongated guide 560 may extend longitudinally defining an axis 562 between a first end 564 and a second end 566, the first end 564 coupled to the body 554. The second end 566 or distal portion of the elongated guide 560 may include a cartridge 568 and a slider member 570, the cartridge 568 removeably coupled to the second end 566 of the elongated guide 560.

Figure 41:
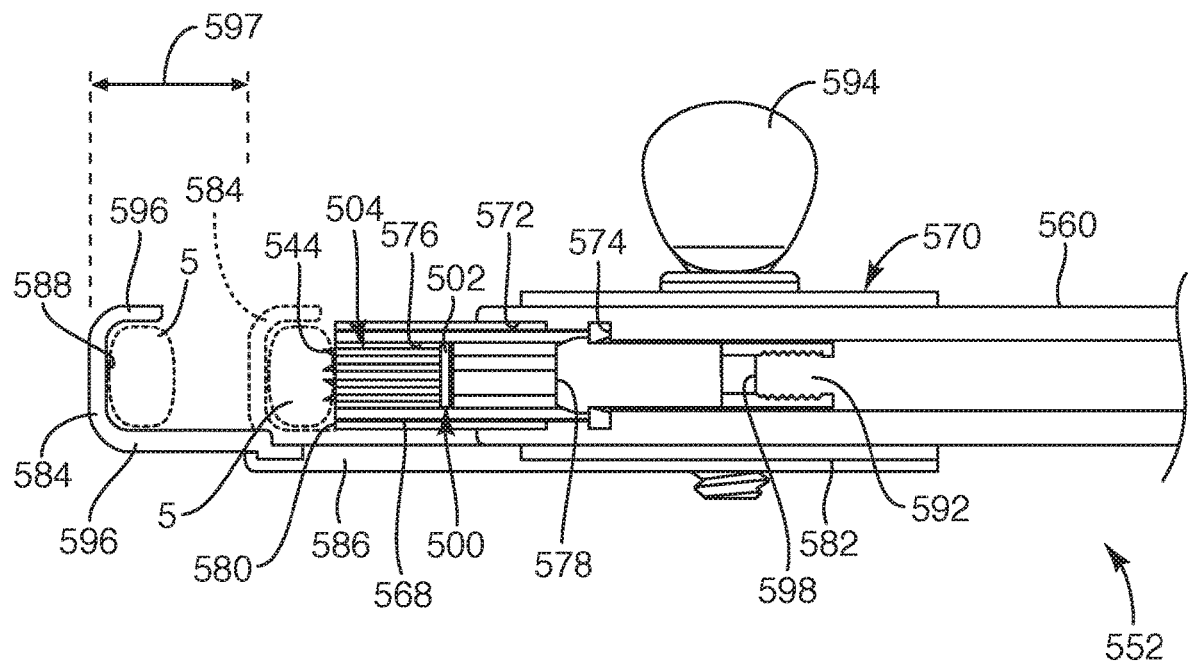
FIG. 41 is an enlarged cross-sectional view of the slider member and the cartridge, depicting a cradle portion in a first position and moveable to a second position, according to another embodiment of the present invention.

With respect to FIGS. 39 and 41, the cartridge 568 may be sized and configured to slide and be inserted into a receiver portion 572 at the distal portion of the elongated guide 560. In one embodiment, the receiver portion 572 may be defined by upper and lower inner surfaces of the elongated guide 560 that include channels or grooves 574 or the like along an inside surface of the distal portion of the elongated guide 560 to facilitate structural outer surface components of the cartridge 568 to be inserted and couple to the receiver portion 572, such as from a lateral side of the elongated guide 560 or inserted at the distal end or second end 566 along the axis 562 of the elongated guide 560.

The cartridge 568 may be sized and configured to hold and position the repair device 500 therein. For example, the cartridge 568 may hold the repair device 500 within a hollow portion 576 defined therein such that the multiple anchors 504 of the repair device 500 may be positioned in the first anchor position (fully extended and linear), as depicted in FIG. 37A. The cartridge 568 may include a first side 578 and a second side 580, the first side 578 opposite the second side 580. The first side 578 of the cartridge 568 may be a driving side configured to be driven by a drive shaft 592. The second side 580 may be an engaging side such that the multiple anchors 504 of the repair device 500 may engage the tendon 5. For example, the second side 580 may exhibit or expose the ends or points 544 of the multiple anchors 504 of the repair device 500 such that the points 544 of the anchors 504 may extend distally or protrude beyond the second side 580 of the cartridge 568. In this manner, the points 544 of the anchors 504 may engage the tendon 5, discussed in further detail herein.

Figure 48:
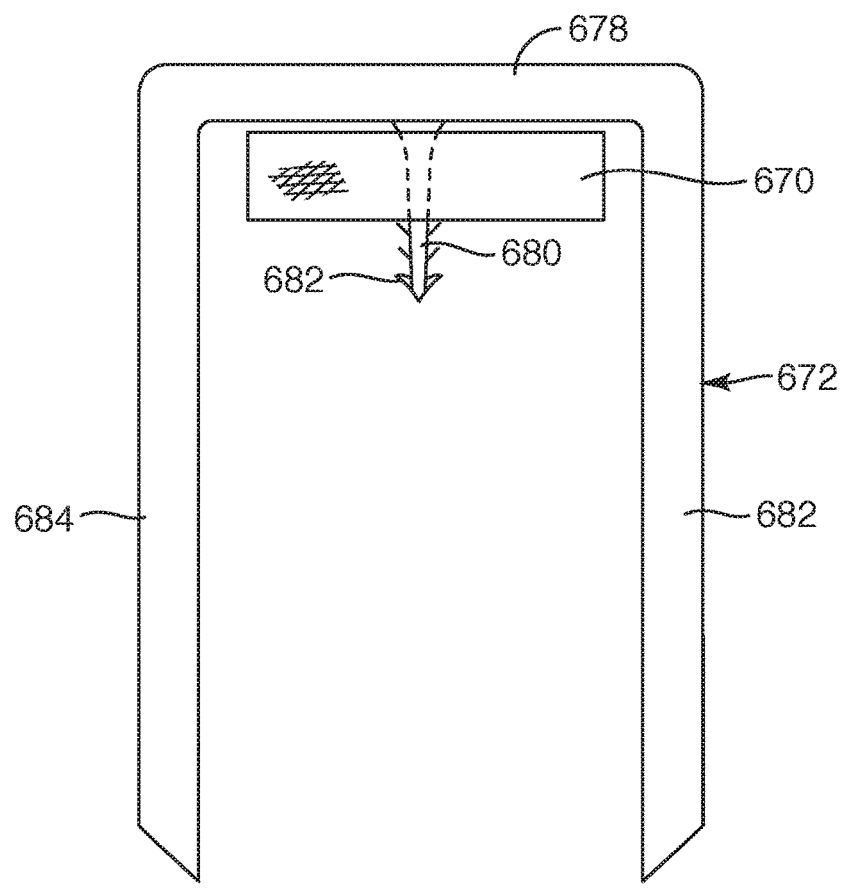
FIG. 48 is an end view of another embodiment of a medical device, according to another embodiment of the present invention.

Further, the repair device 500 may be positioned in the cartridge 568 such that the flexible member 502 may be positioned adjacent the intermediate portion or upper portion (not shown) of the anchors 504 (as depicted in FIG. 41 or 48). In another embodiment, the flexible member 502 may be disposed adjacent the second side 580 of the cartridge 568 and adjacent the points 544 of the anchors (positioned similarly as that depicted in FIG. 37A). In another embodiment, the flexible member 502 may be disposed at any intermediate position along the length of the legs of the anchors 504. In any case, such flexible member 502 may assist in stabilizing the anchors 504 within the cartridge 568 such that the anchors 504 maintain a generally perpendicular orientation relative to the flexible member 502. In another embodiment, the cartridge 568 may include a spring or clip (not shown) associated therewith to stabilize the anchors 504 to maintain a generally perpendicular orientation relative to the flexible member 502.

As set forth, the slider member 570 may be positioned over a distal portion of the elongated guide 560. The slider member 570 may include a slider portion 582 and a cradle portion 584, the cradle portion 584 fixed to the slider portion 582 with an intermediate extension 586 therebetween. Further, the cradle portion 584 may include a bed surface 588 that may face the second side 580 of the cartridge 568. The bed surface 588 may be elongated to define a longitudinal cradle axis, the bed surface 588 configured to receive tendon portions (not shown) with so that an axis of the tendon portions is substantially parallel with the longitudinal cradle axis. Further, the longitudinal cradle axis or a plane of the bed surface maintains a fixed position to be substantially perpendicular relative to the axis 562 of the elongated guide 560.

The slider portion 582 may be slideably coupled to the elongated guide 560, bi-linearly moveable or slidable along a portion of the length of the elongated guide 560. Further, a spring 590 may be disposed within the elongated guide 560 and coupled to the slider member 570 to bias the slider member 570 proximally and, more importantly, to bias the cradle portion 584 proximally. With this arrangement, the cradle portion 584 may be moved between a first cradle position and a second cradle position (shown in outline), as depicted with bi-directional arrow 597. The first cradle position may be an open position such that the cradle portion 584 and slider portion 582 are fully moved distally relative to the elongated guide 560. The second cradle position may be a closed or engaged position such that the cradle portion 584 is moved proximally toward and adjacent to the cartridge 568. In this manner, the cradle portion 584 of the delivery device 552 may be sized and configured to receive first and second end portions of a lacerated tendon 5 along the bed surface 588.

In one embodiment, the slider member 570 may include a locking element 594. The locking element 594 may be actuated between locked and un-locked positions. In the locked position, the locking element 594 may prevent the slider member 570 from linearly moving along the elongated guide 560. Similarly, in the un-locked position, the locking element 594 may be actuated or loosened so as to facilitate the slider member 570 to move proximally via the spring 590 or manually moved distally.

Figure 40:
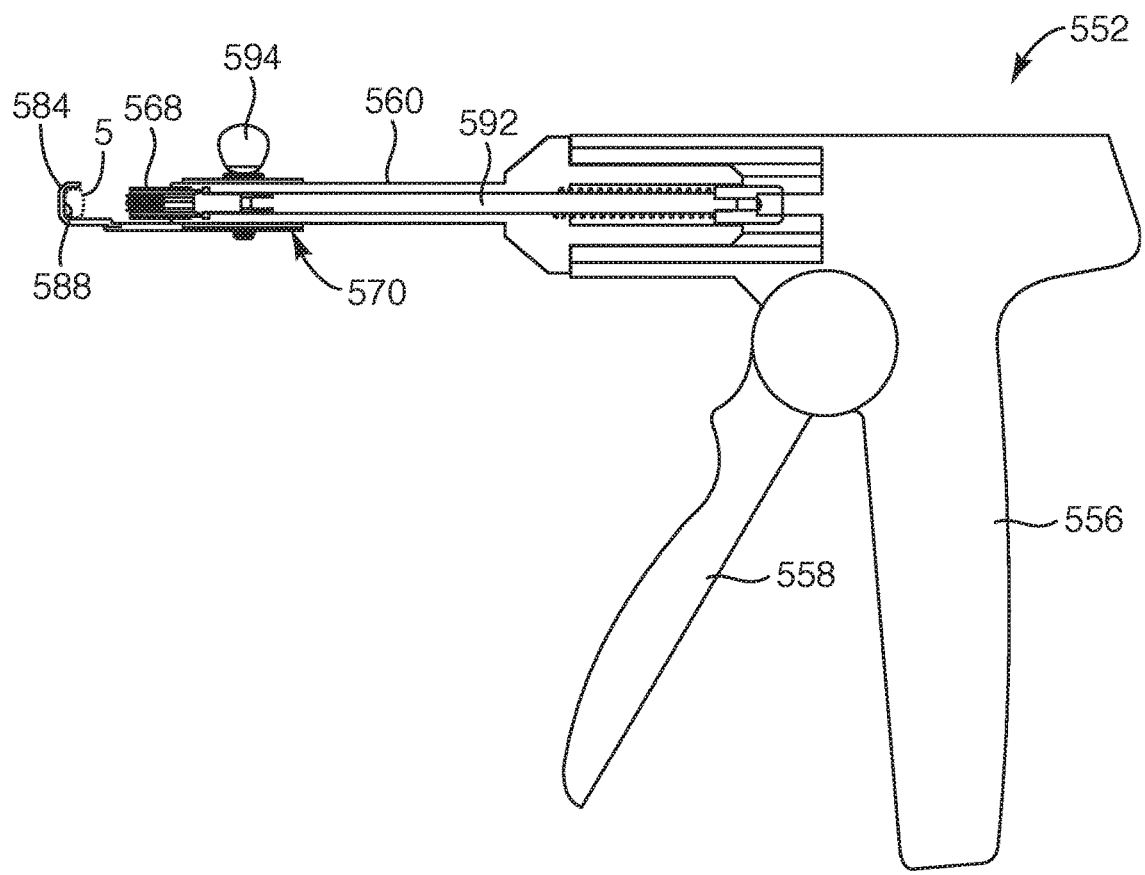
FIG. 40 is a partial cross-sectional side view of the delivery device, according to another embodiment of the present invention.
Figure 42:
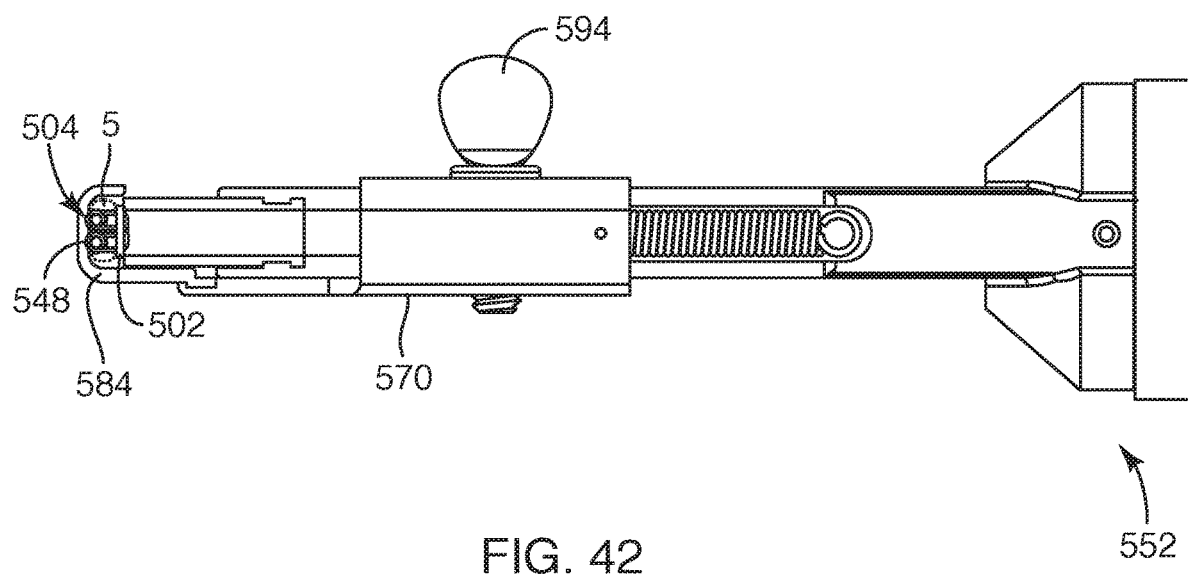
FIG. 42 is an enlarged cross-sectional view of the slider member and cartridge, depicting a drive shaft moved to an engaged position to anchor the repair device to a lacerated tendon, according to another embodiment of the present invention.

Referring now to FIGS. 40 through 42, the method for employing the delivery device 552 to repair a lacerated tendon 5 or ligament will now be described. With respect to FIGS. 40 and 41, the cradle portion 584 of the slider member 570 is depicted in the first cradle position or the open position. In this first cradle position, the cartridge 568 may be slid into and positioned within the distal portion of the elongated guide 560, the cartridge 568 holding the repair device 500 therein. With the cartridge 568 properly positioned, first and second tendon portions of the lacerated tendon 5 may be aligned over the bed surface 588 of the cradle portion 584, the tendon ends abutted against each other and centered. To assist the physician in maintain the tendon portions within the cradle portion 584, the cradle portion 584 may include one or more openings or windows 640 (FIG. 45) extending through the bed surface 588 or lateral sides 596 of the cradle portion 584. Such through holes or windows may assist the physician to extend a needle or a suture therethrough to hold and maintain the tendon portions in the cradle portion 584 or to facilitate increased viewability of the tendon ends.

Once the first and second tendon portions are positioned within the cradle portion 584, the cradle portion 584 may then be moved proximally to the second cradle position (shown in outline form in FIG. 41) or engaged position, as shown by bi-directional arrow 597. Such may be employed by actuating the locking element 594 to an unlocked position. The slider member 570 may then move proximally to the second cradle position. In the second cradle position, the ends or points 544 of the anchors 504 exposed distally beyond the second side 580 of the cartridge 568 are configured to engage the first and second end portions of the lacerated tendon 5 within the cradle portion 584. In this engaged or second cradle position, the tendon end portions may be stabilized and held between the bed surface 588 of the cradle portion 584 and the points 544 of the anchors 504 extending from the cartridge 568 in a sandwiched position.

In another embodiment, the second side 580 of the cartridge 568 may include protrusions or tines (not shown) that may extend distally. Such protrusion or tines may be sized to engage the tendon. In this manner, upon the cradle portion 584 being moved to the second cradle position, the protrusion or tines extending directly from the second side of the cartridge may stabilize the tendon within the cradle portion.

Upon the physician being satisfied with the sandwiched position tendon portions, it may be preferable to move the locking element 594 back into the locked position to stabilize the slider member 570. The physician may then anchor the repair device 500 to the lacerated tendon 5. Such anchoring may be employed by actuating the trigger 558 such that the physician may squeeze the trigger 558 toward the handle 556. While actuating the trigger 558, such movement may actuate and move the drive shaft 592 distally toward the cartridge 568. The drive shaft 592 may include a distal shaft end 598 or pusher block that either contacts or indirectly contacts and moves the repair device 500 distally, out of the cartridge 568, so that the multiple anchors 504 extend through the tendon 5 and engage channels (not shown) defined in the bed surface 588 of the cradle portion 584, as depicted in FIG. 42.

As depicted in FIGS. 37B and 42, the multiple anchors 504, upon being driven within channels of the cradle portion 584, move to the before-described curled portion 548 or curled configuration. As previously set forth, the curled portions 548 of the multiple anchors 504 may grab longitudinally extending bundles of the tendon 5. Further, the multiple anchors 504 hold the elongated flexible member 502 to an exterior surface of the tendon 5 so as to maintain ends of the lacerated tendon 5 abutted against each other. At this juncture, the locking element 594 may be moved to an unlocked position so that the slider member 570 may be distally moved to the first cradle position. The repair device 500 anchored to the lacerated tendon 5 may then be removed from the cradle portion 584. In this manner, the delivery device 552 may be employed to anchor the repair device 500 to a lacerated tendon 5 so that ends of the first and second tendon end portions of the lacerated tendon 5 may be fused together and undergo a proper healing process.

In one embodiment, it is contemplated that the slider member 570, along with its associated cradle portion 584, may be divided into two halves. For example, the slider member 570 may include a first slider portion and a second slider portion with respective first and second cradle portions (not shown), each being independently slideable and moveable. In this embodiment, the first and second slider members may also include its own associated first and second locking elements and springs. With this arrangement, the physician may position a first tendon end portion in the first cradle portion and then slide the first cradle portion against the multiple anchors 504 of the first portion 522 of the repair device 500 to sandwich and hold the first tendon end portion therebetween. Similarly, the second tendon end portion may then be sandwiched between the cradle portion and the multiple anchors 504 of the second portion 524 of the repair device 500. In this manner, similar to the previous embodiment, the first and second ends of the lacerated tendon may be positioned to abut each other in the cradle portion and sandwiched with the multiple anchors 504 holding the tendon in position so that the trigger 558 of the delivery device may be actuated to drive the anchors 504 through the tendon and couple the repair device 500 thereto.

In another embodiment, the slider member may be divided into two halves, similar to that discussed above, except one or both of the two halves may articulate or pivot away from each other. For example, the first and second slider members or cradle portions may pivot away from each other, such as in a v-configuration, to provide additional space for the physician to position the first and second tendon portions in the respective first and second cradle portions.

In another embodiment, it is contemplated that the delivery device may include a safety inter-lock. The safety inter-lock may include features that prevent the physician from using a cartridge 568 and repair device 500 that does not match the dimensions of the tendon.

In another embodiment, as depicted in FIG. 38, the elongated guide 560 may rotate about its longitudinal axis 562 and relative to the body 554, as indicated by rotational arrow 591. Such rotation may facilitate the physician to position the cradle portion 584 at a desired orientation and then rotate the body 554 and handle 556 to the orientation most ergonomic for the physician to perform the procedure. In another embodiment, the body 554 may articulate or rotate side-to-side (as shown by rotational arrow 593) or up and down (rotational arrow 595) relative to the elongated guide 560 of the delivery device 552 such that the body 554 may articulate or rotate in a direction transverse to the longitudinal axis 562 of the elongated guide 560. In this manner, such articulation may ergonomically assist the physician as well as facilitate the viewability of the cradle portion 584 for positioning the lacerated tendon.

Figure 43A:
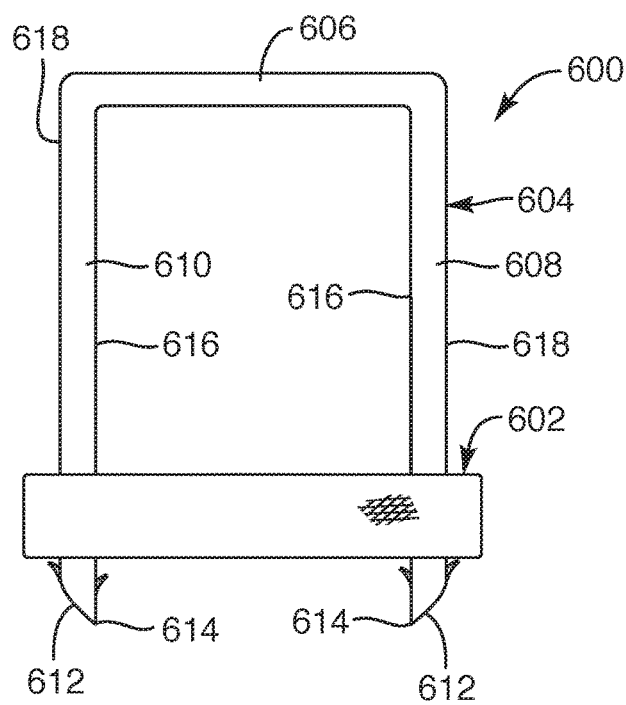
FIGS. 43A and 43B are end views of another embodiment of a repair device, depicting anchors of the repair device in the first anchor position and the second anchor position, respectively, according to the present invention.
Figure 43B:
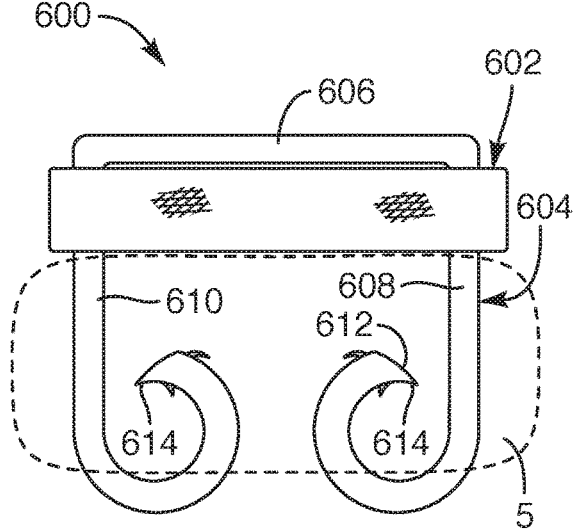

Now with reference to FIGS. 43A and 43B, another embodiment of a repair device 600, similar to the previous embodiment, with anchors 604 pre-inserted through and positioned within a flexible member 602, the anchors 604 being moveable from the first anchor position to the second anchor position. The repair device 600 of this embodiment may be employed in the same manner as described in the previous embodiment, except in this embodiment, the anchors 604 may be aligned along the length of the flexible member 602. Further, in this embodiment, the upper portion 606 or base of the anchors 604 may be longer than the previous embodiment such that the first and second legs 608, 610 of each of the anchors 604 may be spaced with a greater width than the previous embodiment. Further, as depicted in FIG. 43A, the angled edge 612 of the first and second legs 608, 610 may be angled such that the point 614 of each of the first and second legs 608, 610 is at the end of an inner surface 616 of the legs. In other words, the angled edge 612 extends downward or distally from an outer surface 618 of each of the first and second legs 608, 610 to the inner surface 616 of each of the first and second legs 608, 610 of the anchors 604. With this arrangement, upon the anchors 604 being moved to the second anchor position as depicted in FIG. 43B, the angled edge 612 may facilitate the first and second legs 608, 610 to move and curl toward each other in an inward manner. Further, the curled portion of each of the first and second legs 608, 610 may be aligned along the length of the flexible member 602 with curled portions of corresponding ones of the respective first and second legs 608, 610 of the anchors 604. In this manner, the flexible member 622 may be positioned along an exterior surface of a severed tendon 5 with the anchors 604 extending through the flexible member 602 and the tendon 5.

Figure 44A:
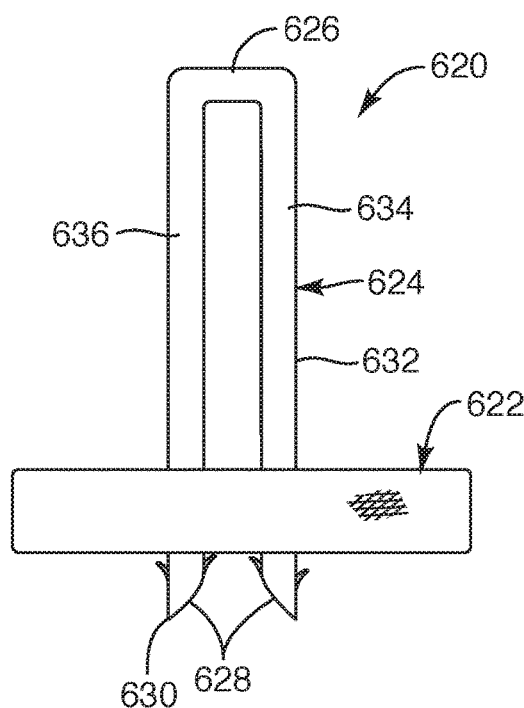
FIGS. 44A and 44B are end views of another embodiment of a repair device, depicting anchors of the repair device in the first and second anchor positions, respectively, according to the present invention.
Figure 44B:
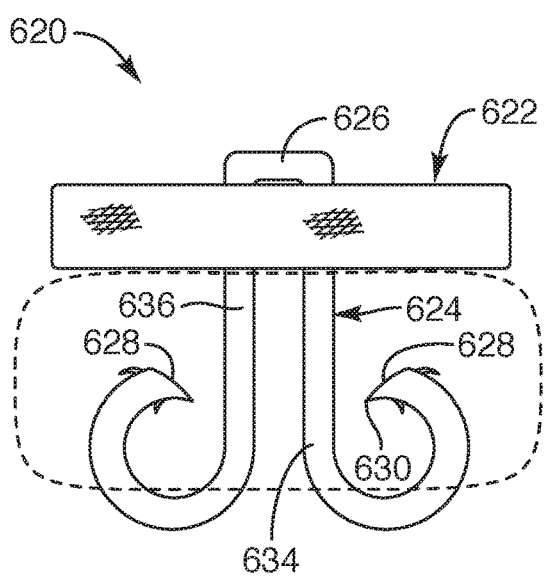

With reference to FIGS. 44A and 44B, another embodiment of a repair device 620, similar to the previous embodiments, having anchors 624 pre-inserted through and positioned within a flexible member 622 and moveable from the first anchor position to the second anchor position. Similar to the previous embodiment, the anchors 624 of this embodiment of the repair device 620 may be aligned in an anchor array along the length of the flexible member 622. The repair device 620 of this embodiment may include anchors 624 with an upper portion 626 or base having a shorter length than the upper portion 626 of previous embodiments. Further, the angled edge 628 extending to define a point 630 may extend distally to the outer surface 632 of each of the first and second legs 634, 636 such that, upon the anchors 624 being moved to the second anchor position, the first and second legs 634, 636 of the anchors 624 may curl outward, as depicted in FIG. 43B. With this arrangement, the flexible member 622 may be positioned along the exterior surface of a severed tendon 5 such that the flexible member 622 may be fixed to the tendon with the anchors 624 extending through the flexible member 622 and the tendon 5.

In another embodiment, the anchors 604 of FIG. 43A and the anchors 624 of FIG. 44A may be positioned along the length of a flexible member in an alternating arrangement. In other words, each anchor 604 of FIG. 43A may be adjacent to one or more of the anchors 624 of FIG. 44A along the length of the flexible member. Upon the anchors of this embodiment being moved to the second anchor position, the curled portions of the first legs of each anchor may be substantially aligned along the length of the flexible member. Similarly, the curled portions of the second legs may be substantially aligned along the length of the flexible member.

Figure 45:
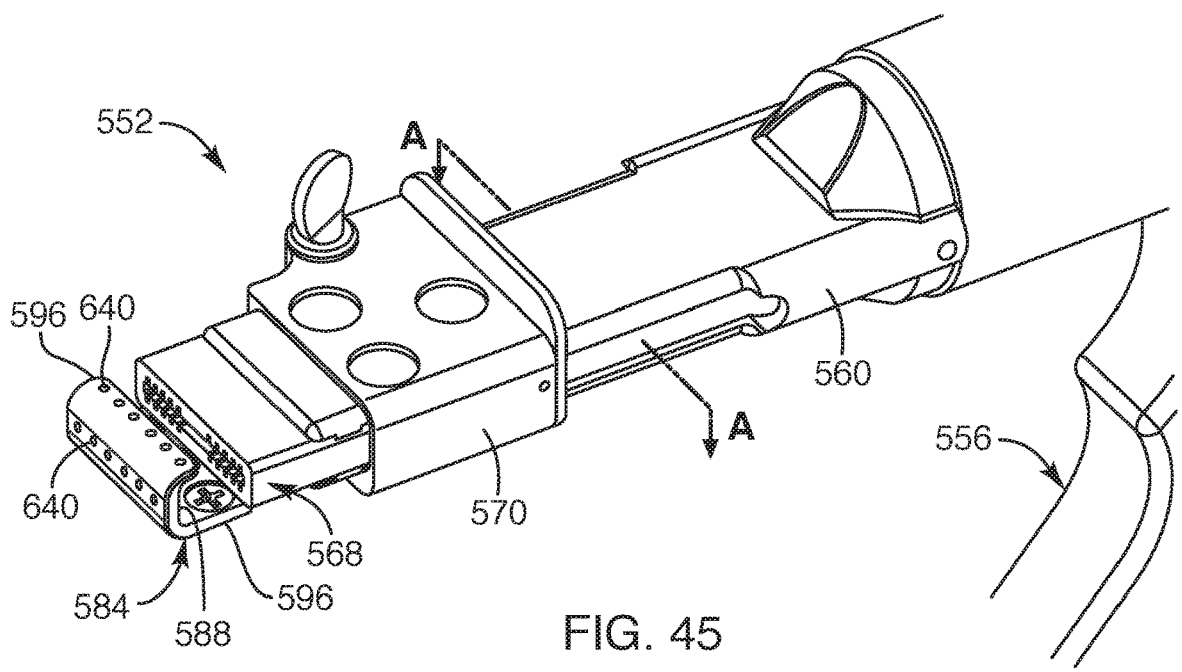
FIG. 45 is a perspective view of another embodiment of a delivery system, according to the present invention.
Figure 45A:
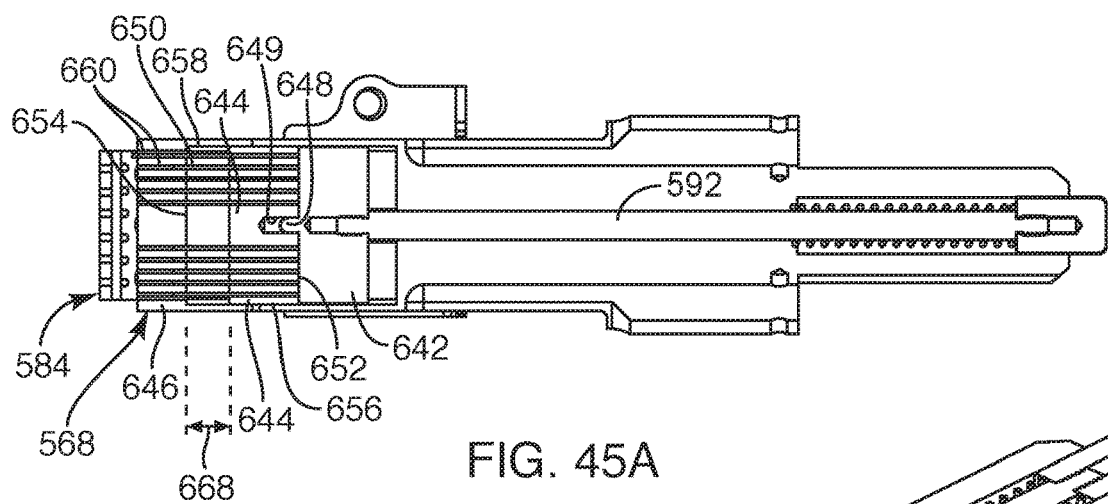
FIG. 45A is a cross-sectional view taken along section A-A of FIG. 45 of the delivery system, according to another embodiment of the present invention.
Figure 46:
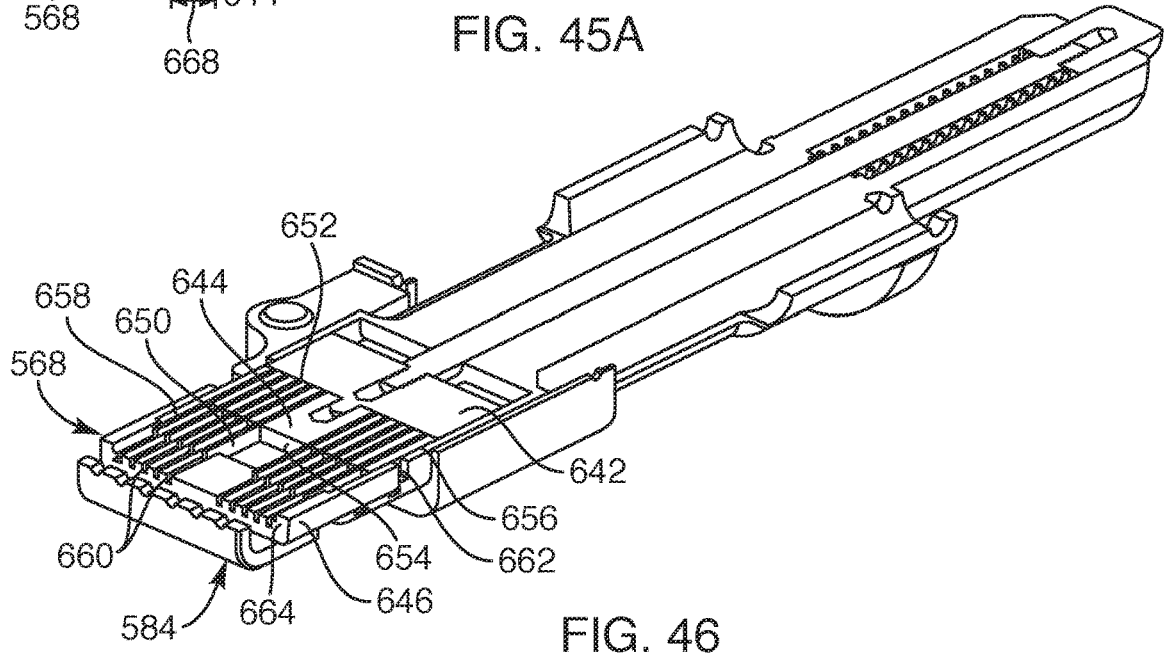
FIG. 46 is a perspective view of the cross-section of FIG. 45A of the delivery system, according to another embodiment of the present invention.

Now with reference to FIGS. 45, 45A, and 46, another embodiment and a more detailed view of a driving mechanism and the cartridge 568 of the delivery device 552, previously set forth, is provided. With respect to FIG. 45, the delivery device 552 includes the elongated guide 560, the cartridge 568 positioned at the end of the elongated guide 560, and the slider member 570 (coupled to the cradle portion 584) moveable along the elongated guide 560, similar to that previously described. In one embodiment, the cradle portion 584 may include multiple through holes 640 extending through the cradle portion 584. For example, the through holes 640 may extend through the bed surface 588 as well as the lateral sides 596 of the cradle portion 584. Such through holes 640 may assist the physician in positioning and holding the severed tendons (not shown) within and along the bed surface 588 via pins or needles or needle/suture arrangements (not shown) or the like. In this manner, the through holes 640 may assist the physician in maintaining the severed tendons positioned within the cradle portion 584 until the cradle portion 584 is moved proximally against the anchor points 544 (and cartridge, as previously described).

With respect to FIGS. 45A and 46, cross-sectional views of the cartridge 568 and driving mechanism for the delivery device 552 are shown. The driving mechanism includes the drive shaft 592, pusher block 642, blade block 644, and an anchor guide 646. The before discussed cartridge 568 may include both the blade block 644 and the anchor guide 646. The drive shaft 592 may be fixed to the pusher block 642 such that the drive shaft 592 may move the pusher block 642 linearly upon actuating the handle 556 (FIG. 45), such that the drive shaft 592 extends along and/or is co-axial with the axis 562 of the elongated guide 560 (FIG. 39). The pusher block 642 may include a protrusion 648 that may align with an aperture 649 defined in the blade block 644 to ensure proper alignment between the cartridge 568 and the pusher block 642.

As set forth, the cartridge 568 may include both the blade block 644 and the anchor guide 646. The blade block 644 may include multiple blades 650 extending distally therefrom. The blade block 644 may include a first side 652, a second side 654 and one or more lateral sides 656. The first side 652 may be opposite the second side 654 with one or more lateral sides 656 extending between the first and second sides 652, 654. The first side 652 may engage the pusher block 642 such that the pusher block 642 may distally force or push the first side 652 of the blade block 644 forward within the anchor guide 646 and toward the cradle portion 584. Further, the one or more lateral sides 656 of the blade block 644 may be disposed at least partially within a hollow portion 658 defined in the anchor guide 646 and at least partially within an end portion of the elongated guide 560. The multiple blades 650 may extend from the second side 654 of the blade block 644 such that the blades 650 extend through the hollow portion 658 of the anchor guide 646 and into slots 660 defined in the anchor guide 646.

Figure 47:
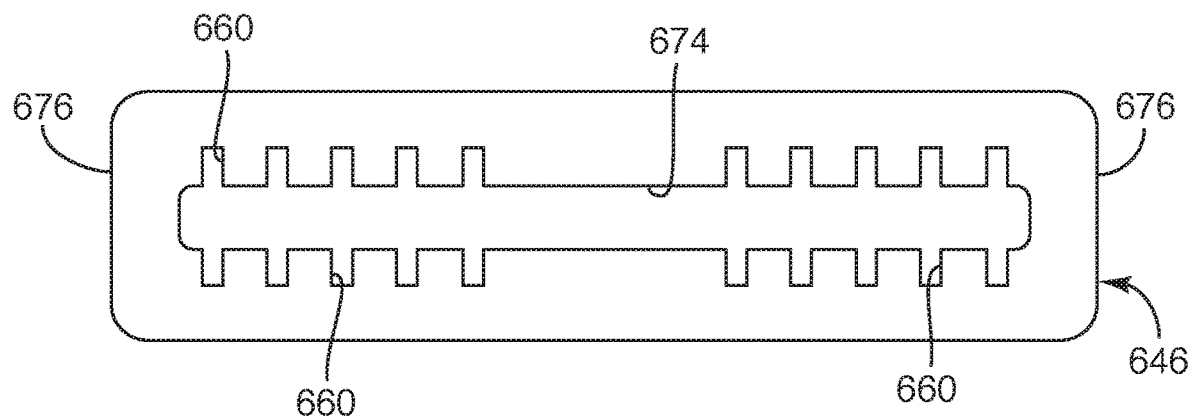
FIG. 47 is an end view of an anchor guide of a cartridge, according to another embodiment of the present invention.

With respect to FIGS. 46 and 47, the anchor guide 646 may include a first end 662 and a second end 664, the second end 664 being the anchor engaging side of the cartridge 568 and the first end 662 defining the hollow portion 658 sized to receive the blade block 644. The anchor guide 646 may include an end portion extending distally from the hollow portion 658 to the second end 664. The end portion of the anchor guide 646 may define slots 660 therein (for example, as depicted in the end view of the anchor guide in FIG. 47). The slots 660 may be sized and configured to each receive a corresponding blade 650 extending from the blade block 644. Further, the slots 660 may hold the anchors (not shown) so that each blade 650 may abut a top surface or upper portion of a corresponding anchor positioned in the slots 660. With this arrangement, as the pusher block 642 is moved forward, the blade block 644 moves from a first position to a second position, as depicted by arrow 668, in FIG. 45A. In this manner, upon positioning a severed tendon within the cradle portion 584 and moving the cradle portion 584 toward the cartridge 568 (as previously described relative to FIGS. 41 and 42), the trigger 558 of the delivery device 552 may be actuated to, thereby, actuate the drive shaft 592 and move the blade block 644 forward to the second position. As the blade block 644 moves to the second position, the blades 650 push the anchors through the slots 660 in the anchor guide 646 and through the severed tendon to fix the flexible member (not shown) to an exterior surface of the severed tendon, as previously described.

Referring now to FIGS. 47 and 48, another embodiment of a flexible member 670 and anchors 672 sized and configured to be disposed within the anchor guide 646. In this embodiment, the anchor guide 646 may include a channel 674 defined in the end portion of the anchor guide 646 (best depicted in the end view of the anchor guide in FIG. 47). The channel 674 may include a longitudinal length (shown to extend horizontally), extending between lateral sides 676 of the anchor guide 646, and extending transverse or perpendicular relative to the length of the slots 660 (shown to extend vertically) holding the anchors. Further, the channel 674 may be defined in the anchor guide 646 so that each slot 660 extends transverse and through the channel 674. In one embodiment, the channel 674 may be sized and configured to position the flexible member 670 therein such that the flexible member 670 is coupled adjacent to an upper portion 678 or base of each anchor 672.

As in previous embodiments, the anchors 672 may include the first and second legs 682, 684 and the upper portion 678 or base extending between the first and second legs 682, 684 in a u-shaped configuration. In addition, the anchors 672 of this embodiment may include a tine 680 or mid-extension. The tine 680 may extend substantially parallel relative to the first and second legs 682, 684. The tine 680 may be configured to maintain the flexible member 670 adjacent (and below) the upper portion 678 of the anchors 672 with, for example, canted tines 686 extending from the tine 680. Further, as set forth, the flexible member 670 may be sized to include a width less than the width of the anchors 672 so that the flexible member 670 is positionable within the channel 674 defined in the anchor guide 646. With this arrangement, the flexible member 670 may be positioned within the cartridge 568 and adjacent the upper portion 678 of the anchors 672, rather than suspended adjacent the anchor points along the second side or end of the anchor guide, as described in earlier embodiments.

Figure 49:
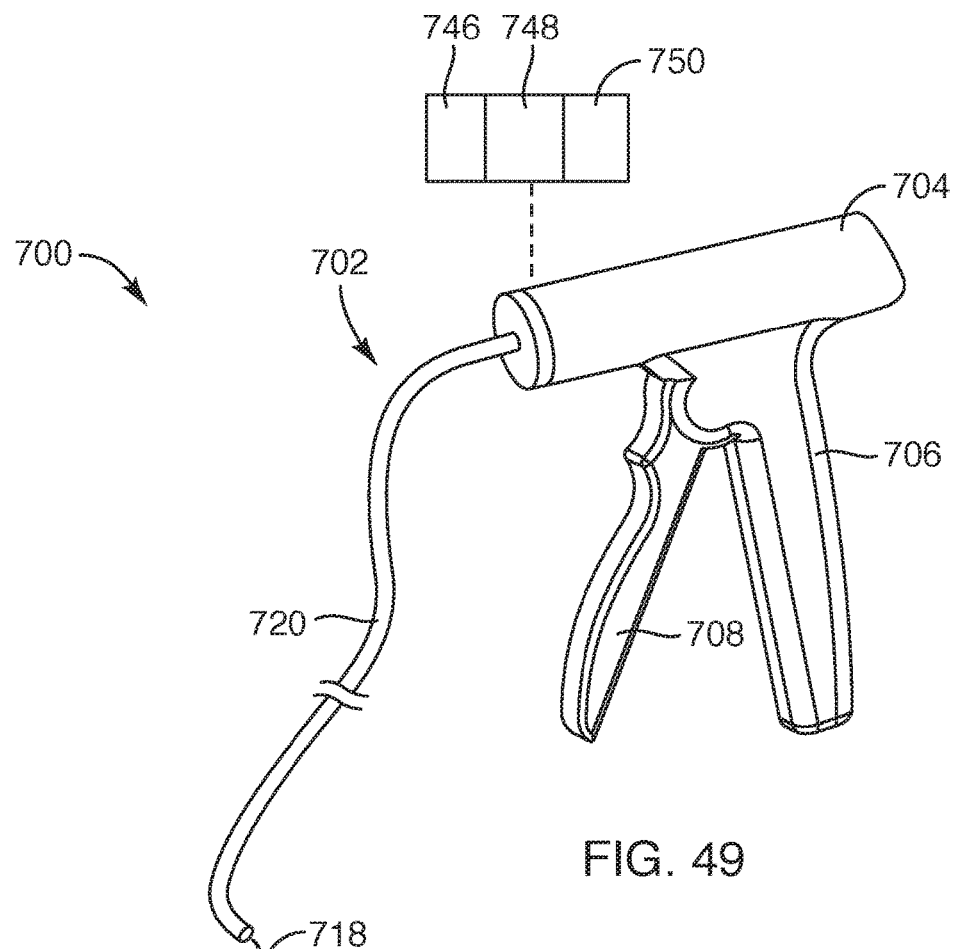
FIG. 49 is a perspective view of another embodiment of a medical device system, depicting a flexible housing for remote actuation of the medical device, according to another embodiment of the present invention.

Now with reference to FIG. 49, another embodiment of a medical device system 700 having a medical device (not shown) and a delivery system 702 is provided. In this embodiment, the delivery system 702 includes a body 704, handle 706, and a trigger 708, each of which may be remote relative to a cartridge 710, slider 712, and elongated guide 714. Further, in this embodiment, the body 704 or trigger mechanism may include a cable or flexible housing 720 that may extend from the body 704. In one embodiment, the flexible housing 720 may be fixed to the, for example, elongated guide 714. In another embodiment, the flexible housing 720 may be removeably coupled to the elongated guide 714 (as indicated by arrow 718) and/or the body 704 of the handle 706 such that, upon the severed tendon being positioned within the cradle 716, the physician may then simply couple the flexible housing 720 and then actuate the trigger 708 at a location remote from the elongated guide 714 to fix the repair device to the severed tendon. Further, in one embodiment, the cable or flexible housing may be operatively coupled to a proximal side of the elongated guide 714 so as to be operatively coupled to the proximal end of the drive shaft 592 (FIG. 45A). The flexible housing 720 may include a driving mechanism for moving the drive shaft and/or the pusher block against the blade block to then push the anchors through the anchor guide and into the tendon, similar to that previously described. As known by one of ordinary skill in the art, such driving mechanism may be formed with a variety of driving mechanisms, such as with a cable, pulleys, a shaft, a coil, or any other suitable driving mechanism known in the art.

Figure 50:
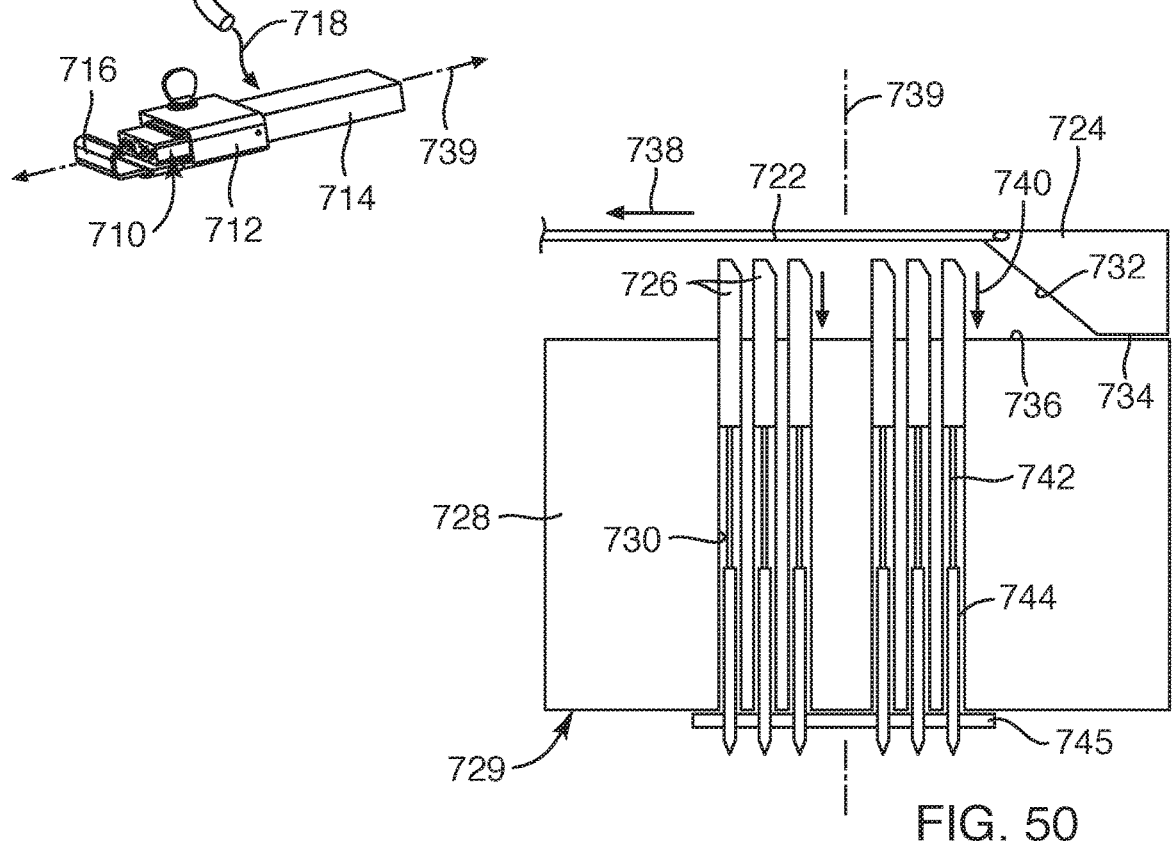
FIG. 50 is a simplistic cross-sectional view of a cartridge and driving mechanism, according to another embodiment of the present invention.

With respect to FIGS. 49 and 50, one embodiment of a driving mechanism is provided. For example, the driving mechanism may include a cable 722 operatively coupled to a drive shaft or pusher block 724. Further, the driving mechanism may interact with an anchor guide 728 and one or more blade blocks 726, the blade blocks 726 sized to slide within slots 730 defined in the anchor guide 728. The cable 722 may extend between the trigger 708 and the pusher block 724, the cable 722 extending through a portion of the elongated guide 714 and through the flexible housing 720. Further, the pusher block 724 may include an angled surface 732 (or radial surface) and may also include a flat surface 734, the angled surface 732 extending to the flat surface 734 similar to a wedge configuration. Further, the flat surface 734 may slide along and abut against a proximal 736 surface of the anchor guide 728.

Upon actuating the trigger 708, the cable 722 may be pulled (in tension) as indicated by arrow 738, transverse to axis 739, axis 739 extending axially through the elongated guide 714. The pusher block 724 may then move along the proximal surface 736 so that the angled surface 732 of the pusher block 724 pushes against the one or more blade blocks 726 extending through the slots 730 of the anchor guide 728. As the pusher block 724 continues to move in the direction of arrow 738, the angled surface 732 of the pusher block 724 moves the blade blocks 726 downward or a perpendicular direction relative to arrow 738, as indicated by arrow 740. In other words, the direction of movement of the pusher block 724 may be transverse or substantially perpendicular to the direction of movement of the blade blocks 726. In this manner, the one or more blade blocks 726 may move through the slots 730 such that blades 742 push the anchors 744 through the slots 730 and into the severed tendon positioned in the cradle portion (not shown) with the flexible member 745 fixed externally to the severed tendon, similar to that described earlier.

In one embodiment, the one or more blade blocks 726 may include multiple blade blocks such that a single blade 742 corresponds with each blade block 726. In another embodiment, the one or more blade blocks 726 may include multiple blade blocks such that each blade block corresponds with multiple blades 742. In another embodiment, there may be, for example, two blade blocks 726, each blade block including multiple blades 742 corresponding with the number of anchors 744 for each side of the flexible member 745. In another embodiment, the one or more blade blocks 726 may include a single blade block with multiple blades 742, each blade corresponding with a single anchor 744. In this manner, the anchors 744 may be anchored and fixed to the tendon in a simultaneous manner or a consecutive/sequential manner.

While the above embodiment sets forth a wedge type configuration as the pusher block/cable arrangement to drive the one or more blade blocks 726, other mechanisms may also be employed, such as multiple wedges to correspond with multiple blade blocks, a rocker configuration, a wheel/cam arrangement, multiple lever arrangement, a rocker arrangement. Further, other embodiments may include spring-loaded plungers to force one or more blade blocks into the anchor guide. In another embodiment, the driving mechanism may include a pneumatic device 746, a hydraulic device 748, and/or an electro-mechanical device 750 coupled to the delivery system (see FIG. 49) for controlling actuation of the pusher block and/or the blade blocks, as depicted in FIG. 49, which may be integrated and employed as known to one of ordinary skill in the art.

In another embodiment, the flexible member 745 may be positioned and fixed to an opposite side of the tendon than that which has been set forth in some of the previous embodiments. Such may be employed, for example, by positioning the flexible member 745 on the bed surface of the cradle portion 716 (rather than being held adjacent the points of the anchors 744), and then positioning the severed tendons over the flexible member 745. The anchors 744, extending slightly from the cartridge 729, may then pin the tendon between the distal side of the cartridge 729 and the bed surface of the cradle portion 716. The delivery system 702 may then be actuated, thereby, actuating the anchors 744 through the tendon and then through the flexible member 745. In this manner, the flexible member 745 may be positioned and fixed to the opposite side of the tendon, that is, the opposite side from which the anchors 744 first enter the tendon.

The various repair device embodiments disclosed herein may be applied to any one of various tendon and/or ligament repairs as well as tendon and/or ligament to bone repairs. For example, the various repair device embodiments may be employed for flexor tendon repairs, patellar tendon repairs, Achilles tendon repairs, quadriceps tendon repairs, and/or bicep tendon repairs, or any other tendon, ligament, and tendon/ligament to bone repairs.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes employing any portion of one embodiment with another embodiment, all modifications, equivalents, and alternatives, falling within the spirit and scope of the invention as defined by the following appended claims.

What is claimed is:

1. A method for repairing a lacerated tendon or ligament having a first end and a second end, the method comprising:
providing a delivery device having a drive shaft defining a drive shaft axis and a removable cartridge positioned distal the drive shaft, the cartridge holding an elongated flat flexible member with multiple anchors coupled to the elongated flat flexible member, each of the multiple anchors being separate and discrete structures relative to each other, and each of the multiple anchors having a base with two legs extending generally perpendicular from ends of the base;
positioning a first end portion and a second end portion of the tendon or ligament within an elongated bed surface of a cradle of the delivery device with the first and second ends of the tendon or ligament abutted against each other, the elongated bed surface defining a cradle axis such that the cradle axis is perpendicular to the drive shaft axis; and
coupling the elongated flat flexible member with the multiple anchors to the first end portion and the second end portion within the cradle by actuating a trigger of the delivery device so as to actuate the drive shaft distally to effect movement of the anchors from the cartridge such that the two legs of each of the anchors at least partially move through the elongated flat flexible member and through the first or second end portions of the tendon or ligament so that the two legs of each of the anchors compress against the bed surface of the cradle and so that the two legs of each of the anchors curl back into the tendon or ligament such that, upon compression of the multiple anchors, the base of each of the multiple anchors is oriented to extend substantially perpendicular relative to the drive shaft axis and the cradle axis of the delivery device.

2. The method according to claim 1, wherein the positioning comprises positioning the first end portion and the second end portion of the tendon or ligament within the cradle so that free ends of the legs of the multiple anchors are positioned adjacent the first and second end portions of the tendon or ligament, the legs extending within the cartridge substantially parallel with the drive shaft axis and extending substantially perpendicular with the cradle axis.

3. The method according to claim 1, wherein the coupling comprises compressing the multiple anchors through the first end portion and the second end portion such that end portions of the legs of each of the multiple anchors curl and bundle portions of the tendon or ligament.

4. The method according to claim 1, wherein the providing comprises providing the elongated flat flexible member having a lattice structure such that the multiple anchors are coupled to the lattice structure.

5. The method according to claim 1, wherein the providing comprises providing the elongated flat flexible member with an elongated length defining a first portion and a second portion with an intermediate portion therebetween, the first and second portions being configured to elongate along the elongated length and the intermediate portion being configured to substantially resist elongation.

6. The method according to claim 5, wherein the coupling comprises coupling the elongated flat flexible member to the first and second end portions of the tendon or ligament so that the first and second portions of the elongated flat flexible member elongate along the elongated length thereof as the tendon or ligament elongates with the intermediate portion substantially resisting elongation so that the first and second ends of the tendon or ligament fuse together.

7. The method accord to claim 5, wherein the providing comprises providing the elongated flat flexible member with a lattice structure defining a longitudinal axis defined along the elongated length of the elongated flat flexible member, the lattice structure at the intermediate portion extends at a first angle relative to a longitudinal axis of the elongated flat flexible member and the lattice structure at the first and second portions extends at a second angle relative to the longitudinal axis of the elongated flat flexible member, the first angle being smaller than the second angle.

8. The method according to claim 1, wherein the providing comprises providing the elongated flat flexible member having at least one of one or more polymeric filaments and a metallic structure.

9. The method according to claim 1, wherein the coupling comprises coupling the multiple anchors to the elongated flat flexible member and the tendon or ligament such that the base of each of the multiple anchors extends with an elongated length that is oriented to longitudinally extend transverse relative to a longitudinal orientation of the elongated flat flexible member.

10. The method according to claim 1, wherein the coupling comprises securing the elongated flat flexible member to both the first and second end portions of the tendon or ligament with the multiple anchors to substantially fixate the first end of the tendon or ligament adjacent to the second end of the tendon or ligament.

11. A method for repairing soft tissue having a first end and a second end, the method comprising:
   providing a delivery device including an anvil and a driving member configured to cooperate with a medical device, the driving member configured to move along a driving member axis, the anvil being elongated to define an anvil axis, the driving member axis being substantially perpendicular relative to the anvil axis, the medical device having multiple anchors and an elongated flat flexible member, each of the multiple anchors being separate and discrete structures relative to each other, and each of the multiple anchors having a base with two legs extending generally perpendicular from ends of the base;
   positioning a first end portion and a second end portion of the soft tissue over the anvil of the delivery device with the first end of the soft tissue abutted against the second end of the soft tissue; and
   securing the elongated flat flexible member to both the first and second end portions of the soft tissue with the multiple anchors extending through the elongated flat flexible member and through the first and second end portions of the soft tissue to substantially fixate the first end of the soft tissue adjacent to the second end of the soft tissue such that, upon securing the elongated flat flexible member, the base of each of the anchors is oriented to extend substantially perpendicular relative to the driving member axis and the anvil axis of the delivery device.

12. The method according to claim 11, wherein the securing comprises compressing the multiple anchors with the driving member so that the two legs of each of the multiple anchors are formed against the anvil and curl back into the soft tissue.

13. The method according to claim 11, wherein the securing comprises driving the multiple anchors from a cartridge with the driving member, the cartridge sized and configured to hold the multiple anchors therein.

14. The method according to claim 11, wherein the providing comprises providing the elongated flat flexible member with a lattice structure, the lattice structure sized and configured to facilitate the two legs of each anchor to pass therethrough.

15. The method according to claim 11, wherein the providing comprises providing the elongated flat flexible member having at least one of one or more polymeric filaments and a metallic structure.

16. The method according to claim 11, wherein the securing comprises securing the multiple anchors to the elongated flat flexible member and the soft tissue such that the base of each of the multiple anchors extends with an elongated length that is oriented to longitudinally extend transverse relative to a longitudinal orientation of the elongated flat flexible member.

17. A method for repairing a lacerated tendon or ligament having a first end and a second end, the method comprising:
   providing a delivery device having a drive shaft defining a drive shaft axis and a removable cartridge positioned distal the drive shaft, the cartridge holding an elongated flat flexible member with multiple anchors coupled to the elongated flat flexible member;
   positioning a first end portion and a second end portion of the tendon or ligament within an elongated bed surface of a cradle of the delivery device with the first and second ends of the tendon or ligament abutted against each other, the elongated bed surface defining a cradle axis such that the cradle axis is perpendicular to the drive shaft axis; and
   coupling the elongated flat flexible member with the multiple anchors to the first end portion and the second end portion within the cradle by actuating a trigger of the delivery device so as to actuate the drive shaft distally to effect movement of the anchors from the cartridge through the elongated flat flexible member and into the first and second end portions of the tendon or ligament so that the anchors compress against the bed surface of the cradle and so that the anchors curl back into the tendon or ligament;
   wherein the providing comprises providing the elongated flat flexible member with an elongated length defining a first portion and a second portion with an intermediate portion therebetween, the first and second portions being configured to elongate along the elongated length and the intermediate portion being configured to substantially resist elongation.

18. The method according to claim 17, wherein the providing comprises providing the elongated flat flexible member having a lattice structure such that the multiple anchors are coupled to the lattice structure.

19. The method according to claim 17, wherein the providing comprises providing the elongated flat flexible member having at least one of one or more polymeric filaments and a metallic structure.

20. The method according to claim 17, wherein the coupling comprises coupling the multiple anchors to the elongated flat flexible member and the tendon or ligament such that a base of each of the multiple anchors extends with an elongated length that is oriented to longitudinally extend transverse relative to a longitudinal orientation of the elongated flat flexible member.

* * * * *